(12) United States Patent  
Podolsky

(10) Patent No.: US 8,211,183 B2  
(45) Date of Patent: Jul. 3, 2012

(54) METHODS AND SYSTEMS FOR TOTAL HIP REPLACEMENT

(75) Inventor: Anatol Podolsky, Corona Del Mar, CA (US)

(73) Assignee: iHip Surgical, LLC, Newport Beach, CA (US)

( * ) Notice: Subject to any disclaimer, the term of this patent is extended or adjusted under 35 U.S.C. 154(b) by 0 days.

(21) Appl. No.: 13/049,619

(22) Filed: Mar. 16, 2011

(65) Prior Publication Data

US 2011/0166665 A1   Jul. 7, 2011

Related U.S. Application Data

(62) Division of application No. 12/518,081, filed as application No. PCT/US2006/046795 on Dec. 7, 2006, now Pat. No. 8,029,573.

(51) Int. Cl.  
*A61F 2/32* (2006.01)

(52) U.S. Cl. .................................... 623/22.15

(58) Field of Classification Search .... 623/22.11–22.46, 623/23.11–23.12, 23.15; 606/64, 65, 86 R, 606/87–91  
See application file for complete search history.

(56) References Cited

U.S. PATENT DOCUMENTS

| | | | |
|---|---|---|---|
| 2,679,245 A | 5/1954 | Timmermans |
| 2,682,265 A | 6/1954 | Collison |
| 2,718,228 A | 9/1955 | Van Steenbrugghe |
| 2,719,522 A | 10/1955 | Hudack |
| 2,781,758 A | 2/1957 | Chevalier |
| 2,785,673 A | 3/1957 | Anderson |
| 3,064,645 A | 11/1962 | Ficat et al. |
| 3,067,740 A | 12/1962 | Haboush |
| 3,466,670 A | 9/1969 | Christiansen |
| 3,512,184 A | 5/1970 | Groove |
| 3,605,123 A | 9/1971 | Hahn |
| 3,656,184 A | 4/1972 | Chambers |
| 3,683,421 A | 8/1972 | Martinie |

(Continued)

FOREIGN PATENT DOCUMENTS

DE    2620907    11/1977

(Continued)

OTHER PUBLICATIONS

International Search Report; mailed Sep. 12, 2007; International Patent Application No. PCT/US2006/046795; 1 page.

*Primary Examiner* — Alvin J Stewart  
(74) *Attorney, Agent, or Firm* — Knobbe Martens Olson & Bear, LLP

(57) ABSTRACT

Methods and apparatus of the present invention provide for orthopaedic total replacement of the hip while substantially preserving muscles and soft tissues around the hip joint resulting in reduced healing time and decreased risk of dislocation following the procedure. In an exemplary embodiment, the acetabulum is prepared and fitted with a prosthetic acetabular cup 702 and a prosthetic femoral head 1102 is fitted into the prosthetic acetabular cup 702. An intramedullary rod 1502 is inserted longitudinally into the femur. A prosthetic femoral neck 3102 is then inserted from a point along the side of the patient's body and into the side of the femur and through a pre-existing lateral bore in the intramedullary rod 1502 and through the remainder of the femur to join the prosthetic femoral head 1102. The methods and apparatus include structures and techniques for fixing the prosthetic femoral neck 3102 in relation to the intramedullary rod 1502.

26 Claims, 38 Drawing Sheets

U.S. PATENT DOCUMENTS

| | | |
|---|---|---|
| 3,806,957 A | 4/1974 | Shersher |
| 3,829,904 A | 8/1974 | Ling et al. |
| 3,848,272 A | 11/1974 | Noiles |
| 3,875,593 A | 4/1975 | Shersher |
| 3,896,505 A | 7/1975 | Timmermans |
| 3,906,550 A | 9/1975 | Rostoker et al. |
| 3,918,441 A | 11/1975 | Getscher |
| 3,943,576 A | 3/1976 | Sivash |
| 3,978,528 A | 9/1976 | Crep |
| 3,987,499 A | 10/1976 | Scharback et al. |
| 4,016,651 A | 4/1977 | Kawahara et al. |
| 4,051,559 A | 10/1977 | Pifferi |
| 4,080,666 A | 3/1978 | Fixel |
| 4,086,701 A | 5/1978 | Kawahara et al. |
| 4,089,071 A | 5/1978 | Kalnberz et al. |
| 4,101,985 A | 7/1978 | Baumann et al. |
| 4,129,903 A | 12/1978 | Huggler |
| 4,259,072 A | 3/1981 | Hirabayashi et al. |
| 4,304,110 A | 12/1981 | Fain |
| 4,318,191 A | 3/1982 | Tepic |
| 4,385,405 A | 5/1983 | Teinturier |
| 4,404,691 A | 9/1983 | Bunning et al. |
| 4,488,319 A | 12/1984 | Von Recüm |
| 4,520,511 A | 6/1985 | Gianezio et al. |
| 4,530,114 A | 7/1985 | Tepic |
| 4,532,660 A | 8/1985 | Field |
| 4,532,661 A | 8/1985 | Halpern |
| 4,578,081 A | 3/1986 | Harder et al. |
| 4,619,659 A | 10/1986 | Witzel |
| 4,624,673 A | 11/1986 | Meyer |
| 4,630,601 A | 12/1986 | Harder et al. |
| 4,676,797 A | 6/1987 | Anapliotis et al. |
| 4,693,724 A | 9/1987 | Rhenter et al. |
| 4,709,854 A | 12/1987 | Biagini et al. |
| 4,712,541 A | 12/1987 | Harder et al. |
| 4,714,471 A | 12/1987 | Grundei |
| 4,714,478 A | 12/1987 | Fischer |
| 4,728,330 A | 3/1988 | Comparetto |
| 4,728,334 A | 3/1988 | Spotorno |
| 4,733,654 A | 3/1988 | Marino |
| 4,752,295 A | 6/1988 | Frey et al. |
| 4,752,296 A | 6/1988 | Buechel et al. |
| 4,776,330 A | 10/1988 | Chapman et al. |
| 4,795,473 A | 1/1989 | Grimes |
| 4,822,368 A | 4/1989 | Collier |
| 4,823,366 A | 4/1989 | Williams |
| 4,827,917 A | 5/1989 | Brumfield |
| 4,834,756 A | 5/1989 | Kenna |
| 4,842,606 A | 6/1989 | Kranz et al. |
| 4,846,839 A | 7/1989 | Noiles |
| 4,851,007 A | 7/1989 | Gray |
| 4,871,369 A | 10/1989 | Muller |
| 4,878,917 A | 11/1989 | Kranz et al. |
| 4,895,571 A | 1/1990 | Grundei |
| 4,904,264 A | 2/1990 | Scheunemann |
| 4,908,032 A | 3/1990 | Keller |
| 4,917,530 A | 4/1990 | Engelhardt et al. |
| 4,919,673 A | 4/1990 | Willert et al. |
| 4,919,678 A | 4/1990 | Kranz |
| 4,919,679 A * | 4/1990 | Averill et al. .............. 623/22.12 |
| 4,936,853 A | 6/1990 | Fabian et al. |
| 4,938,773 A | 7/1990 | Strand |
| 4,944,764 A | 7/1990 | Stossel |
| 4,946,461 A | 8/1990 | Fischer |
| 4,957,510 A | 9/1990 | Cremascoli |
| 4,963,155 A | 10/1990 | Lazzeri et al. |
| 4,976,740 A | 12/1990 | Kleiner |
| 4,978,357 A | 12/1990 | Goymann et al. |
| 4,985,037 A | 1/1991 | Petersen |
| 4,994,085 A | 2/1991 | Sawai et al. |
| 4,995,883 A | 2/1991 | Demane et al. |
| 4,998,937 A | 3/1991 | Grimes |
| 5,002,578 A | 3/1991 | Luman |
| 5,002,581 A | 3/1991 | Paxson et al. |
| 5,007,935 A | 4/1991 | Vincent et al. |
| 5,019,108 A | 5/1991 | Bertin et al. |
| 5,026,280 A | 6/1991 | Dürr et al. |
| 5,035,712 A | 7/1991 | Hoffman |
| 5,047,033 A | 9/1991 | Fallin |
| 5,058,936 A | 10/1991 | Kapgan et al. |
| 5,080,676 A | 1/1992 | May |
| 5,080,685 A | 1/1992 | Bolesky et al. |
| 5,087,260 A | 2/1992 | Fixel |
| 5,100,407 A | 3/1992 | Conrad et al. |
| 5,108,437 A | 4/1992 | Kenna |
| 5,108,451 A | 4/1992 | Forte |
| 5,108,452 A | 4/1992 | Fallin |
| 5,116,379 A | 5/1992 | McLardy-Smith |
| 5,123,926 A | 6/1992 | Pisharodi |
| 5,133,760 A | 7/1992 | Petersen et al. |
| 5,133,771 A | 7/1992 | Duncan et al. |
| 5,133,772 A | 7/1992 | Hack et al. |
| 5,135,529 A | 8/1992 | Paxson et al. |
| 5,139,424 A | 8/1992 | Yli-Urpo |
| 5,152,796 A | 10/1992 | Slamin |
| 5,152,798 A | 10/1992 | Kranz |
| 5,156,626 A * | 10/1992 | Broderick et al. ......... 623/22.12 |
| 5,163,961 A | 11/1992 | Harwin |
| 5,167,663 A | 12/1992 | Brumfield |
| 5,181,928 A | 1/1993 | Bolesky et al. |
| 5,190,546 A | 3/1993 | Jervis |
| 5,193,679 A | 3/1993 | White |
| 5,194,066 A | 3/1993 | Van Zile |
| 5,197,720 A | 3/1993 | Renz et al. |
| 5,197,988 A | 3/1993 | Spotorno et al. |
| 5,197,989 A | 3/1993 | Hinckfuss et al. |
| 5,201,769 A | 4/1993 | Schutzer |
| 5,201,882 A | 4/1993 | Paxson |
| 5,211,666 A | 5/1993 | Fetto |
| 5,259,249 A | 11/1993 | Fetto |
| 5,286,260 A | 2/1994 | Bolesky et al. |
| 5,312,406 A | 5/1994 | Brumfield |
| 5,314,479 A | 5/1994 | Rockwood, Jr. et al. |
| 5,336,268 A | 8/1994 | Rispeter |
| 5,342,366 A | 8/1994 | Whiteside et al. |
| 5,344,457 A | 9/1994 | Pilliar et al. |
| 5,370,706 A | 12/1994 | Bolesky et al. |
| 5,376,124 A | 12/1994 | Gustke et al. |
| 5,376,125 A | 12/1994 | Winkler |
| 5,389,107 A | 2/1995 | Nassar et al. |
| 5,390,683 A | 2/1995 | Pisharodi |
| 5,454,813 A | 10/1995 | Lawes |
| 5,458,654 A | 10/1995 | Tepic |
| 5,489,309 A | 2/1996 | Lackey et al. |
| 5,489,311 A | 2/1996 | Cipolletti |
| 5,507,817 A | 4/1996 | Craig et al. |
| 5,507,826 A | 4/1996 | Besselink et al. |
| 5,507,830 A | 4/1996 | DeMane et al. |
| 5,514,182 A | 5/1996 | Shea |
| 5,531,748 A | 7/1996 | De la Caffiniere |
| 5,549,706 A | 8/1996 | McCarthy |
| 5,562,666 A | 10/1996 | Brumfield |
| 5,571,203 A | 11/1996 | Masini |
| 5,580,247 A | 12/1996 | Gittleman |
| 5,584,695 A | 12/1996 | Lal Sachdeva et al. |
| 5,591,233 A | 1/1997 | Kelman et al. |
| 5,593,451 A | 1/1997 | Averill et al. |
| 5,597,378 A | 1/1997 | Jervis |
| 5,624,445 A * | 4/1997 | Burke ............................ 606/89 |
| 5,645,600 A | 7/1997 | Bimman |
| 5,645,607 A | 7/1997 | Hickey |
| 5,653,765 A | 8/1997 | McTighe et al. |
| 5,697,932 A | 12/1997 | Smith et al. |
| 5,702,480 A | 12/1997 | Kropf et al. |
| 5,702,483 A | 12/1997 | Kwong |
| 5,713,902 A | 2/1998 | Friedl |
| 5,725,595 A * | 3/1998 | Gustilo ....................... 623/23.15 |
| 5,728,128 A | 3/1998 | Crickenberger et al. |
| 5,741,262 A | 4/1998 | Albrektsson et al. |
| 5,755,807 A * | 5/1998 | Anstaett et al. ............. 623/22.2 |
| 5,755,810 A | 5/1998 | Cunningham |
| 5,766,262 A | 6/1998 | Mikhail |
| 5,776,200 A | 7/1998 | Johnson et al. |
| 5,782,921 A | 7/1998 | Colleran et al. |
| 5,800,553 A | 9/1998 | Albrektsson et al. |
| 5,800,557 A | 9/1998 | Elhami |
| 5,817,098 A * | 10/1998 | Albrektsson et al. ........... 606/96 |

| | | | |
|---|---|---|---|
| 5,876,446 A | 3/1999 | Agrawal et al. | |
| 5,876,459 A * | 3/1999 | Powell | 623/23.15 |
| 5,888,206 A | 3/1999 | Lob et al. | |
| 5,888,208 A | 3/1999 | Ro | |
| 5,902,340 A * | 5/1999 | White et al. | 128/898 |
| 5,904,720 A * | 5/1999 | Farrar et al. | 623/22.15 |
| 5,928,235 A | 7/1999 | Friedl | |
| 5,931,871 A | 8/1999 | Baur et al. | |
| 5,961,555 A | 10/1999 | Huebner | |
| 5,980,575 A | 11/1999 | Albrektsson et al. | |
| 5,997,582 A | 12/1999 | Weiss | |
| 6,010,535 A | 1/2000 | Shah | |
| 6,045,555 A | 4/2000 | Smith et al. | |
| 6,059,830 A | 5/2000 | Lippincott, III et al. | |
| 6,074,424 A | 6/2000 | Perrone, Jr. et al. | |
| 6,102,953 A | 8/2000 | Huebner | |
| 6,142,998 A | 11/2000 | Smith et al. | |
| 6,165,177 A * | 12/2000 | Wilson et al. | 606/100 |
| 6,165,223 A | 12/2000 | Metzger et al. | |
| 6,168,627 B1 | 1/2001 | Huebner | |
| 6,168,828 B1 | 1/2001 | Chernyshov et al. | |
| 6,193,758 B1 | 2/2001 | Huebner | |
| 6,197,063 B1 | 3/2001 | Dews | |
| 6,197,065 B1 | 3/2001 | Martin et al. | |
| 6,214,052 B1 | 4/2001 | Burkinshaw | |
| 6,221,074 B1 | 4/2001 | Cole et al. | |
| 6,224,601 B1 | 5/2001 | Friedl | |
| 6,238,435 B1 * | 5/2001 | Meulink et al. | 623/22.12 |
| 6,248,112 B1 | 6/2001 | Gambale et al. | |
| 6,261,290 B1 | 7/2001 | Friedl | |
| 6,264,699 B1 * | 7/2001 | Noiles et al. | 623/23.23 |
| 6,277,082 B1 | 8/2001 | Gambale | |
| 6,284,002 B1 | 9/2001 | Sotereanos | |
| 6,309,395 B1 | 10/2001 | Smith et al. | |
| 6,330,845 B1 * | 12/2001 | Meulink | 81/462 |
| 6,371,991 B1 * | 4/2002 | Manasas et al. | 623/22.12 |
| 6,379,360 B1 | 4/2002 | Ackeret et al. | |
| 6,379,388 B1 | 4/2002 | Ensign et al. | |
| 6,409,730 B1 | 6/2002 | Green et al. | |
| 6,432,126 B1 | 8/2002 | Gambale et al. | |
| 6,432,141 B1 * | 8/2002 | Stocks et al. | 623/22.13 |
| 6,440,171 B1 | 8/2002 | Doubler et al. | |
| 6,458,092 B1 | 10/2002 | Gambale et al. | |
| 6,479,565 B1 | 11/2002 | Stanley | |
| 6,494,913 B1 | 12/2002 | Huebner | |
| 6,503,252 B2 | 1/2003 | Hansson | |
| 6,503,255 B1 * | 1/2003 | Albrektsson et al. | 606/89 |
| 6,508,841 B2 | 1/2003 | Martin et al. | |
| 6,517,541 B1 | 2/2003 | Sesic | |
| 6,607,561 B2 * | 8/2003 | Brannon | 623/23.11 |
| 6,616,697 B2 | 9/2003 | Sotereanos | |
| 6,620,170 B1 | 9/2003 | Ahern | |
| 6,648,889 B2 | 11/2003 | Bramlet et al. | |
| 6,656,187 B1 * | 12/2003 | Camino | 606/85 |
| 6,682,568 B2 | 1/2004 | Despres, III et al. | |
| 6,692,520 B1 | 2/2004 | Gambale et al. | |
| 6,695,850 B2 | 2/2004 | Diaz | |
| 6,695,883 B2 | 2/2004 | Crofford | |
| 6,699,293 B2 * | 3/2004 | White | 623/23.22 |
| 6,702,854 B1 * | 3/2004 | Cheal et al. | 623/22.42 |
| 6,706,072 B2 * | 3/2004 | Dwyer et al. | 623/22.42 |
| 6,709,425 B2 | 3/2004 | Gambale et al. | |
| 6,712,855 B2 | 3/2004 | Martin et al. | |
| 6,719,805 B1 | 4/2004 | Ahern | |
| 6,723,129 B2 * | 4/2004 | Dwyer et al. | 623/22.42 |
| 6,755,862 B2 | 6/2004 | Keynan | |
| 6,758,864 B2 * | 7/2004 | Storer et al. | 623/22.38 |
| 6,786,929 B2 | 9/2004 | Gambale et al. | |
| 6,802,858 B2 | 10/2004 | Gambale et al. | |
| 6,843,806 B2 | 1/2005 | Hayes, Jr. et al. | |
| 6,851,160 B2 | 2/2005 | Carver | |
| 6,866,683 B2 | 3/2005 | Gerbec et al. | |
| 6,875,239 B2 * | 4/2005 | Gerbec et al. | 623/23.15 |
| 6,887,276 B2 | 5/2005 | Gerbec et al. | |
| 6,902,583 B2 | 6/2005 | Gerbec et al. | |
| 6,905,502 B2 * | 6/2005 | Penenberg | 606/81 |
| 6,913,623 B1 | 7/2005 | Zhu | |
| 6,949,117 B2 | 9/2005 | Gambale et al. | |
| 6,976,999 B2 * | 12/2005 | Charlebois et al. | 623/16.11 |
| 6,988,784 B2 | 1/2006 | Silverbrook | |
| 6,991,656 B2 * | 1/2006 | Mears | 623/22.4 |
| 7,004,972 B2 * | 2/2006 | Yoon | 623/22.4 |
| 7,104,995 B2 | 9/2006 | Crofford | |
| 7,141,073 B2 | 11/2006 | May et al. | |
| 7,156,879 B1 * | 1/2007 | Albrektsson et al. | 623/23.14 |
| 7,179,297 B2 * | 2/2007 | McLean | 623/22.11 |
| 7,235,106 B2 * | 6/2007 | Daniels et al. | 623/22.42 |
| 7,468,078 B2 * | 12/2008 | Sederholm et al. | 623/22.42 |
| 7,572,294 B2 * | 8/2009 | Meridew et al. | 623/22.12 |
| 7,582,092 B2 * | 9/2009 | Jones et al. | 606/102 |
| 7,608,112 B1 | 10/2009 | Kuczynski et al. | |
| 7,695,521 B2 * | 4/2010 | Ely et al. | 623/22.21 |
| 7,799,029 B2 * | 9/2010 | Jones | 606/53 |
| 7,842,096 B2 * | 11/2010 | Fridshtand et al. | 623/23.35 |
| 7,850,690 B2 * | 12/2010 | Frigg et al. | 606/67 |
| 7,901,411 B2 * | 3/2011 | Frederick et al. | 606/102 |
| 8,029,573 B2 | 10/2011 | Podolsky | |
| 2001/0049559 A1 * | 12/2001 | Koo et al. | 623/17.16 |
| 2002/0004685 A1 * | 1/2002 | White | 623/23.15 |
| 2002/0007220 A1 * | 1/2002 | Gie et al. | 623/23.15 |
| 2002/0040244 A1 * | 4/2002 | Despres et al. | 623/22.15 |
| 2002/0049500 A1 * | 4/2002 | Draenert | 623/22.12 |
| 2002/0058999 A1 * | 5/2002 | Dwyer et al. | 623/22.42 |
| 2002/0072799 A1 | 6/2002 | Despres, III et al. | |
| 2002/0072802 A1 | 6/2002 | O'Neil et al. | |
| 2002/0103541 A1 | 8/2002 | Meyers et al. | |
| 2002/0120343 A1 * | 8/2002 | Doubler et al. | 623/22.42 |
| 2002/0133234 A1 * | 9/2002 | Sotereanos | 623/23.26 |
| 2002/0151984 A1 * | 10/2002 | White | 623/23.22 |
| 2003/0071819 A1 | 4/2003 | Kondo et al. | |
| 2003/0074079 A1 | 4/2003 | McTighe et al. | |
| 2003/0125808 A1 * | 7/2003 | Hunter et al. | 623/18.11 |
| 2003/0130741 A1 * | 7/2003 | McMinn | 623/23.14 |
| 2004/0054419 A1 | 3/2004 | Serra et al. | |
| 2004/0267373 A1 * | 12/2004 | Dwyer et al. | 623/22.12 |
| 2005/0149047 A1 * | 7/2005 | Parry et al. | 606/99 |
| 2006/0030947 A1 * | 2/2006 | Mears et al. | 623/22.11 |
| 2006/0173548 A1 * | 8/2006 | Auxepaules et al. | 623/22.12 |
| 2007/0078464 A1 * | 4/2007 | Jones et al. | 606/86 |
| 2007/0142921 A1 * | 6/2007 | Lewis et al. | 623/22.36 |
| 2007/0179568 A1 * | 8/2007 | Nycz et al. | 607/60 |
| 2007/0270846 A1 * | 11/2007 | Metzinger | 606/64 |
| 2007/0270847 A1 * | 11/2007 | Shaw | 606/65 |
| 2009/0093887 A1 * | 4/2009 | Walter et al. | 623/22.11 |
| 2009/0264885 A1 * | 10/2009 | Grant et al. | 606/66 |
| 2009/0287214 A1 * | 11/2009 | Yu | 606/64 |
| 2010/0228354 A1 * | 9/2010 | Ely et al. | 623/22.11 |
| 2011/0015752 A1 * | 1/2011 | Meridew | 623/22.24 |
| 2011/0035021 A1 * | 2/2011 | Bergin et al. | 623/22.42 |
| 2011/0046745 A1 * | 2/2011 | Daniels et al. | 623/22.42 |
| 2012/0022661 A1 * | 1/2012 | McLean | 623/22.15 |

FOREIGN PATENT DOCUMENTS

| | | |
|---|---|---|
| DE | 2854334 | 6/1980 |
| DE | 3205577 | 10/1982 |
| DE | 3340767 | 5/1985 |
| DE | 4031520 | 4/1992 |
| DE | 19505609 | 8/1996 |
| DE | 19610741 | 11/1997 |
| DE | 19852945 | 5/2000 |
| DE | 20007950 | 8/2000 |
| DE | 10120331 | 11/2002 |
| DE | 10223474 | 12/2003 |
| DE | 102005005657 | 8/2006 |
| EP | 0000549 | 2/1978 |
| EP | 0010527 | 4/1980 |
| EP | 0023608 | 2/1981 |
| EP | 0024008 | 2/1981 |
| EP | 0071242 | 2/1983 |
| EP | 0099167 | 1/1984 |
| EP | 0201407 | 11/1986 |
| EP | 0251583 | 1/1988 |
| EP | 0257118 | 3/1988 |
| EP | 0257359 | 3/1988 |
| EP | 0283706 | 9/1988 |
| EP | 0321170 | 6/1989 |
| EP | 0338774 | 10/1989 |
| EP | 0359457 | 3/1990 |

| | | |
|---|---|---|
| EP | 0376658 | 7/1990 |
| EP | 0382395 | 8/1990 |
| EP | 0399920 | 11/1990 |
| EP | 0433121 | 6/1991 |
| EP | 0441577 | 8/1991 |
| EP | 0464961 | 1/1992 |
| EP | 0495340 | 7/1992 |
| EP | 0556997 | 8/1993 |
| EP | 0567349 | 10/1993 |
| EP | 0586824 | 3/1994 |
| EP | 0714645 | 6/1996 |
| EP | 0832620 | 4/1998 |
| EP | 0878177 | 11/1998 |
| EP | 0913132 | 5/1999 |
| EP | 1004283 | 5/2000 |
| EP | 1132064 | 9/2001 |
| EP | 1240879 | 9/2002 |
| EP | 1344505 | 9/2003 |
| FR | 1099519 | 9/1955 |
| FR | 1122634 | 9/1956 |
| FR | 2183230 | 12/1973 |
| FR | 2225141 | 11/1974 |
| FR | 2575383 | 7/1986 |
| FR | 2629707 | 10/1989 |
| FR | 2639820 | 6/1990 |
| FR | 2646078 | 10/1990 |
| FR | 2651118 | 3/1991 |
| FR | 2674119 | 9/1992 |
| FR | 2705558 | 12/1994 |
| GB | 2209947 | 6/1989 |
| WO | WO 8505027 | 11/1985 |
| WO | WO 9308770 | 5/1993 |
| WO | WO 9417757 | 8/1994 |
| WO | WO 9613233 | 5/1996 |
| WO | WO 0072785 | 12/2000 |
| WO | WO 0149218 | 7/2001 |

* cited by examiner

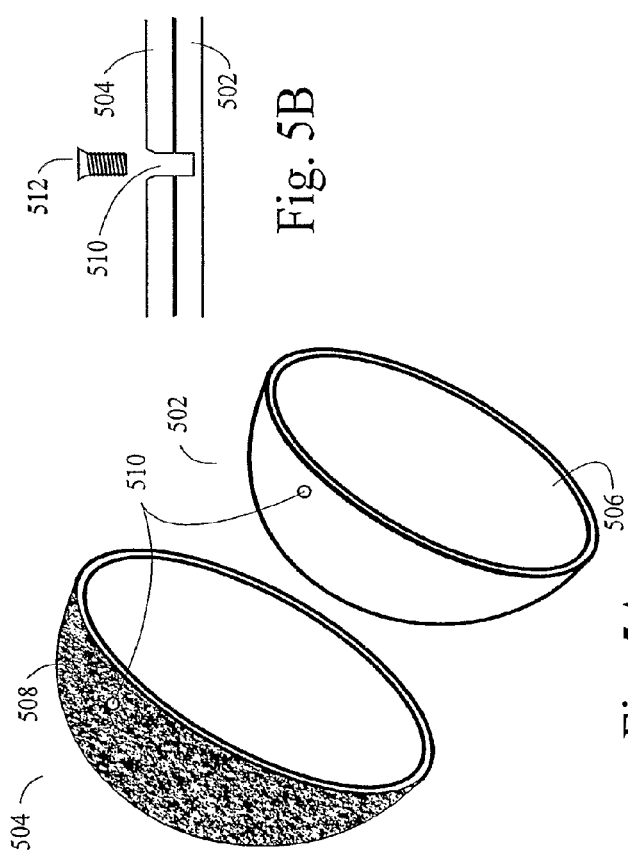
Fig. 5A
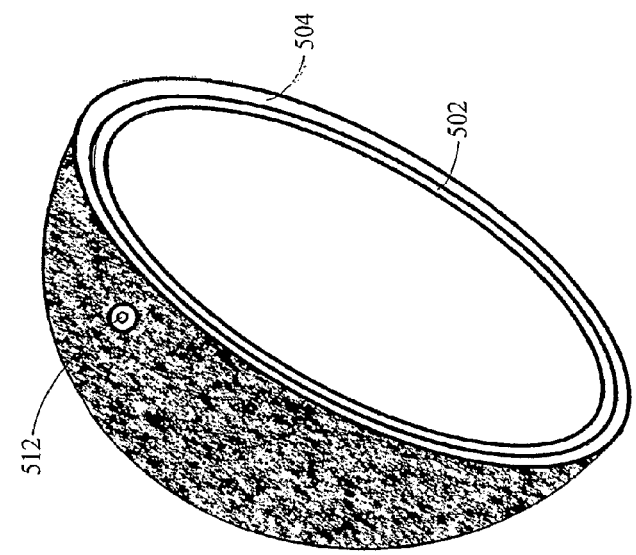
Fig. 5B
Fig. 5C
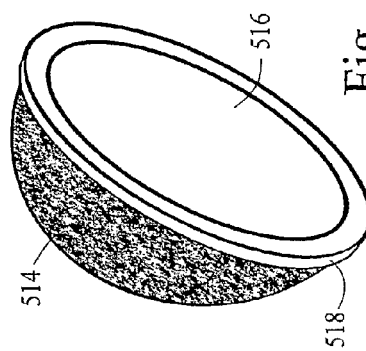
Fig. 5E
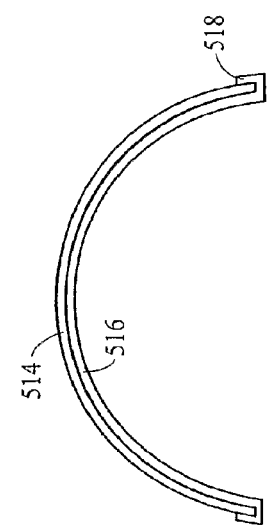
Fig. 5D

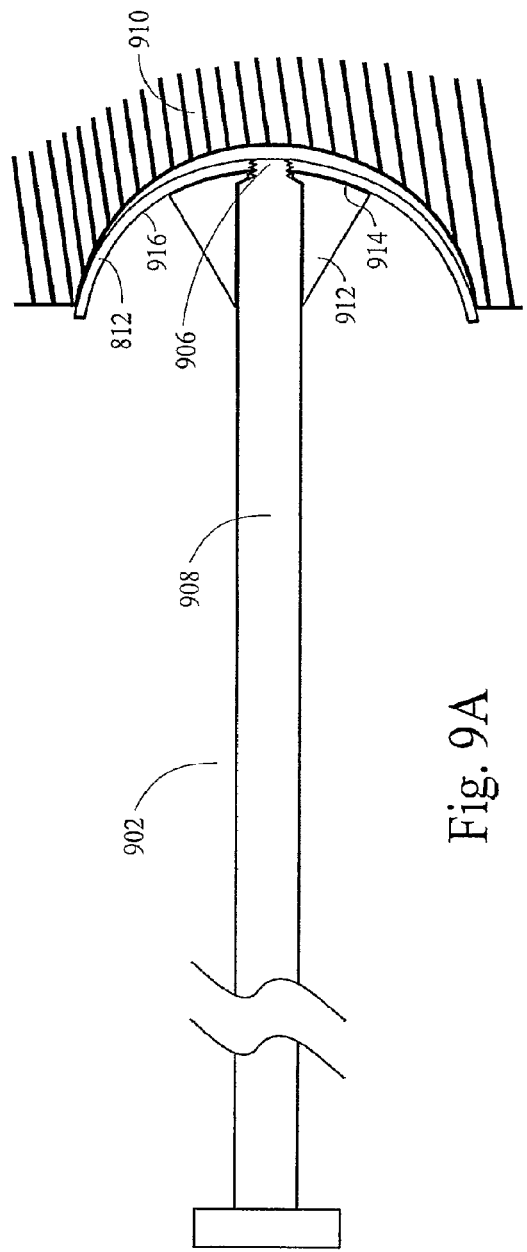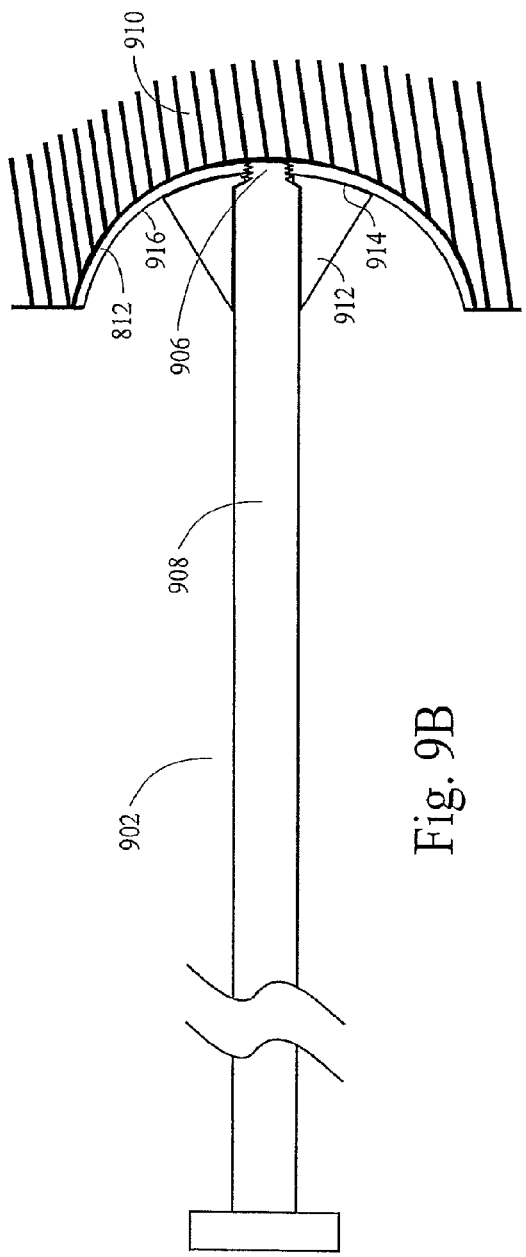

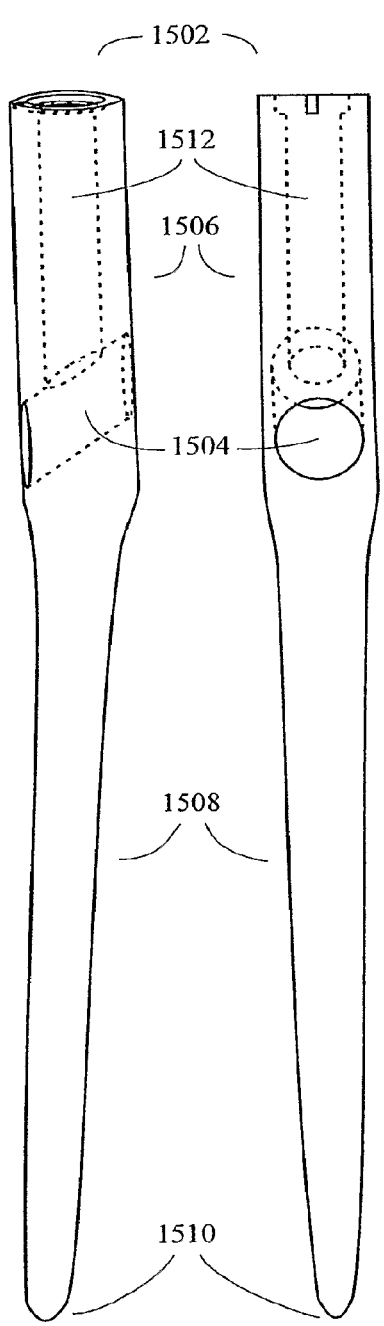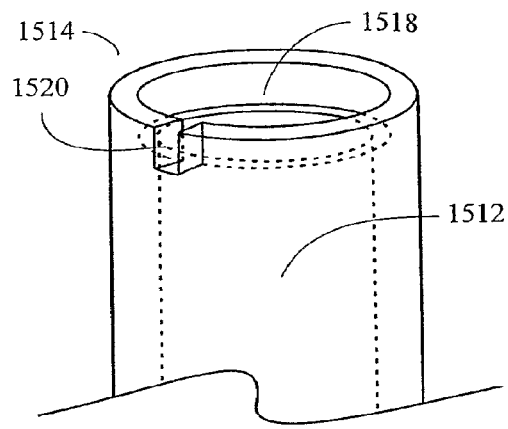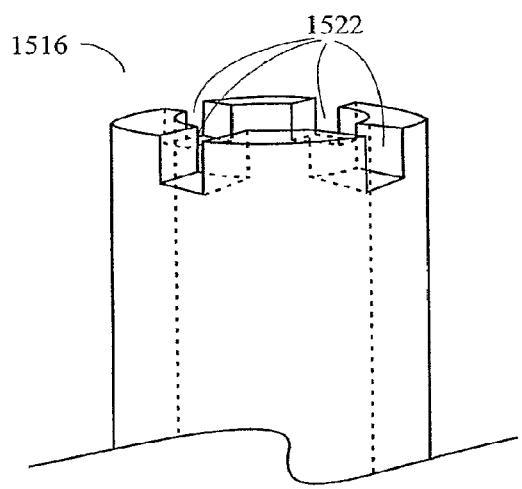
Fig. 15A    Fig. 15B
Fig. 15C
Fig. 15D

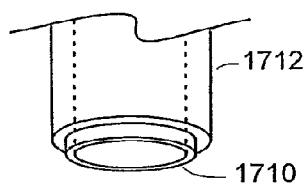
Fig. 17D
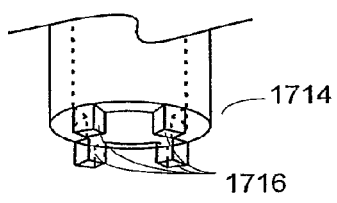
Fig. 17E
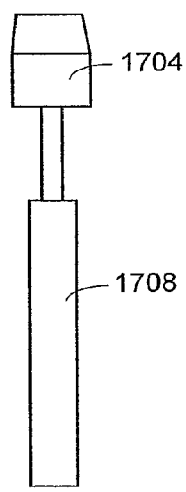
Fig. 17B
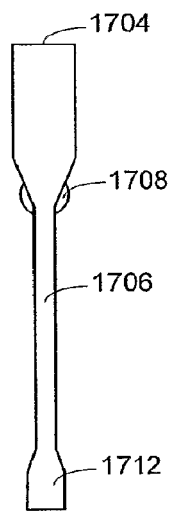
Fig. 17C
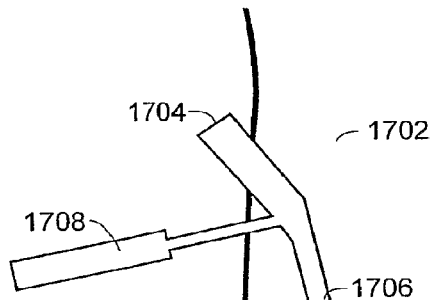
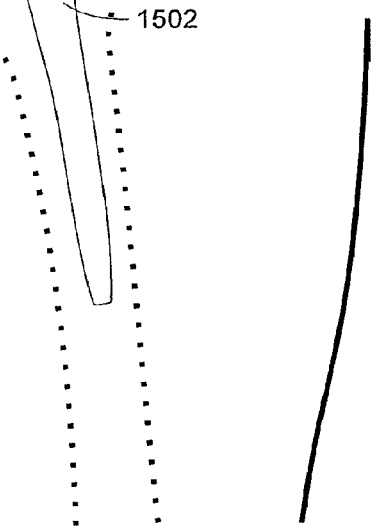
Fig. 17A

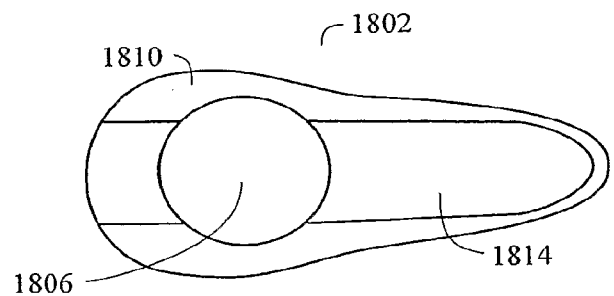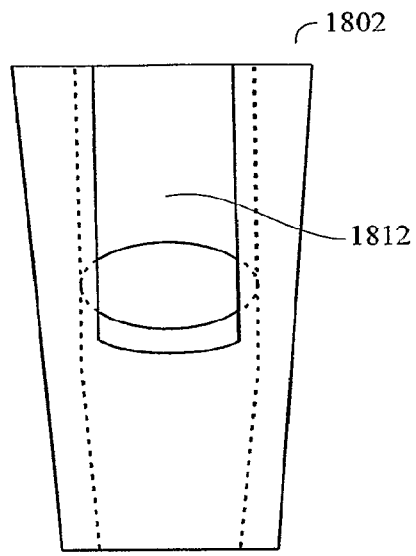
Fig. 18A
Fig. 18B
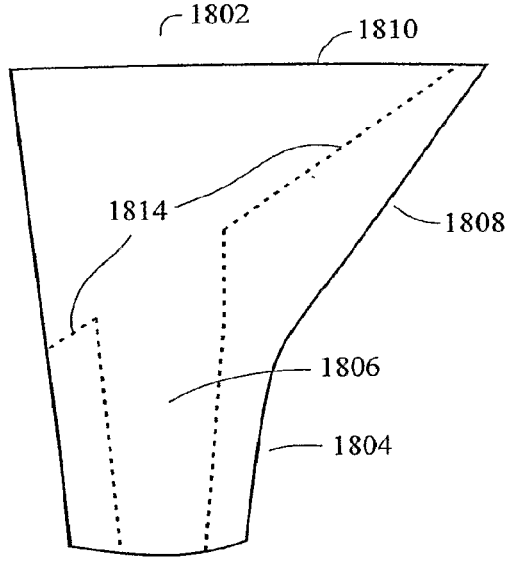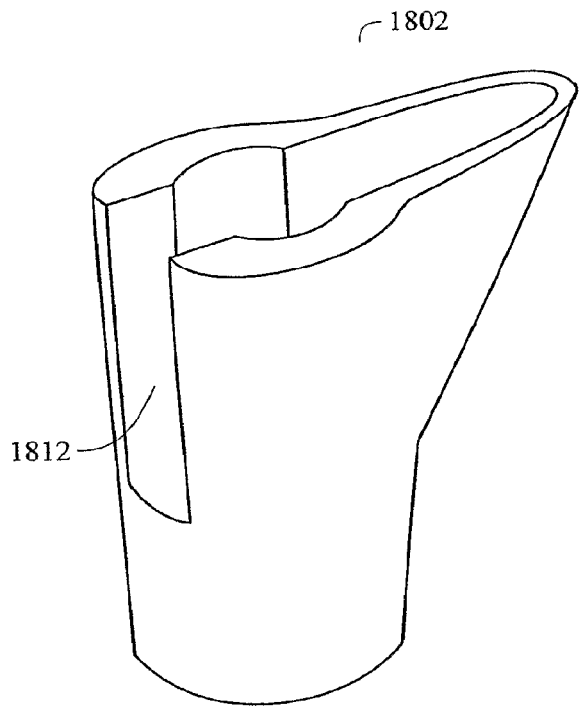
Fig. 18C
Fig. 18D

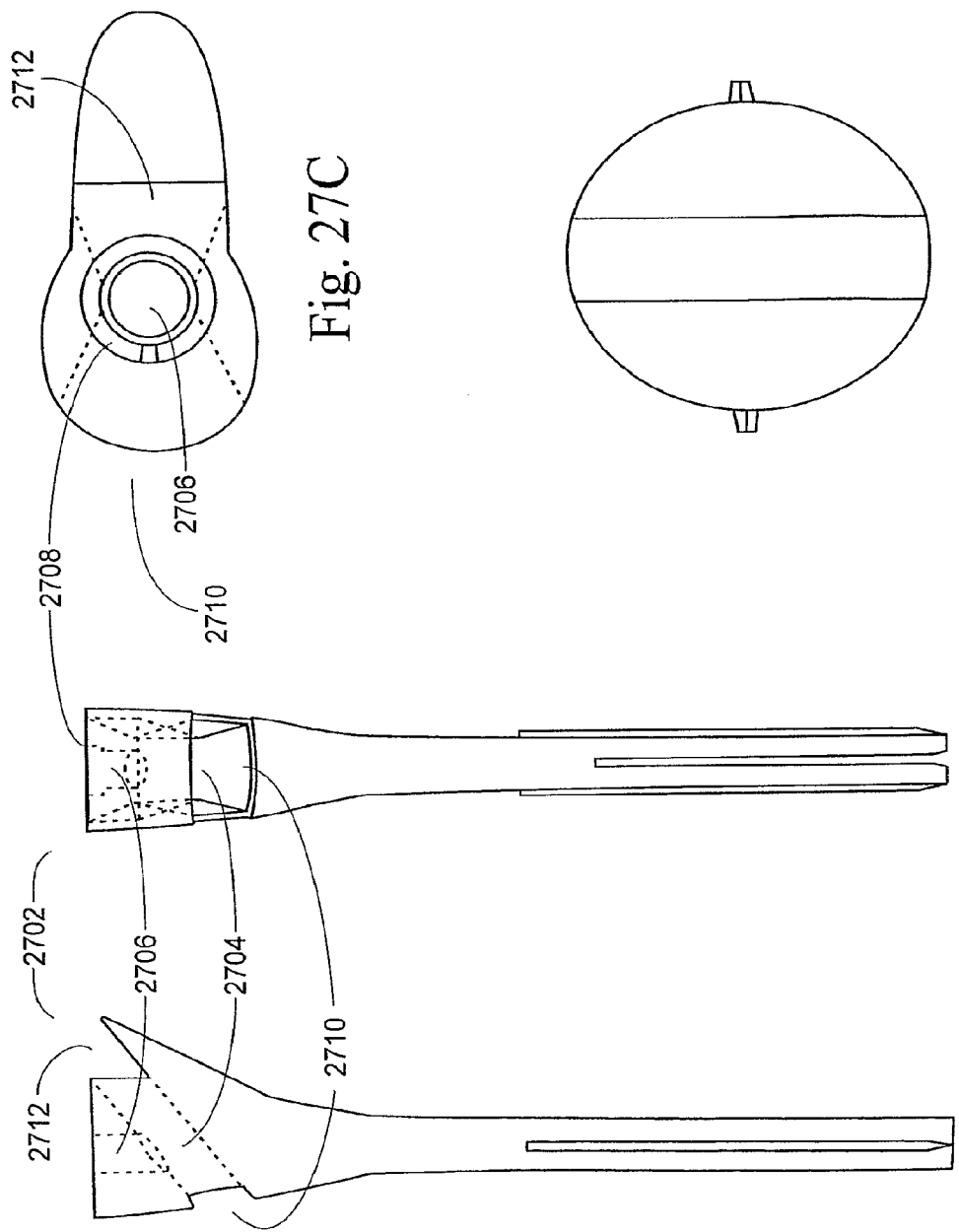

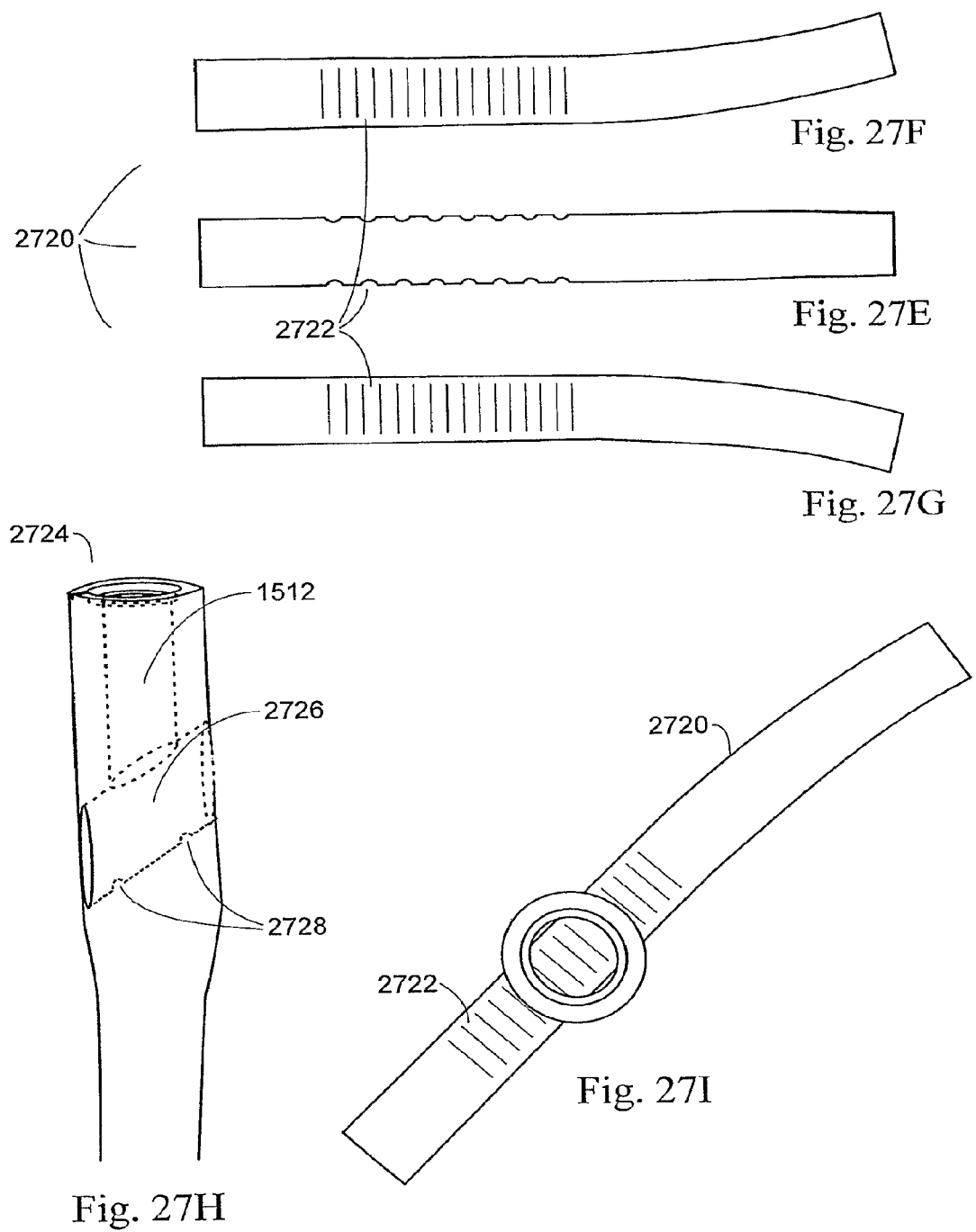

METHODS AND SYSTEMS FOR TOTAL HIP REPLACEMENT

RELATED APPLICATIONS

This U.S. patent application is a divisional of U.S. patent application Ser. No. 12/518,081, filed on Jun. 5, 2009, which is a U.S. National Phase under 35 U.S.C. §371 of International Application PCT/US2006/046795, filed on Dec. 7, 2006 and published in English on Jun. 12, 2008, each of which are incorporated herein by reference in their entirety.

BACKGROUND OF THE INVENTION

1. Field of the Invention

The present invention relates to medical methods and apparatus, and more particularly to a method and apparatus for minimally invasive total hip arthroplasty.

2. Description of the Related Art

Early methods and apparatus for performing total hip replacement required a relatively long incision and provided open visualization of the trochanteric region of the femur, the femoral head and the acetabulum. However, such techniques result in substantial dissection and disruption of muscles and tissues around the hip joint. The substantial disruption of the tissues creates risk of dislocation and requires many months for rehabilitation and healing.

Minimally invasive techniques for total hip replacement have also been described. See, e.g., U.S. Pat. Nos. 7,004,972, 6,991,656 or 6,695,850. As one example, information published by the American Academy of Orthopaedic Surgeons generally describes minimally invasive techniques that use a 3-6 centimeter incision and, as compared to traditional techniques, involve less splitting or detaching of muscles and tendons and less soft tissue dissection. However, such existing minimally invasive techniques still involve substantial disruption of the soft tissue envelope around the hip joint, including the tissue disruption required to create space in which to place and fit a prosthetic femoral neck and head between the femur and the acetabulum. Moreover, existing techniques have failed to adequately address the problem of numerous trial reductions and dislocations often required to achieve proper fit of the prosthetics which not only causes additional disruption to the tissues, but also consumes valuable time. There is a present need for methods and apparatus that provide for efficient total hip replacement while maintaining the integrity of the tissues proximate to the hip joint.

SUMMARY OF THE INVENTION

Once embodiment of the present inventions concerns a method of performing a total hip arthroplasty that comprises (1) surgically accessing an acetabulum, (2) preparing the acetabulum to receive a prosthetic acetabular cup, (3) seating the prosthetic acetabular cup in the prepared acetabulum, (4) fitting a prosthetic femoral head within the prosthetic acetabular cup, the prosthetic femoral head rotatable with respect to the prosthetic acetabular cup, (5) surgically accessing a femur, (6) preparing the femur to receive an intramedullary rod, the intramedullary rod having a neck bore, (7) inserting into the femur at least a portion of the intramedullary rod including the neck bore, (8) creating a femoral bore into the femur, the femoral bore defining a passage through the femur from a side of the femur opposite the acetabulum and through the neck bore in the inserted intramedullary rod, (9) inserting a head-engaging end of a prosthetic femoral neck into the femoral bore, through the neck bore in the inserted intramedullary rod to engage the prosthetic femoral head, and (10) joining the head-engaging end of the prosthetic femoral neck to the prosthetic femoral head. A preferred aspect of that embodiment further includes fixing the prosthetic femoral neck with respect to the inserted intramedullary rod. Additional advantage may be achieved in the embodiment wherein the fixed prosthetic femoral neck extends from a first point external to the femur and through the femur to a second point where it joins the prosthetic femoral head. Another preferred aspect of the present invention is one wherein the femoral bore is created before a natural femoral head is removed. A still further advantageous aspect of the present invention is one wherein at least one anterior incision provides surgical access to the acetabulum and to the femur. Another advantageous aspect of the present invention is one wherein a posterior incision provides surgical access to the femur. In a further preferred embodiment, the present invention includes removably fixing an alignment tool to the intramedullary rod, the alignment tool having a guide bore which, when the alignment tool is removably fixed to the intramedullary rod, is in alignment with the neck bore of the intramedullary rod, and advancing a drilling bit through the guide bore, through the side of the femur opposite the acetabulum, through the neck bore in the intramedullary rod in a direction toward the acetabulum.

This method may also derive advantage from an embodiment wherein the alignment tool further comprises a first fixation keyway and the intramedullary rod further comprises a second fixation keyway which removably interlocks with the first fixation keyway to facilitate removable fixation of the alignment tool to the intramedullary rod. The method may derive additional advantage from an embodiment wherein the diameters of the prosthetic acetabular cup and the prosthetic femoral head both exceed 50 millimeters. A further advantageous aspect of this method is one wherein the prosthetic acetabular cup includes at least one fixation bore and wherein seating the acetabular cup includes rotationally driving a fixation screw through the fixation bore to fix the prosthetic acetabular cup in a seated position within the prepared acetabulum. Another preferred aspect of the method is one wherein a hollow channel in the fixation screw is positioned to direct bodily fluid into a space between the prosthetic femoral head and the prosthetic acetabular cup. The method may derive additional benefit from an embodiment wherein at least part of the prosthetic acetabular cup is cobalt chromium. Still further advantage may be derived from an embodiment wherein the inner surface of the acetabular cup and the outer surface of the acetabular cup are made from different materials. Yet another preferred aspect of this embodiment is one wherein the insertion of at least a portion of the intramedullary rod comprises inserting a guide wire into the intramedullary canal of the femur. A still further preferred aspect of the present invention is one wherein a reamer is used in preparation of the acetabulum, the reamer having a reaming head and reaming shaft, the reaming head removable from the reaming shaft, the reaming head without the reaming shaft positioned at the acetabulum through the acetabular surgical access, the reaming shaft positioned through a second surgical access to engage the positioned reaming head. Additional benefit may be derived from this aspect in an embodiment of the method wherein the reaming shaft is positioned through the femoral bore to engage the positioned reaming head. Still further benefit may be derived from an embodiment of the method wherein an impactor is used in seating prosthetic acetabular cup in the acetabulum, the impactor having an impactor head and an impactor shaft, the impactor head removable from the impactor shaft, the impactor head without the impactor shaft positioned through the acetabular surgical access to engage the prosthetic acetabular cup, the impactor shaft positioned through a second surgical access to engage the positioned impactor head. Additional benefit from the method may be derived from an embodiment wherein the impactor shaft is positioned through the femoral bore to engage the positioned impactor head.

Another method of performing a total hip arthroplasty in accordance with the present invention comprises (1) surgically accessing an acetabulum and preparing it to receive a prosthetic acetabular cup and prosthetic femoral head, (2) seating the prosthetic acetabular cup and prosthetic femoral head, the prosthetic femoral head rotatable within the prosthetic acetabular cup, (3) surgically accessing a femur and preparing it to receive a support sleeve, the support sleeve comprising a rod bore and a neck passage, (4) seating the support sleeve into a trochanteric region of the femur, (5) inserting an intramedullary rod into the femur and through the rod bore of the support sleeve, the diameter of the rod bore configured to receive and hold a proximal region of the intramedullary rod while a distal stem of the intramedullary rod extends deeper into the femoral canal, the intramedullary rod comprising a neck bore aligned with the neck slot of the support sleeve, (6) inserting a prosthetic femoral neck from a position along a side of a patient's body, through a first side of the femur, through the neck passage and the neck bore to fixedly engage the prosthetic femoral head, and (7) fixing the prosthetic femoral neck with respect to the intramedullary rod to thereby position the femur to usefully approximate normal rotational capacity with respect to the acetabulum. A preferred aspect of this embodiment is one wherein the prosthetic femoral head is rotatably fixed within the prosthetic acetabular cup prior to surgically accessing the acetabulum. Another preferred aspect of this embodiment is one wherein bone-engaging walls of the support sleeve comprise a plurality of planar surfaces substantially perpendicular to the femoral canal. A still further preferred aspect of this embodiment is one wherein the diameters of the prosthetic acetabular cup and the prosthetic femoral head both exceed 50 millimeters. Additional advantage may be derived from an aspect of the embodiment wherein the outer surface of the prosthetic acetabular cup includes irregularities penetrable by new acetabular bone growth. Another preferred aspect of this embodiment is one wherein the outer surface of the prosthetic acetabular cup includes protrusions facilitating seating within the prepared acetabulum. Yet another preferred aspect of this embodiment is one wherein fixing the prosthetic femoral neck with respect to the intramedullary rod comprises rotationally driving a threaded fixation bolt into a threaded fixation bore in the intramedullary rod to exert a fixation force upon the prosthetic femoral neck, the threaded fixation bore perpendicular to and connecting with the neck bore. An additional preferred aspect of this embodiment is one wherein the fixation force upon the prosthetic femoral neck forces one or more ridges in the neck bore to engage one or more grooves formed in the prosthetic femoral neck.

One embodiment of an apparatus for total hip replacement in accordance with the present invention comprises (1) a prosthetic femoral head comprising a partially spherical head portion configured to fit rotatably within a prosthetic acetabular cup seated in an acetabulum, the prosthetic femoral head also comprising a neck engagement portion configured to fixedly join a prosthetic femoral neck, (2) an intramedullary rod configured to be inserted within a femur such that at least a portion of a proximal end of the intramedullary rod is positioned within a trochanteric region of the femur and a distal end of the intramedullary rod is positioned deeper in the femur, the intramedullary rod including a lateral bore, and (3) a prosthetic femoral neck having a head engagement end configured to fixedly join the neck engagement portion of the prosthetic femoral head, the prosthetic femoral neck configured to be advanced from a position along a side of a patient's body, through a side of the femur opposite the acetabulum, and through the lateral bore of the intramedullary rod such that the head engagement end of the prosthetic femoral neck fixedly joins the neck engagement portion of the prosthetic femoral head while a portion of the prosthetic femoral neck occupies the lateral bore. A preferred aspect of this embodiment is one wherein the intramedullary rod includes a threaded neck fixation bore extending from the proximal end of the intramedullary rod into the lateral bore, and wherein a threaded fixation screw removably tightened into the neck fixation bore fixes the prosthetic femoral neck relative to the intramedullary rod in a position in which the head engagement end of the prosthetic femoral neck fixedly joins the neck engagement portion of the prosthetic femoral head. Another preferred aspect of this embodiment is one wherein at least a shaft portion of the prosthetic femoral neck has a non-circular cross-section. A still further preferred aspect of this embodiment is one wherein a shaft portion of the prosthetic femoral neck is curved. Yet another preferred aspect of this embodiment is one wherein the diameter of the partially spherical head portion of the prosthetic femoral head is at least 50 millimeters. Additional advantage may be derived from an embodiment this apparatus wherein the distal end of the intramedullary rod comprises at least two prongs. A preferred aspect of this embodiment is one wherein an outer bone-engaging surface of the distal end of the intramedullary rod is configured to include at least one flute. An additional preferred aspect of this embodiment is one that further comprises a support sleeve adapted to be seated in the trochanteric region of the femur, the support sleeve including a rod bore and a neck passage, the rod bore configured to hold a portion of the proximal end of the intramedullary rod while the distal end of the intramedullary rod is positioned deeper in the femur such that the neck passage is aligned with the lateral bore of the intramedullary rod to accommodate advancement of the prosthetic femoral neck through both the neck passage and the lateral bore. Yet another preferred aspect of the embodiment is one wherein fixation ridges formed on a surface defining, at least in part, the neck passage engage the prosthetic femoral neck to resist movement of the prosthetic femoral neck within the neck passage. A still further preferred aspect of the embodiment is one wherein a shaft portion of the prosthetic femoral neck is curved and wherein at least one fixation groove is formed in both top and bottom sides of the prosthetic femoral neck. Additional advantage may be derived from an embodiment of the apparatus further comprising a neck cover configured to connect to the support sleeve to maintain separation between bodily tissues and a portion of the prosthetic femoral neck. A preferred aspect of this embodiment is one wherein respective surfaces of the lateral bore and the prosthetic femoral neck are configured to resist movement of the prosthetic femoral neck within the lateral bore. Still further advantage may be derived from an embodiment of the apparatus further comprising a prosthetic acetabular cup configured for seating in an acetabulum. A preferred aspect of that embodiment is one wherein the prosthetic acetabular cup is seated using an impactor comprising an impaction head with a convex impaction surface configured to nondestructively engage a portion of a concave surface of the prosthetic acetabular cup. Another preferred aspect of that embodiment is one wherein one or more protrusions on the outer surface of the prosthetic acetabular cup penetrate into acetabular bone when the prosthetic acetabular cup is seated in the acetabulum.

Another method for total hip arthroplasty in accordance with the present invention is one that comprises (1) fixing a prosthetic femoral head in a position rotatable with respect to an acetabulum, (2) creating a bore in a femur from a side of the femur opposite the acetabulum and extending in a direction toward the acetabulum, (3) joining an end of a prosthetic femoral neck to the prosthetic femoral head after advancing the end of the prosthetic femoral neck into the bore to engage the prosthetic femoral head, and (4) fixing the position of the prosthetic femoral neck with respect to the femur.

In addition, one embodiment for a system for total hip arthroplasty in accordance with the present invention comprises (1) means for fixing a prosthetic femoral head in a position rotatable with respect to an acetabulum, (2) means for creating a bore in a femur from a side of the femur opposite the acetabulum and extending in a direction toward the acetabulum, (3) means for joining an end of a prosthetic femoral neck to the prosthetic femoral head after advancing the end of the prosthetic femoral neck into the bore to engage the prosthetic femoral head, and (4) means for fixing the position of the prosthetic femoral neck with respect to the femur.

These and other embodiments of the present invention are disclosed and described below. It will be appreciated that other embodiments and all substantial equivalents are within the scope of the inventions.

BRIEF DESCRIPTION OF THE DRAWINGS

FIG. 5A illustrates a representation of an inner and an outer portion of a two-piece prosthetic cup with aligned holes used to join the two pieces in accordance with one embodiment of the present invention;

FIG. 5B illustrates a representation of aligned holes formed in walls of inner and outer cup portions of a two-piece prosthetic cup and a screw to be inserted through the holes to fix the cup portions relative to each other in accordance with one embodiment of the present invention;

FIG. 5C illustrates a two-piece prosthetic cup in accordance with one embodiment of the present invention;

FIG. 5D illustrates a cross-sectional view of an embodiment of a two-piece prosthetic cup in accordance with one embodiment of the present invention wherein the two pieces are joined by a lip formed into the rim of the inner cup;

FIG. 5E illustrates a two-piece prosthetic cup in accordance with an embodiment of the present invention wherein the two pieces are joined by a lip formed into the rim of an inner cup portion;

FIG. 9A illustrates a representation of an impactor tool joined to a prosthetic acetabular cup in position for impacting in accordance with an embodiment of the present invention;

FIG. 9B illustrates a representation of an impactor tool joined to a prosthetic acetabular cup impacted into an acetabulum in accordance with an embodiment of the present invention;

FIG. 15A illustrates a representation of a three-dimensional side view of an intramedullary rod with a femoral neck bore in accordance with an embodiment of the present invention;

FIG. 15B illustrates a representation of a three-dimensional front view of an intramedullary rod with a femoral neck bore in accordance with an embodiment of the present invention;

FIG. 15C illustrates a representation of a fixation keyway formed in an end of an intramedullary rod in accordance with an embodiment of the present invention;

FIG. 15D illustrates a representation of a fixation keyway formed in an end of an intramedullary rod in accordance with another embodiment of the present invention;

FIG. 17A illustrates a representation of a side view of a driving tool engaged with an intramedullary rod to be driven into a femoral canal in accordance with an embodiment of the present invention;

FIG. 17B illustrates a representation of a rear view of a driving tool in accordance with an embodiment of the present invention;

FIG. 17C illustrates a representation of a top down view of a driving tool in accordance with an embodiment of the present invention;

FIG. 17D illustrates a representation of a fixation keyway in an end of a driving tool in accordance with an embodiment of the present invention;

FIG. 17E illustrates a representation of a fixation keyway in an end of a driving tool in accordance with another embodiment of the present invention;

FIG. 18A illustrates a representation of a top down view of a support sleeve for an intramedullary rod in accordance with an embodiment of the present invention;

FIG. 18B illustrates a representation of a rear view of a support sleeve for an intramedullary rod in accordance with an embodiment of the present invention;

FIG. 18C illustrates a representation of a side view of a support sleeve for an intramedullary rod in accordance with an embodiment of the present invention;

FIG. 18D illustrates a representation of a perspective view of a support sleeve for an intramedullary rod in accordance with an embodiment of the present invention;

FIG. 27A illustrates a representation of a side view of an intramedullary rod with proximal femoral support structure in accordance with an embodiment of the present invention;

FIG. 27B illustrates a representation of a front view of an intramedullary rod with proximal femoral support structure in accordance with an embodiment of the present invention;

FIG. 27C illustrates a representation of a top down view of an intramedullary rod with proximal femoral support structure in accordance with an embodiment of the present invention;

FIG. 27D illustrates a representation of a bottom up view of a split and fluted distal end of an intramedullary rod with proximal femoral support structure in accordance with an embodiment of the present invention;

FIG. 27E illustrates a representation of a side view of a prosthetic femoral neck having preconfigured ridges for fixation within a neck bore of an intramedullary rod in accordance with an embodiment of the present invention;

FIG. 27F illustrates a representation of a top down view of a prosthetic femoral neck having preconfigured ridges for fixation within a neck bore of an intramedullary rod and a curved prosthetic femoral neck shaft in accordance with an embodiment of the present invention;

FIG. 27G illustrates a representation of a bottom up view of a prosthetic femoral neck having preconfigured ridges for fixation within a neck bore of an intramedullary rod and a curved prosthetic femoral neck shaft in accordance with an embodiment of the present invention;

FIG. 27H illustrates a representation of an upper portion of an intramedullary rod showing a neck bore with gripping ridges formed therein for fixedly engaging ridges of a prosthetic femoral neck inserted therethrough in accordance with an embodiment of the present invention;

FIG. 27I illustrates a representation of a top down view of an intramedullary rod having a neck bore and illustrating a representation of a prosthetic femoral neck inserted through the neck bore in accordance with an embodiment of the present invention;

DETAILED DESCRIPTION OF THE PREFERRED EMBODIMENT

In accordance with one embodiment of a method in accordance with the present invention, a patient is placed in the supine position on a standard operating table. As is known, specialized viewing tables and/or viewing systems may be used as desired, and the present invention is not limited by a particular type of table or viewing system.

Figure 1:
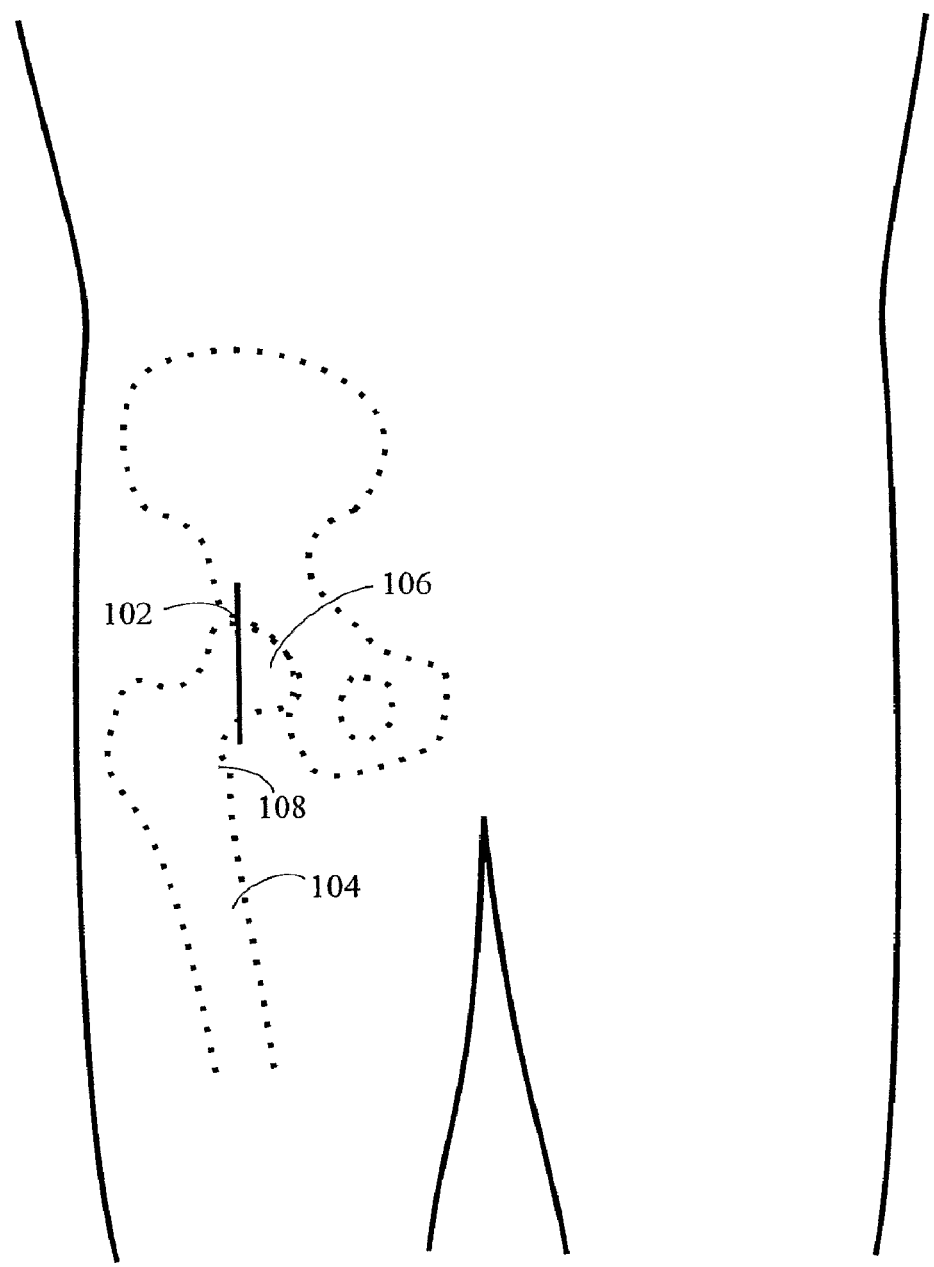
FIG. 1 illustrates a representation of an initial incision in accordance with one embodiment of the present invention.

FIG. 1 illustrates a representation of an initial incision 102 in accordance with one embodiment of the present invention. An anterior approach that may be used in this embodiment is to perform, with the patient in supine position, a portion of a Smith-Peterson approach (Hoppenfeld and deBoer, Surgical Exposures in Orthopaedics—The Anatomic Approach, 1984) making approximately a 2-3 cm incision 102 located preferably along a line that is approximately parallel to the length of the femur 104 and positioned approximately over the femoral head 106, with the distal (toward the patient's foot) extent of the line extending approximately to a point lateral to the lesser trochanter 108. This approach provides safe access to the hip joint by exploiting the internervous plane between the sartorius and the tensor fasciae latae and avoiding the femoral and superior gluteal nerves. This internervous plane is developed by known methods. The incision may advantageously be extended in either direction as needed.

Figure 2:
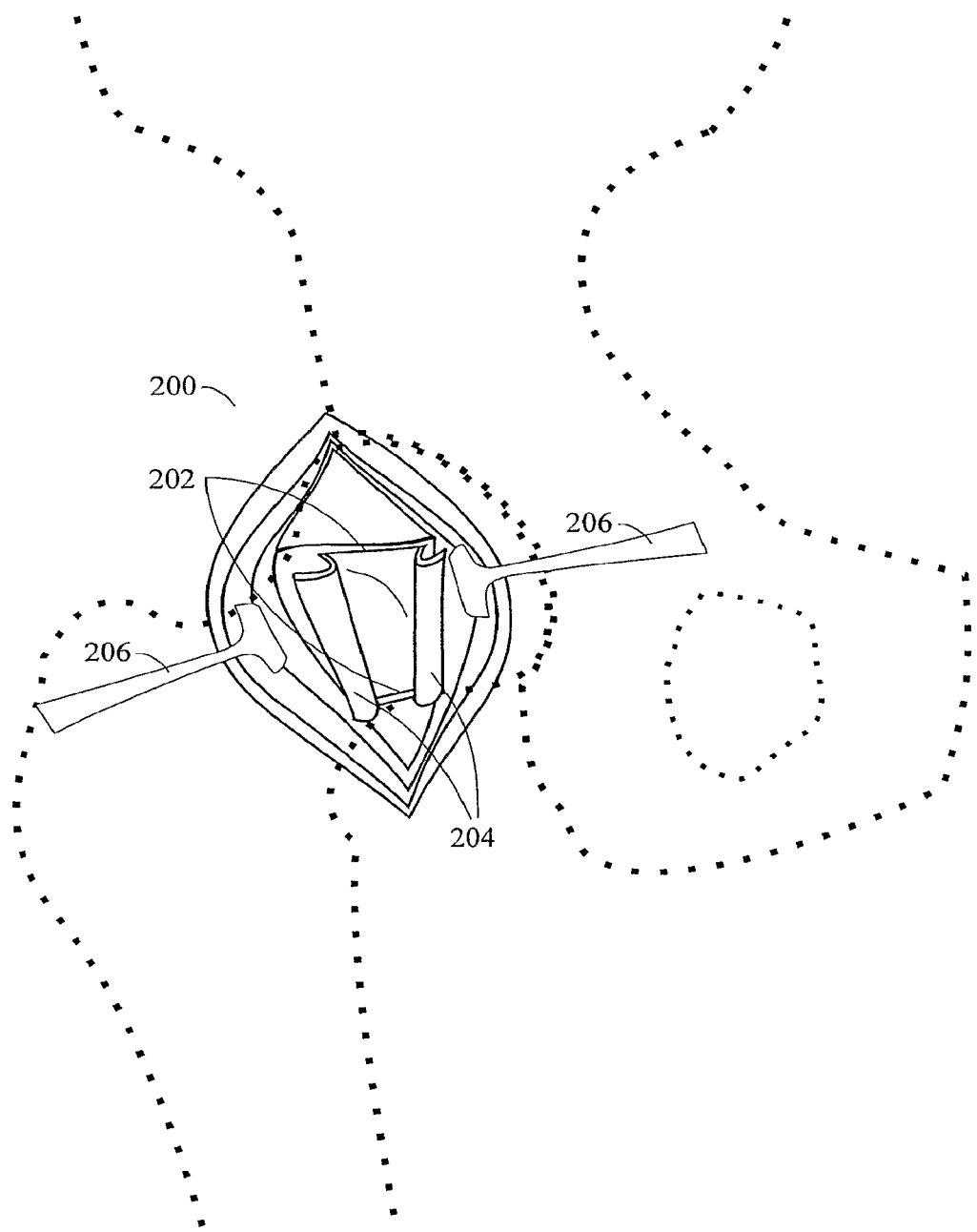
FIG. 2 illustrates a representation of a surgical access to a hip joint capsule in accordance with one embodiment of the present invention.

Also, in accordance with known technique, the deeper internervous plane between the rectus femoris and the gluteus medius is developed. With the internervous planes developed, and with retraction of muscles and tissue, the hip joint capsule may be accessed and visualized. FIG. 2 illustrates a representation of a surgical access 200 to a hip joint capsule in accordance with one embodiment of the present invention.

The hip joint capsule itself may then be incised, in one embodiment of the present invention, from approximately the mid-point of the femoral head and extending along the axis of the femoral neck to approximately a point on a line between the greater and lesser trochanters.

Secondary incisions 202 may then be made to form flaps in the hip joint capsule walls that may be retracted to access the femoral neck, the femoral head and the acetabulum. In accordance with known technique, an "H" type incision may be used to create the capsular flaps 204, which may then be held open by suture or retractors 206 to expose the femoral neck.

It will be appreciated that other surgical approaches may be used to access the femoral neck and acetabulum regions, and the present invention is not limited by any particular surgical approach.

Figure 3C:
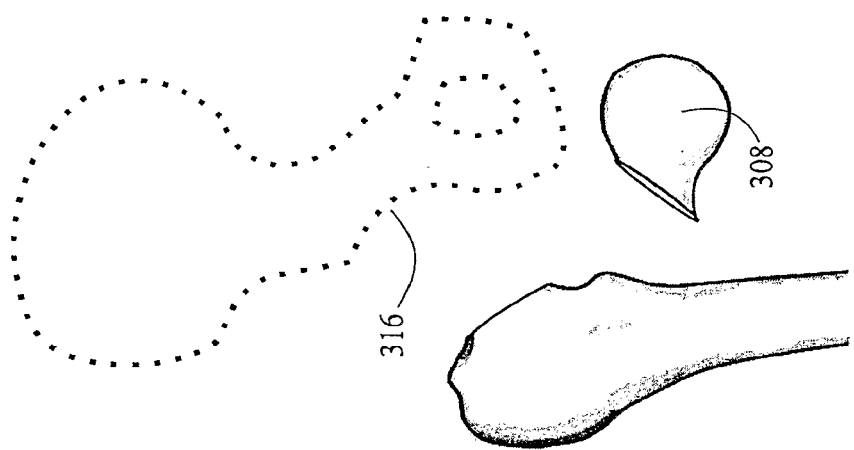
FIG. 3C illustrates a representation of removal of a femoral head in accordance with one embodiment of the present invention.

With the femoral neck accessed, both it and the femoral head may then be excised. A cutting tool, such as, for example, an oscillating saw, may be used to make cuts in the femoral neck. FIG. 3A illustrates a representation of cut lines 302, 304 in a femoral neck 306 in accordance with one embodiment of the present invention.

Preferably, two cut lines are defined: the first cut line 302 begins approximately at the point where the femoral neck 306 joins the greater trochanter and extends across the femoral neck 306 to end approximately at a point about 1.5 cm posterior to the lesser trochanter 310; and the second cut line 304 begins approximately at the point where the femoral neck 306 joins the femoral head 308 and extends across the femoral neck 306 to end at the same end point as the first cut line 302, namely, at the point approximately 1.5 cm posterior to the lesser trochanter 310.

Figure 3B:
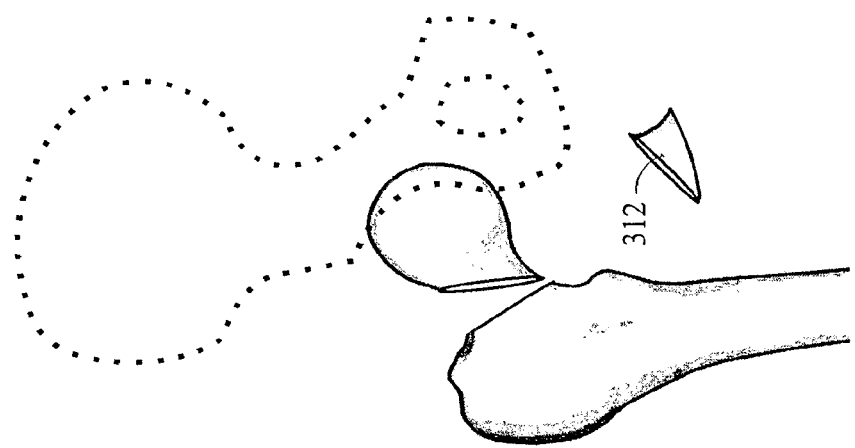
FIG. 3B illustrates a representation of removal of a portion of a femoral neck in accordance with one embodiment of the present invention.
Figure 3A:
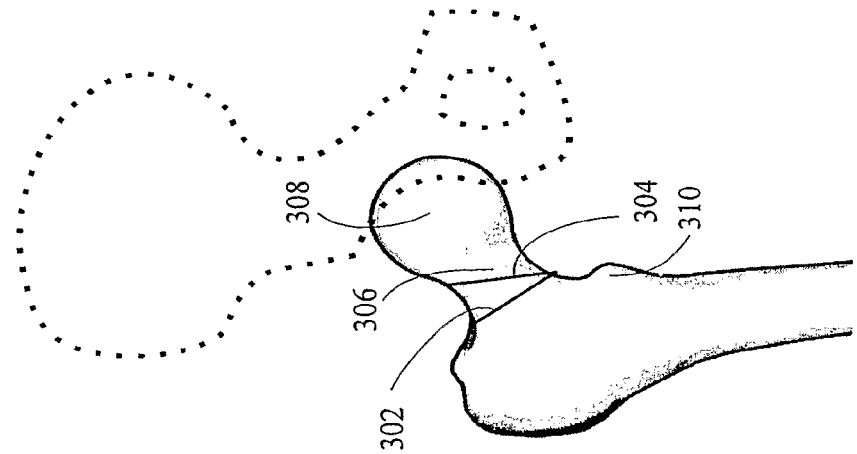
FIG. 3A illustrates a representation of cut lines in a femoral neck in accordance with one embodiment of the present invention.

FIG. 3B illustrates a representation of removal of a portion of a femoral neck in accordance with one embodiment of the present invention. It will be appreciated that two cuts in the femoral neck made along the first and second cut lines 302, 304, define and loosen a wedge-shaped piece 312 of the femoral neck 306, which piece may then be removed. It will be further appreciated that different cut lines may be used to loosen and remove different portions of the femoral neck 306 without departing from the present invention.

With the wedge-shaped piece 312 of the femoral neck 306 removed, the femoral head 308 may be accessed for removal. FIG. 3C illustrates a representation of removal of a femoral head 308 in accordance with one embodiment of the present invention.

After adjusting retractors to better access and visualize the femoral head 308 and acetabulum 316, and in accordance with known technique, a circular cutting tool may be inserted behind the femoral head 308 and may be used to sever the ligamentum teres, substantially freeing the femoral head 308 for removal using a corkscrew or an appropriately-sized forceps. Any difficulty in removing the femoral head 308 through the surgical access may easily be overcome by morselizing the femoral head 308 and removing the morsels and debris.

After confirming complete removal of the femoral head 308 and related debris, attention is then turned to preparing the acetabulum to receive a prosthetic acetabular cup. The present invention is not limited by the size of a prosthetic femoral head or the size of a prosthetic acetabular cup.

Figure 4A:
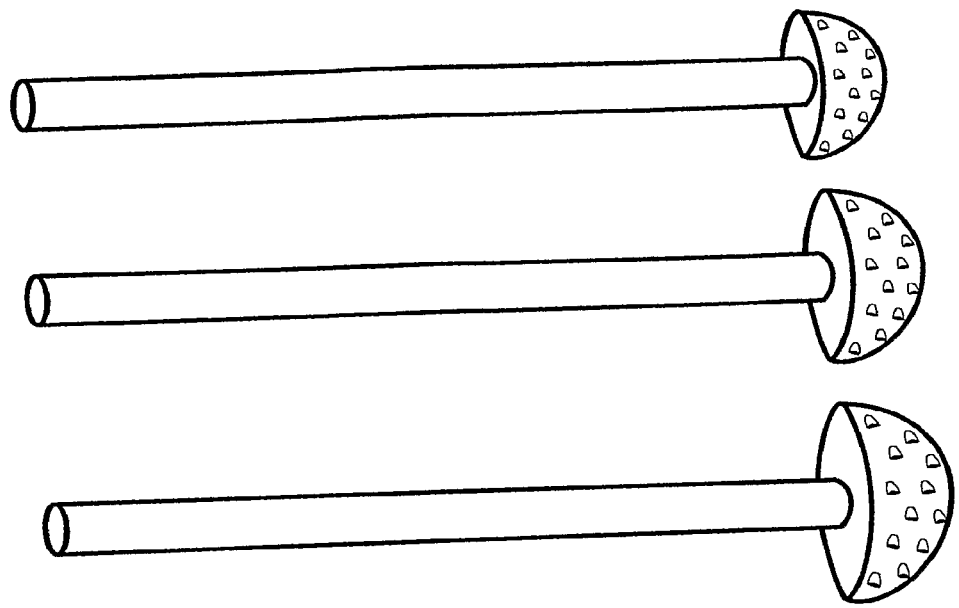
FIG. 4A illustrates a representation of a series of reamer tools stepped in size.

The acetabulum is prepared using known techniques, including removal of tissue from the cotyloid fossa and trimming of the labrum as needed. Osteophytes, cysts and the like may be removed from the area. The acetabulum may be progressively reamed using a series of standard reamers having progressively larger cutting heads designed to remove bone and to create a hemispherical concavity in the healthy subchondral bleeding bone that remains. FIG. 4A illustrates a representation of a series of reamer tools stepped in size. It will be appreciated that numerous reaming tools exist for reaming an acetabulum to receive a prosthetic acetabular cup, and the present invention is not limited by any particular reaming tool or any particular form of cutting head on a reaming tool.

Figure 4B:
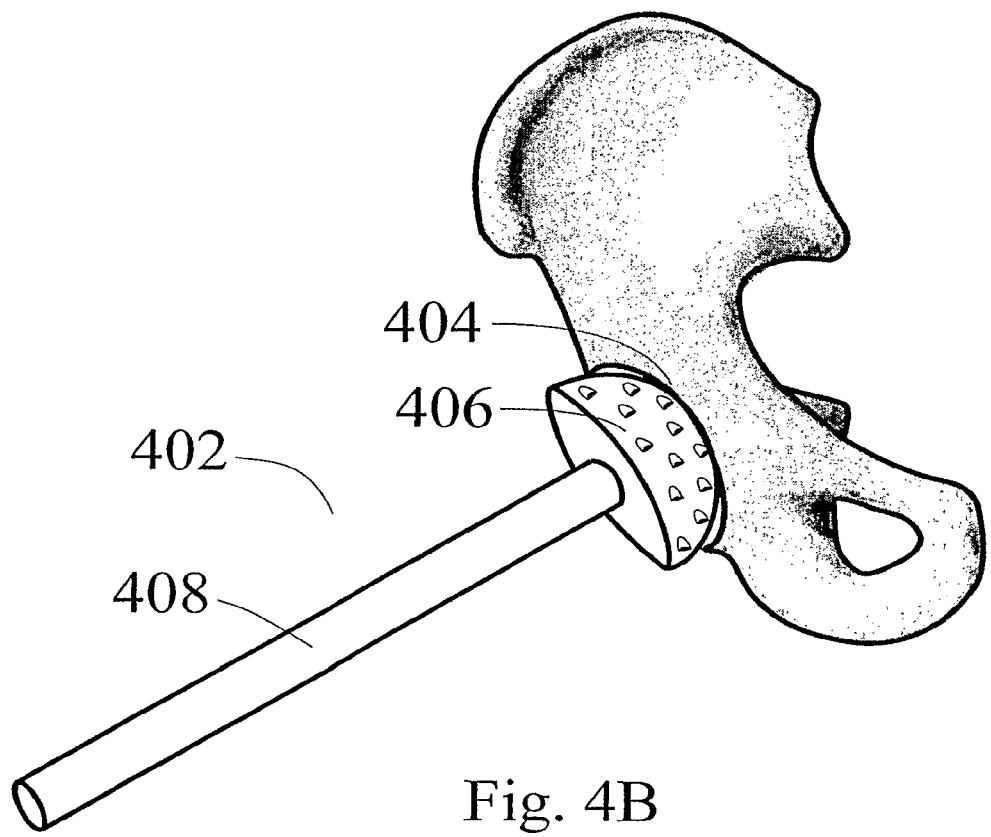
FIG. 4B illustrates a representation of reaming of an acetabulum in accordance with one embodiment of the present invention.

FIG. 4B illustrates a representation of reaming of an acetabulum 404 in accordance with one embodiment of the present invention. A reamer 402 comprises a reamer head 406 and a reamer shaft 408. The reamer head 406 may be removable from the reamer shaft 408, such as, for example, by spiral threads formed in the non-engaging side of the reamer head 406 which engage spiral threads formed into the end of the reamer shaft 408 when the reamer head 406 is rotated in the direction opposite from that in which it is configured to remove material from an acetabulum. The reamer head 406, as will be readily appreciated, may be configured to remove material from an acetabulum to create a roughly hemispherical void. The reamer 402 may be oriented at approximately 30 degrees of anteversion to achieve a desired degree of acetabular cup anteversion. The reamer 402 may also preferably be oriented to achieve a desirable abduction angle of approximately 45 degrees. Angles of anteversion and abduction may be adjusted in view of patient-specific anatomy. Templates and radiographs may be used to assist in orienting and sizing, and endoscopic or fluoroscopic imaging may assist the use of progressively larger reamers to achieve the properly-sized receiving area in the acetabulum 404. As will be readily appreciated, the acetabulum 404 is carefully under-reamed about 1-2 mm to achieve the best fit during impacting of the prosthetic acetabular cup. In an embodiment including the use of a prosthetic acetabular cup of 58 mm diameter, the acetabulum 404 may be reamed to form a hemispherical concavity of approximately 56-57 mm.

In a preferred embodiment of the present invention an acetabular cup of relatively large outside diameter, such as, for example, 58 mm is used along with an appropriately matched prosthetic femoral head having a relatively large outside diameter, such as, for example, 52 mm. It will be appreciated that smaller or larger respective diameters, such as, for example, 30-75 mm, or even larger or smaller depending upon various factors such as patient anatomy, may be used without departing from the present invention. Nor is the present invention limited by any particular material for the prosthetic femoral head or the acetabular cup, which may preferably be made from cobalt chromium, but could also be made from titanium, tantalum, surgical grade stainless steel, ceramic, alumina ceramic or other materials of suitable strength and acceptance properties.

The prosthetic acetabular cup may also be made from more than one of these materials. FIG. 5A illustrates a representation of an inner 502 and an outer 504 portion of a two-piece prosthetic cup with aligned holes 510 used to join the two pieces in accordance with one embodiment of the present invention. For example, an outer cup 504 may be formed from titanium and may also be machined or grit-blasted to have a mesh-like, porous or roughened outer surface 508. A cobalt chromium inner cup 502 machined to have a smooth inner surface 506 may be fit into the titanium outer cup, such that the combination forms a unitary prosthetic acetabular cup. The outer and inner cups may be fixedly joined (1) by press-fitting the inner cup into the outer cup, or (2) by using one or more screws inserted through the outer cup and into the inner cup, or (3) by machining an outward facing circumferential flange or lip around the perimeter of the inner cup and fitting the lip around the perimeter of the outer cup and then pressing or pinching the lip to grip the perimeter of the outer cup, or (4) by other means such as welding or soldering or medical grade adhesives.

FIG. 5B illustrates a representation of a cutaway view of aligned holes 510 formed in walls of inner and outer cup portions of a two-piece prosthetic cup and a screw 512 to be inserted through the holes 510 to fix the cup portions relative to each other in accordance with one embodiment of the present invention. FIG. 5C illustrates a two-piece prosthetic cup in joined by a screw 512 accordance with one embodiment of the present invention. It will be appreciated that such embodiments may use more than one set of such aligned holes.

FIG. 5D illustrates a cross-sectional view of an embodiment of a two-piece prosthetic cup in accordance with one embodiment of the present invention wherein outer 514 and inner 516 cup pieces are joined by a lip 518 formed into the rim of the inner cup. FIG. 5E illustrates a two-piece prosthetic cup in accordance with an embodiment of the present invention wherein the outer 514 and inner 516 cup pieces are joined by the lip 518 formed into the rim of the inner cup piece. Other embodiments of the two-piece acetabular cup are contemplated in which different materials are used such as, for example, tantalum for the outer cup and alumina ceramic for the inner cup. As will be appreciated, numerous combinations of materials having sufficient strength and acceptance properties are possible.

The partially spherical inner surface of the acetabular cup and the engaging partially spherical outer surface of the prosthetic femoral head may be highly polished for reduced friction. Press-fit and other prosthetic acetabular cups known in the art may be used without departing from aspects of the present invention. Such press-fit cups include designs offered by numerous manufacturers, including Depuy, Zimmer and Wright Medical.

In a preferred embodiment, the acetabular cup of approximately 40 to 70 mm near-hemispherical diameter may be made from cobalt chromium, and may be hemispherically shaped and polished in the interior of the cup to minimize friction in a metal-on-metal engagement of the outer hemispherical surface of the prosthetic femoral head, which may be made from the same material, and also precisely shaped for fit and polished to minimize friction. In a further preferred embodiment, the inner surface of the prosthetic acetabular cup comprises less than a full hemisphere, and may extend through an angle ranging from approximately 150 degrees to approximately 179.9 degrees about a radial center. It is contemplated that, following the surgical procedure, bodily fluid may collect between the outer surface of the prosthetic femoral head and the inner surface of the prosthetic acetabular cup and may further reduce friction between the surfaces and also reduce wear upon the surfaces. The present invention is not limited by the material of the inner surface of the prosthetic acetabular cup, which, in addition to the foregoing examples, may also be polyethylene, PEAK or other like material provided in the form of a liner that is press fit or otherwise fixed in place to form an inner surface of the prosthetic acetabular cup.

The outer surface of the acetabular cup is machined to engage the surgically prepared bone of the acetabulum. In a preferred embodiment, the outer surface of the prosthetic acetabular cup is machined to have a mesh-like and/or porous surface or grit-blasted or Titanium plasma sprayed to have a roughened surface (e.g., for press-fit anchoring) to grip the surgically prepared bone surface of the acetabulum to prevent displacement and slippage during the cup insertion process and, as time passes after the procedure, to permit and receive bone growth into recesses in the outer surface of the prosthetic acetabular cup to prevent slippage and displacement as the patient makes use of the prosthetic hip joint.

Figure 6C:
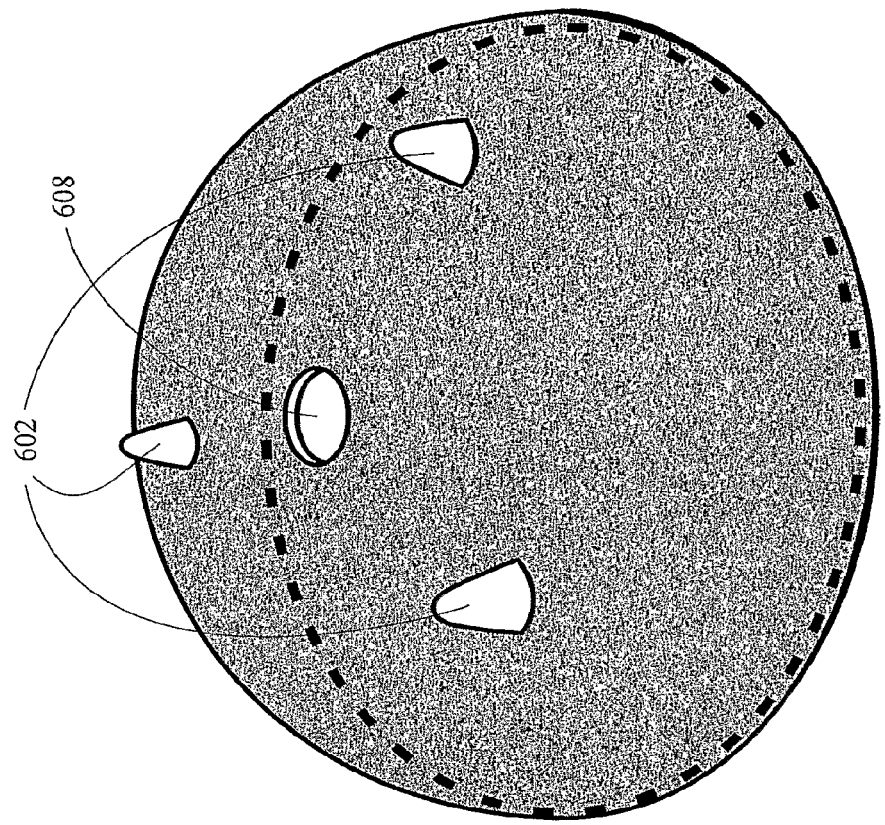
FIG. 6C illustrates a representation of a prosthetic acetabular cup having a plurality of anchoring protrusions in accordance with an embodiment of the present invention.
Figure 6A:
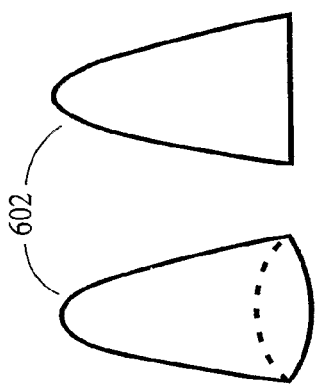
FIG. 6A illustrates a representation of a three-dimensional perspective and cross-sectional view of an anchoring protrusion for an outer surface of a prosthetic acetabular cup in accordance with one embodiment of the present invention.
Figure 6B:
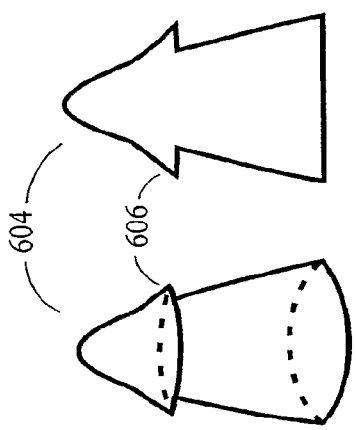
FIG. 6B illustrates a representation of a three-dimensional perspective and cross-sectional view of an anchoring protrusion for an outer surface of a prosthetic acetabular cup in accordance with another embodiment of the present invention.

In another embodiment of the invention, the prosthetic acetabular cup may include one or more protrusions or fins formed on its outer surface to further engage the acetabular bone and prevent slippage and/or rotation of the cup relative to the acetabulum. FIG. 6A illustrates a representation of a three-dimensional perspective and cross-sectional view of an anchoring protrusion 602 for an outer surface of a prosthetic acetabular cup in accordance with one embodiment of the present invention. FIG. 6B illustrates a representation of a three-dimensional perspective and cross-sectional view of an anchoring protrusion 604 for an outer surface of a prosthetic acetabular cup in accordance with another embodiment of the present invention. In this embodiment, each rounded conical protrusion 604 may include a circumferential indentation 606 to form a lateral lip approximately mid-way up the side of the conical structure. The indentation and lip advantageously engage new bone growth to resist displacement and assist fixation of the prosthetic acetabular cup over time. The protrusions may take the form of one or more spikes, small posts and/or ridges with or without barb-like or lip structures suitably shaped for penetrating and/or engaging the acetabular bone. FIG. 6C illustrates a representation of an outer surface of a prosthetic acetabular cup having a plurality of anchoring protrusions 602 in accordance with an embodiment of the present invention.

The prosthetic acetabular cup may also include a threaded impaction bore 608 located at or near its near-hemispherical center. During impacting of the acetabular cup, the threaded impaction bore 608 engages a threaded head of an impactor tool to hold the acetabular cup in place during impacting to help ensure secure seating. This example of a prosthetic acetabular cup includes three approximately rounded conical protrusions 602 located on the outer surface of the acetabular cup approximately equidistant from each other and each approximately equidistant from the rim of the cup and the impaction bore 608. It will be appreciated that alternative placements of the protrusions or fins 602 may be used. Each protrusion may have a slightly rounded and/or dulled tip.

Figure 7:
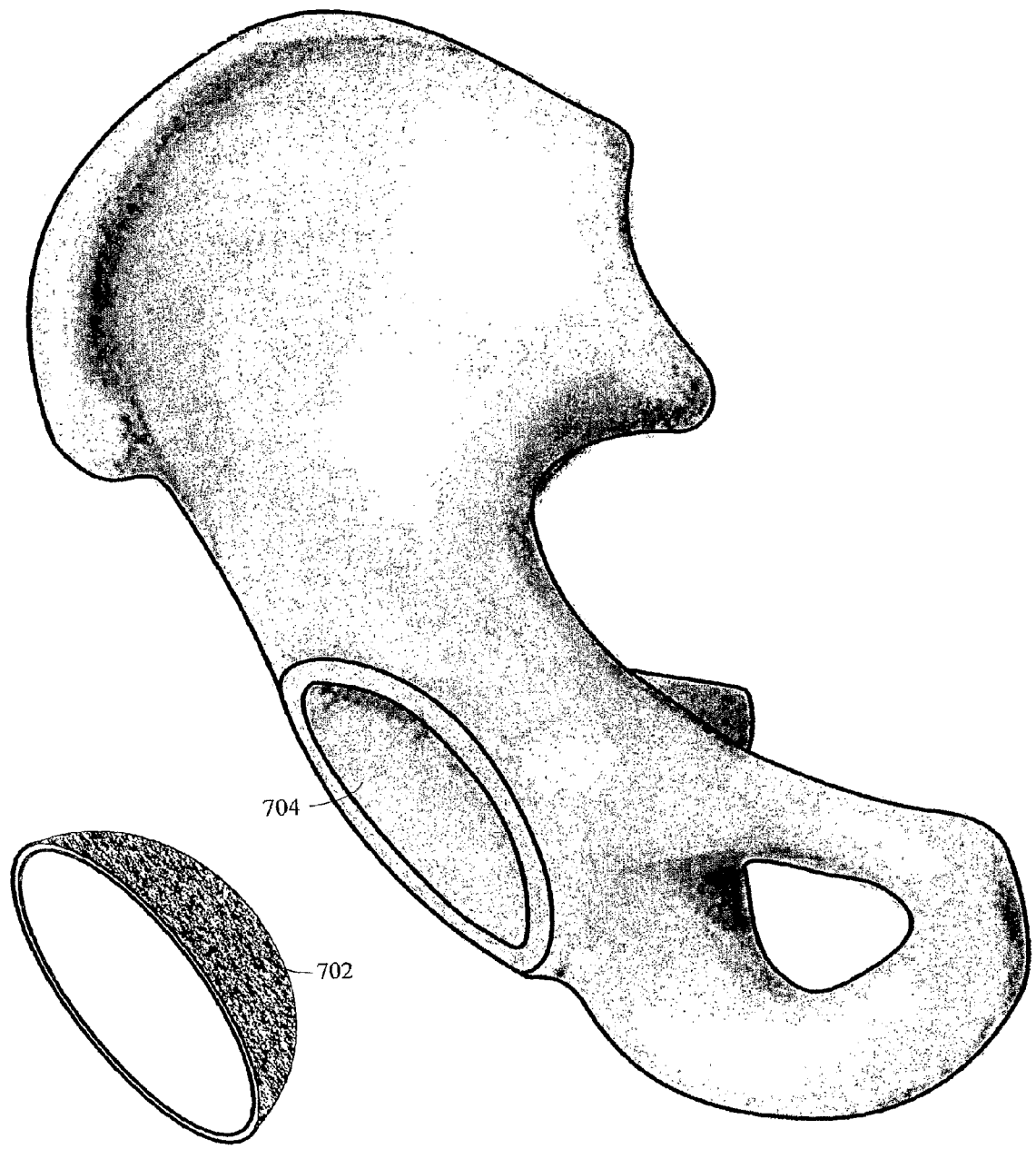
FIG. 7 illustrates a representation of a prosthetic acetabular cup in relationship to an acetabulum in preparation for impacting in accordance with an embodiment of the present invention.

FIG. 7 illustrates a representation of a prosthetic acetabular cup 702 in preparation for impacting in a reamed acetabulum 704 in accordance with an embodiment of the present invention. An outer surface of the prosthetic acetabular cup 702 may have a porous surface to engage bone growth from the reamed surface of the acetabulum 704. Additional fixation may be derived from protrusions along the outer surface of the prosthetic acetabular cup 702 and/or from fixation screws inserted through fixation bores.

Figure 8B:
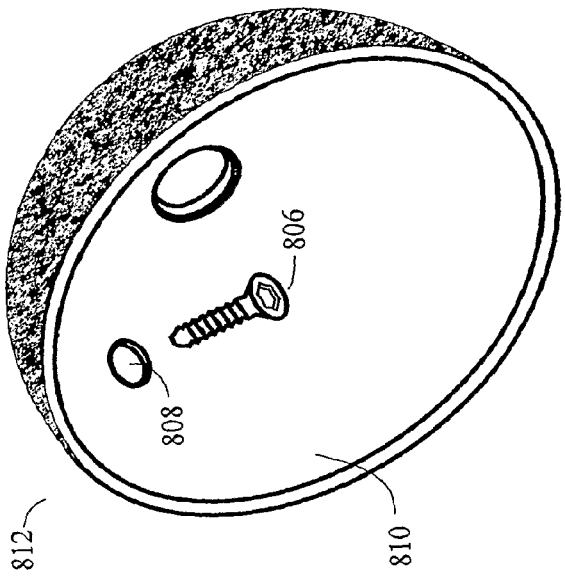
FIG. 8B illustrates a representation of an inner surface of a prosthetic acetabular cup with a fixation screw positioned to be fitted into a hole in the inner surface to fix the prosthetic acetabular cup to an acetabulum in accordance with an embodiment of the present invention.
Figure 8D:
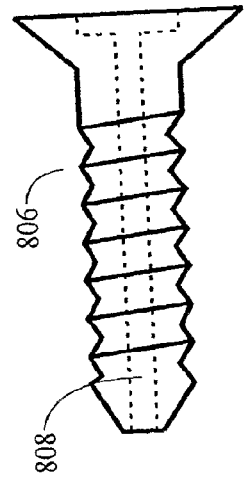
FIG. 8D illustrates a representation of a fixation screw having a shaft bore in accordance with an embodiment of the present invention.
Figure 8A:
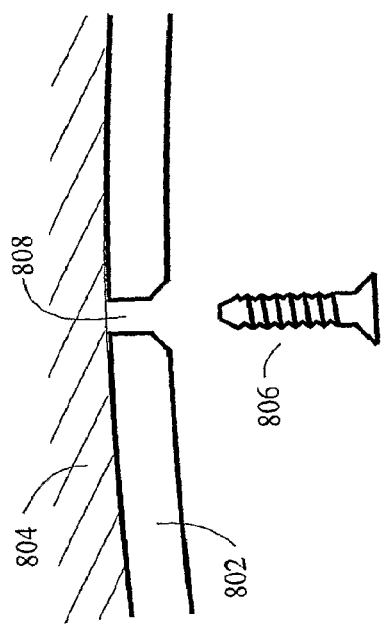
FIG. 8A illustrates a representation of a cross-sectional view of a wall of a prosthetic acetabular cup in relationship to an acetabulum, with a fixation screw positioned to be fitted into a hole in the wall to fix the prosthetic acetabular cup to the acetabulum in accordance with an embodiment of the present invention.

In a preferred embodiment, the prosthetic acetabular cup includes one or more placement fixation bores, which may have beveled edges. FIG. 8A illustrates a representation of a cross-sectional view of a wall 802 of a prosthetic acetabular cup in relationship to an acetabulum 804, with a fixation screw 806 positioned to be fitted into a placement fixation bore 808 in the wall 802 to fix the prosthetic acetabular cup to the acetabulum 804 in accordance with an embodiment of the present invention. FIG. 8B illustrates a representation of an inner surface 810 of a prosthetic acetabular cup 812 with a fixation screw 806 positioned to be fitted into a placement fixation bore 808 extending through the wall of the prosthetic acetabular cup 812 to receive the fixation screw 806 and thereby fix the prosthetic acetabular cup 812 to an acetabulum. In a preferred embodiment, the prosthetic acetabular cup 812 includes a placement fixation bore 808 at a point approximately midway between the rim of the prosthetic acetabular cup 812 and the hemispherical center.

Figure 8C:
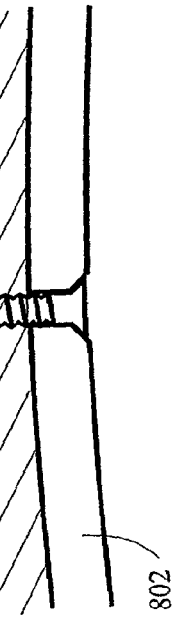
FIG. 8C illustrates a representation of a cross-sectional view of a wall of a prosthetic acetabular cup in relationship to an acetabulum, with a fixation screw fitted through a hole in the wall and fixing the prosthetic acetabular cup to the acetabulum in accordance with an embodiment of the present invention.

FIG. 8C illustrates a representation of a cross-sectional view of the wall 802 of a prosthetic acetabular cup 812 in relationship to the acetabulum 804 with the fixation screw 806 fitted through the placement fixation bore in the wall and fixing the prosthetic acetabular cup to the acetabulum 804. In one embodiment, the diameter of the placement fixation bore 808 is slightly larger at the inner surface and slightly smaller further along the bore toward the outer surface of the prosthetic acetabular cup so that the bore is slightly tapered for at least a portion of its length, and a head of the fixation screw 806 may be likewise tapered so that, when threaded into bone through the placement fixation bore 808 and tightened, the head of the fixation screw 806 is fully recessed into the tapered region of the placement fixation bore 808 and thus advantageously creates no friction or wear by any engagement of the outer surface of the prosthetic femoral head.

Accordingly, to further assure seating fixation of the prosthetic acetabular cup 812 in the acetabulum, a fixation screw 806 or similarly suitable anchoring device is fit through the placement fixation bore 808 to affix the prosthetic acetabular cup 812 into the reamed acetabulum 804. Such use of the placement fixation bore 808 advantageously supports the impacting step by further avoiding slippage of the prosthetic acetabular cup 812 and reducing any consequent need for repeated trials of acetabular cup placement or further surgical procedures to properly fit, secure and seat the prosthetic acetabular cup 812.

In a further preferred embodiment of the present invention, the fixation screw 806 includes a central bore creating an open path approximately along its longitudinal center from head to tip. FIG. 8D illustrates a representation of a fixation screw 806 having a central bore 814 in accordance with an embodiment of the present invention. It is contemplated that the central bore 814 in the fixation screw 806 advantageously permits fluid to enter from the bone and through the central bore 814 into the space between the outer surface of the prosthetic femoral head and the inner surface of the prosthetic acetabular cup 812 and thereby further minimizes friction and wear resulting from the movement of those two surfaces relative to each other.

With the acetabulum prepared, the prosthetic acetabular cup may be seated into place, for example, by impaction. FIG. 9A illustrates a representation of a cutaway view of an impactor tool 902 joined to a prosthetic acetabular cup 812 in position for impacting in accordance with an embodiment of the present invention.

A threaded portion 906 of a shaft 908 of the impactor tool 902 may be threaded into the impaction bore of the prosthetic acetabular cup 812 to hold the cup in relation to the impactor tool 902 while it is impacted into the prepared acetabulum 910. As shown, a conical sleeve 912 having a convex engaging surface 914 formed to engage the inner surface 916 of the prosthetic acetabular cup 812 may be fitted around the threaded end of the shaft 908 of the impactor tool 902 to advantageously spread the force of the impaction across additional area of the inner surface of the prosthetic acetabular cup 812. Advantageously, the conical sleeve 912 may be made from any surgically acceptable material that will not scratch, score or damage the inner surface of the prosthetic acetabular cup 812 during impaction. A few taps on the end of the impactor tool 902 opposite the threaded portion 906 may impact the prosthetic acetabular cup 812 firmly into the acetabulum 910. FIG. 9B illustrates a representation of a cutaway view of the impactor tool 902 in relation to a prosthetic acetabular cup 904 impacted into an acetabulum 910 in accordance with an embodiment of the present invention.

Figure 10:
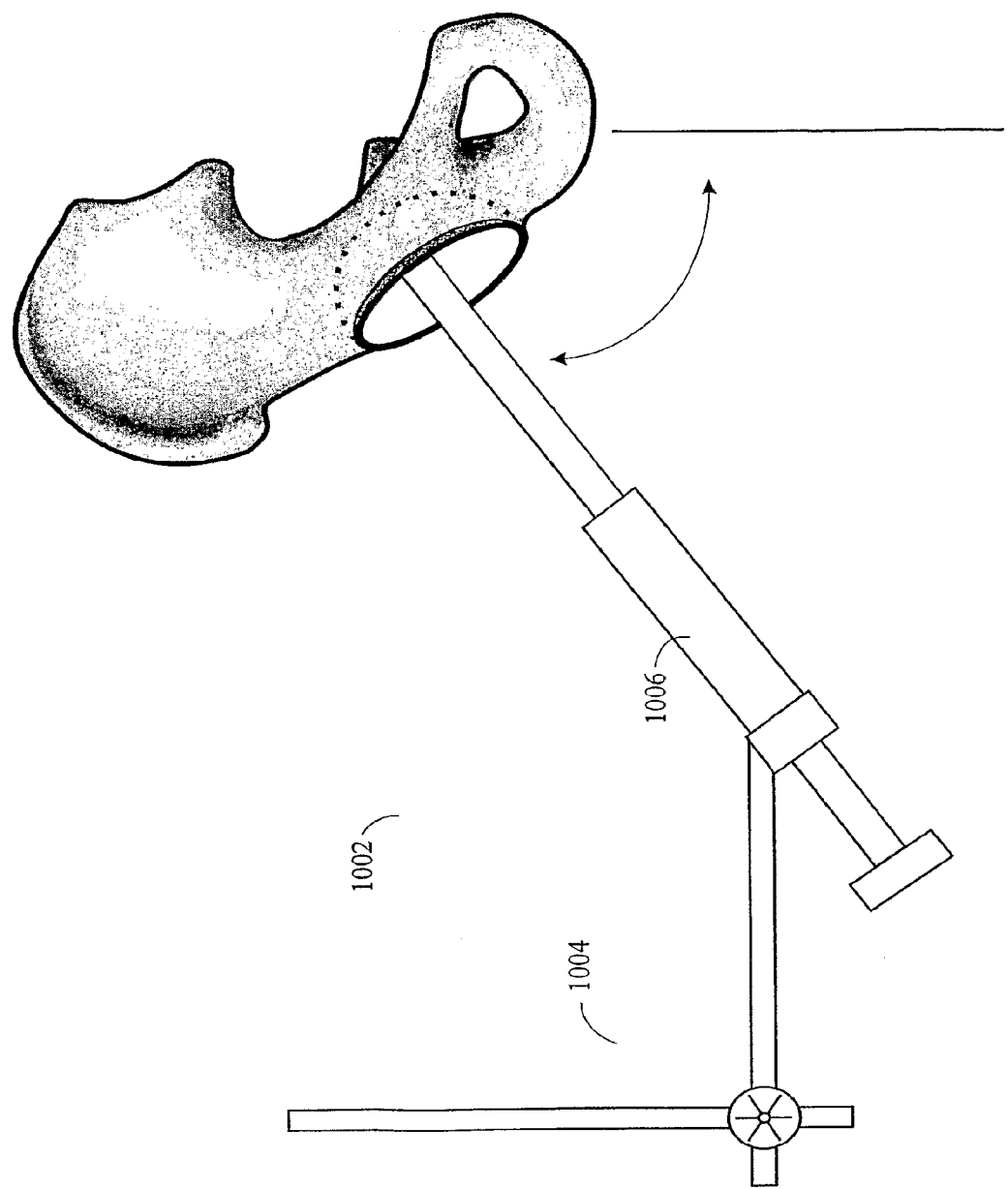
FIG. 10 illustrates a representation of an impactor tool having apparatus indicative of an abduction angle in accordance with an embodiment of the present invention.

As is generally known, the impactor tool may include apparatus indicative of an abduction angle. FIG. 10 illustrates a representation of an impactor tool having apparatus 1002 indicative of an abduction angle in accordance with an embodiment of the present invention. A guide bar assembly 1004 rotatably fixed to a cylindrical sleeve 1006 fit over the shaft of the impactor tool advantageously assists in measuring and/or confirming the angle of abduction, which may desirably be approximately 45 degrees.

Once the prosthetic acetabular cup is impacted into and properly seated in the acetabulum, and preferably after proper orientation of the prosthetic acetabular cup has been confirmed, the impactor tool 902 may be removed by unscrewing it from the threaded impaction bore in the prosthetic acetabular cup 812.

With the prosthetic acetabular cup 812 impacted into place, the fixation screw 806 may be threaded through the fixation bore 808 and into the bone of the acetabulum. Preferably the fixation bore 808 is oriented approximately toward the iliac crest where acetabular bone is sufficiently thick to receive the fixation screw 806, which may be approximately 7-14 mm long. It will be appreciated that the prosthetic acetabular cup 812 may have additional fixation bores oriented toward thick bony areas of the acetabulum, and that additional fixation screws tightened through these bores may provide for additional fixation of the prosthetic acetabular cup 812.

Figure 11:
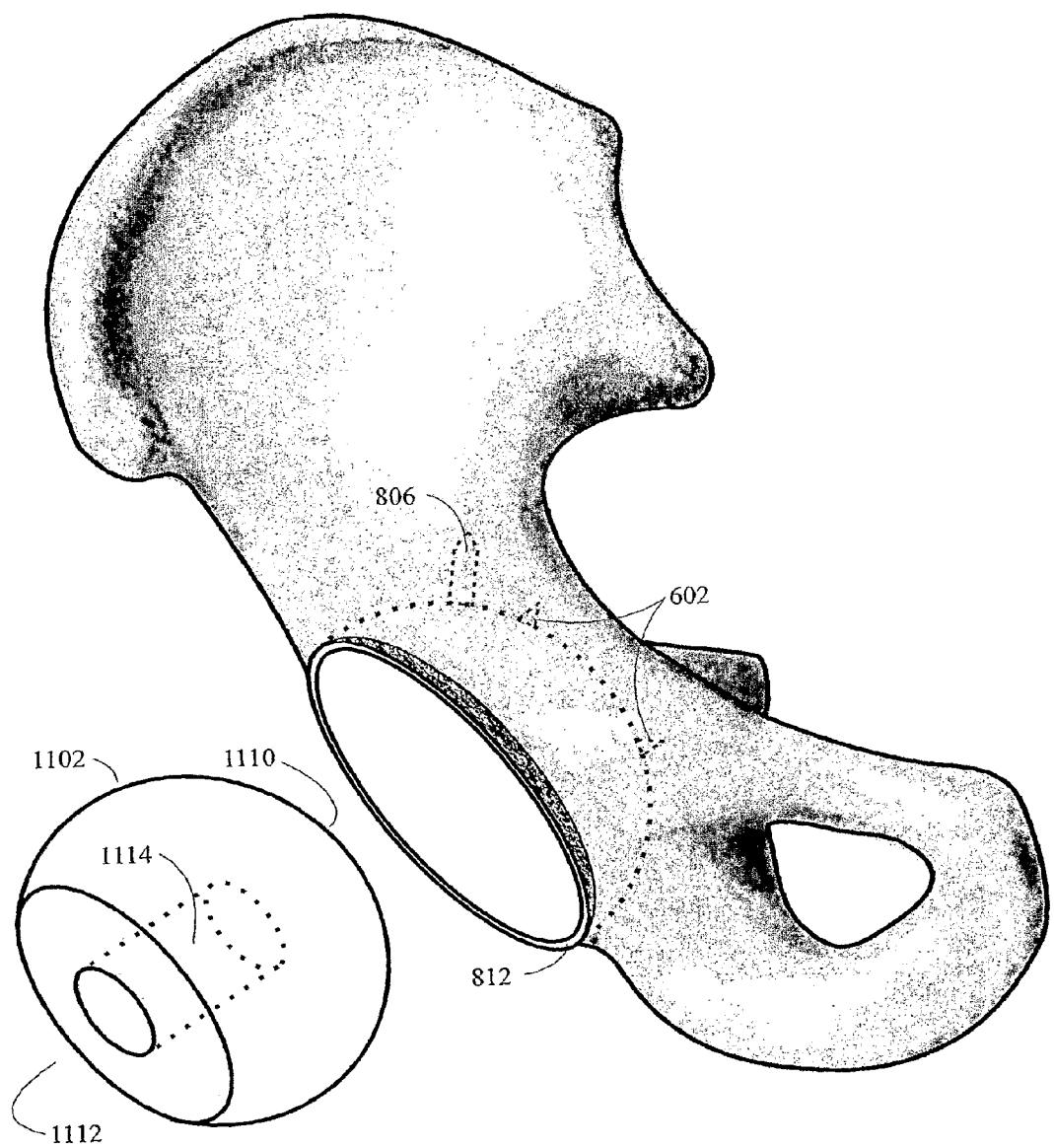
FIG. 11 illustrates a representation of a prosthetic femoral head in position for placement in relation to an impacted prosthetic acetabular cup in accordance with an embodiment of the present invention.

Attention is then turned to fitting the prosthetic femoral head into the prosthetic acetabular cup 812. FIG. 11 illustrates a representation of a prosthetic femoral head 1102 in position for placement in relation to a seated prosthetic acetabular cup 812 fixed by a fixation screw 806 or by protrusions 602 in accordance with an embodiment of the present invention. In a preferred embodiment, the prosthetic femoral head 1102 at a cup-engaging end 1110 comprises a partial sphere having a curvature machined to precisely fit the inner surface of the prosthetic acetabular cup 812. The partial sphere of the prosthetic femoral head 1102 may extend, in various embodiments from approximately 160 degrees to approximately 340 degrees, and thus may comprise any range from somewhat less than a hemisphere to nearly a full sphere.

In accordance with the present invention, the prosthetic femoral head at a neck engaging end 1112 includes structural means to receive and engage a prosthetic femoral neck. In a preferred embodiment, neck engagement may be achieved by a very slightly and narrowingly tapered cylindrical neck bore 1114 machined approximately 2 cm into the prosthetic femoral head from the neck engaging end 1112 inward toward the center of the prosthetic femoral head, such that a head-engaging end of a prosthetic femoral neck comprising roughly 2 cm of cylindrical shaft having a Morse taper matched to that of the neck bore 1114 may be driven by impact into the neck bore 1114, resulting in a fit sufficiently permanent to operatively support load-bearing movement about the prosthetic hip without slippage. It will be appreciated that such Morse taper modular joining techniques have been known for many years to successfully achieve such fit. It will also be appreciated that a neck bore 1114 may extend more than or less than 2 cm into the prosthetic femoral head, and that in such cases, the head-engaging end of the prosthetic femoral neck will be of a roughly corresponding length of more than or less than 2 cm. Also, the diameter of the neck bore 1114 will be approximately 11-13 mm (and will very gradually decrease as the bore extends into the prosthetic femoral head to accommodate the taper), although it will be appreciated that smaller or larger diameters may be used, and it will also be appreciated that the shaft diameter of the head-engaging end of the prosthetic femoral neck will be of a diameter matching that of the neck bore 1114.

Figure 12:
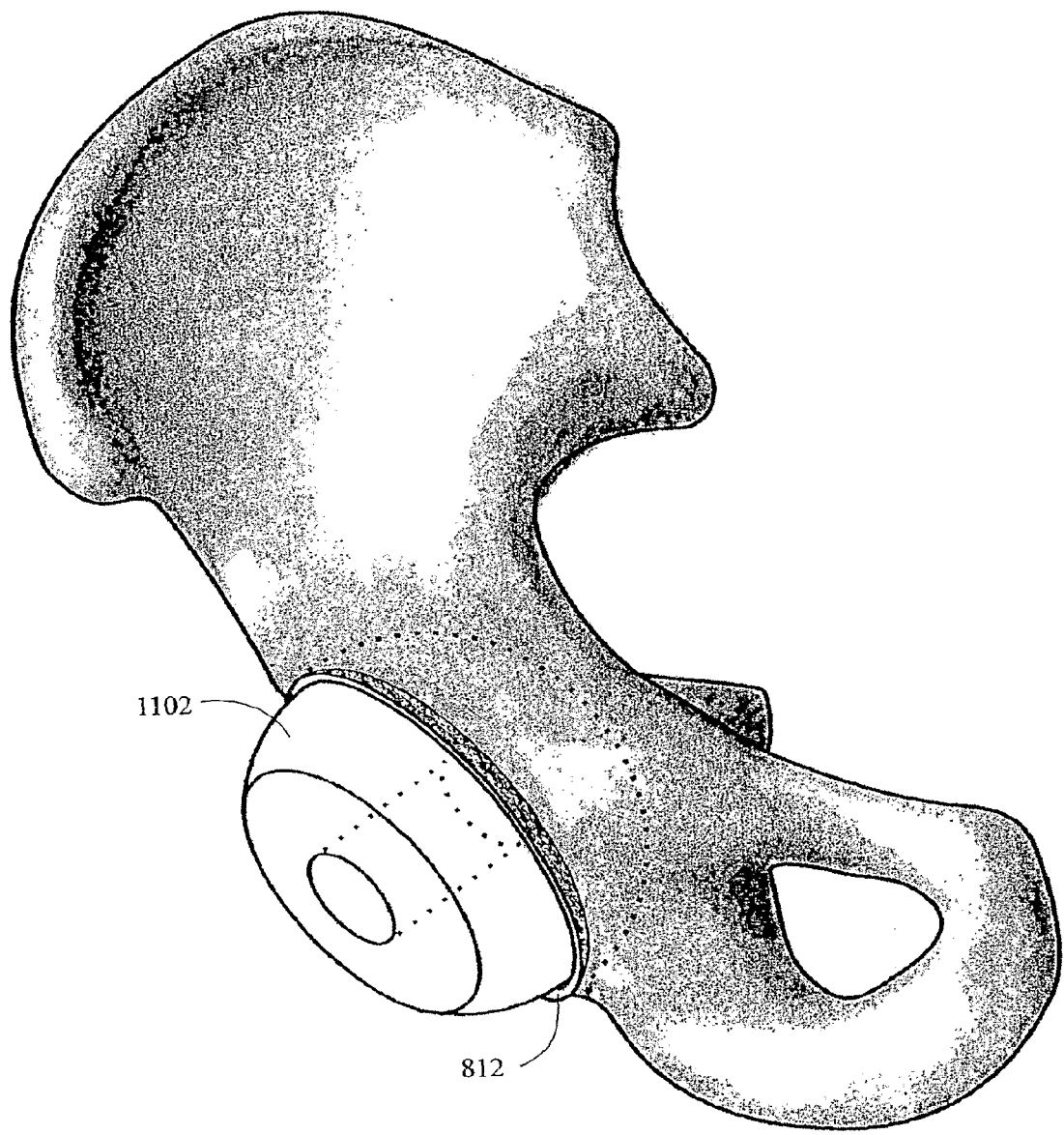
FIG. 12 illustrates a representation of a prosthetic femoral head positioned in a prosthetic acetabular cup in accordance with an embodiment of the present invention.

In one embodiment, the partial sphere of the prosthetic femoral head is placed against the exposed rim of the hemispherical inner surface of the prosthetic acetabular cup 812. As will be appreciated, one or more light taps using a firm rubber-headed impacting tool may then seat the prosthetic femoral head properly into the prosthetic acetabular cup 812. FIG. 12 illustrates a representation of a prosthetic femoral head 1102 positioned in a prosthetic acetabular cup 812 in accordance with an embodiment of the present invention.

In still another embodiment of the present invention, the acetabular cup, as described above but optionally without the placement fixation hole and optionally with anchoring protrusions or fins, is pre-operatively fitted (for example, previously machined to optimal tolerance gap, e.g. 100 micron) with the prosthetic femoral head. Advantageously, the pre-operatively assembled prosthetic acetabular cup and prosthetic femoral head—which may advantageously be sterilely packaged together—may be impacted into the prepared acetabulum as a single unit. As will be appreciated, an impacting insertion device may fit into the Morse taper of the prosthetic femoral head and also connect to or engage the rim of the prosthetic acetabular cup for rotation control.

In another embodiment (not shown), a different attachment technique may be used to join the prosthetic femoral head to a prosthetic femoral neck. For example, the prosthetic femoral head, rather than include a neck bore, may include a neck shaft. The neck shaft may extend approximately 2 cm outward from the neck-engaging end of the prosthetic femoral head. The neck shaft may be approximately 11-13 mm in diameter (though smaller or larger diameters could be used), with the diameter slightly decreasing along the neck shaft in the direction away from the center of the prosthetic femoral head, to form a Morse taper. It will be appreciated that a prosthetic femoral neck in approximately the form of a cylindrical shaft, may be machined to include a bore in one end having a receiving Morse taper of proper dimension to engage the neck shaft. It will be appreciated that still further methods and structures exist that could be adapted to the prosthetic femoral head and prosthetic femoral neck to facilitate the joining of these two prostheses.

Attention is then turned to preparation of the proximal femur for introduction of an intramedullary rod. In accordance with the present invention, the intramedullary rod, as described in various forms herein, may have characteristics of a femoral stem. The intramedullary rod may advantageously be inserted into the patient's femur 104 using surgical technique which requires only minimal exposure of the femur.

Figure 13:
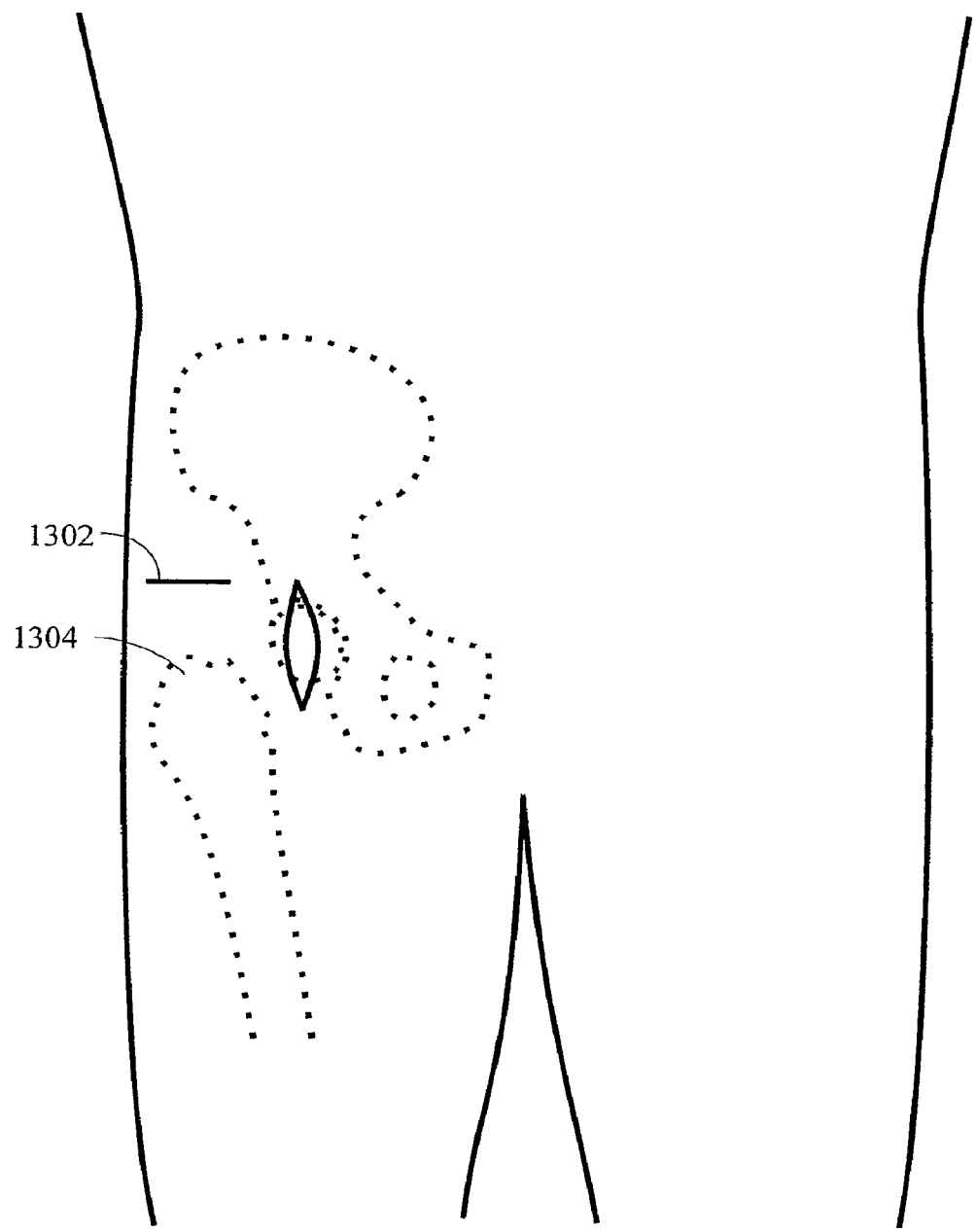
FIG. 13 illustrates a representation of a second incision in accordance with an embodiment of the present invention.

An incision of approximately 3-4 cm is made at approximately a mid-portion of Smith-Peterson anterior approach. FIG. 13 illustrates a representation of an incision 1302 in accordance with an embodiment of the present invention. Access to the proximal femur may be attained by a lateral longitudinal incision proximal to the greater trochanter, dissecting down to the gluteus maximus fascia longitudinally in the direction of the wound, separating the underlying muscle fibers and palpating the medial tip of the greater trochanter; the entry point may be penetrated by a cannulated awl and a guide wire may be inserted into the intramedullary canal. The guide wire may be centered in the canal in the lateral view on C-arm image.

Reaming and/or broaching may be done over the guide wire. In this manner, safe access may be gained to the upper surface of the femur 1304 around and about the greater trochanter.

In another embodiment, surgical access to the acetabulum and to the proximal femur may be obtained by a somewhat longer portion of a Smith-Peterson anterior approach.

Figure 14:
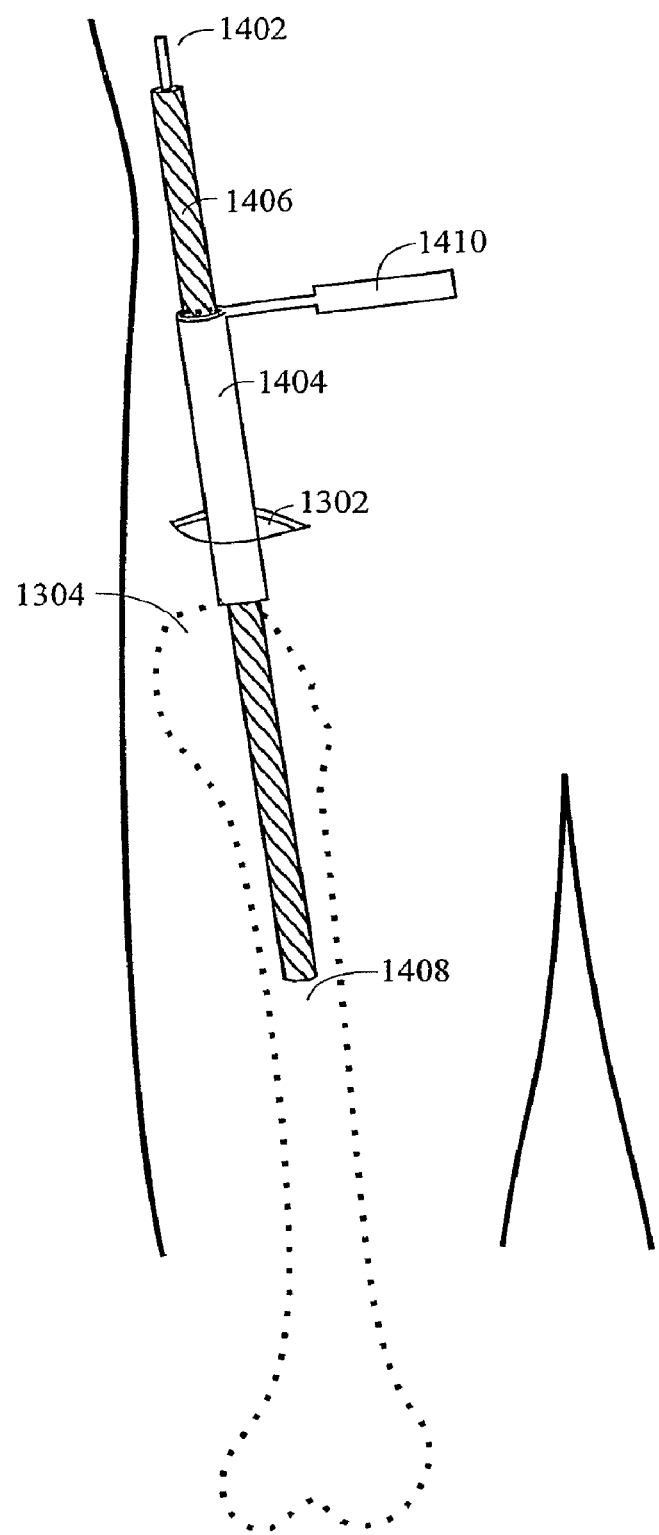
FIG. 14 illustrates a representation of a femoral reaming tool with a tissue protecting guide in accordance with an embodiment of the present invention.

With access to the upper portion of the proximal femur 1304 attained, and using known surgical technique, tissues along the upper surface of the femur 1304 are reflected by a tissue protector. FIG. 14 illustrates a representation of a femoral reaming tool 1402 with a tissue protecting guide 1404 in accordance with an embodiment of the present invention.

The reamer 1402 comprises a drilling bit 1406 rotated by a drill motor (not shown) while being directed into the intramedullary canal 1408 of the femur 104 by a guide wire to a depth sufficient to accommodate most if not all of the length of the distal end of the intramedullary rod. Reamers of increasing diameter may be used to progressively achieve a bore in the proximal femur of sufficient diameter to accommodate that of the proximal region of the intramedullary rod. Tissues along the surgical access may be protected from the rotating reamer bit and the bit itself may be guided by the use of a tubular tissue protector 1404 to which is affixed a handle 1410 for ease of use. As is known, over-reaming by approximately one millimeter may facilitate advantageous blood flow after the intramedullary rod has been inserted. Advantageously, the use of a guide wire or guide pin may assist in accurate reaming and/or broaching and/or introduction of an intramedullary rod.

The intramedullary rod may be made from any biocompatible material of sufficient strength, however titanium alloy is preferred. FIG. 15A illustrates a representation of a three-dimensional side view of an intramedullary rod 1502 with a femoral neck bore 1504 in accordance with an embodiment of the present invention, and FIG. 15B illustrates a representation of a three-dimensional front view of the intramedullary rod 1502 in accordance with the embodiment of the present invention. The present invention is not limited to a particular length of the intramedullary rod 1502, which may be from 15-40 cm long, or possibly shorter or longer depending for example upon patient anatomy.

The intramedullary rod 1502 includes a proximal region 1506 that may be approximately 6-8 cm long and may have a diameter of around 15-18 mm, and the rod also includes a stem 1508 distal to the proximal region having a diameter of around 10 mm, and the stem 1508 may taper distally with a gradually narrowing diameter terminating in a rounded point 1510. It will be appreciated that the intramedullary rod 1502 may curve slightly along its length to advantageously align with the longitudinal center of the femur 104.

In another embodiment, the proximal region may be somewhat shorter, for example, from 4-6 cm. This embodiment may be preferred in procedures involving additional removal of bone from the proximal region of the femur and/or in combination with a support sleeve as is described in more detail below.

The intramedullary rod includes a lateral neck bore 1504 through the proximal region 1506 at an angle that advantageously permits a shaft-like prosthetic femoral neck to be inserted at an insertion side of the neck bore 1504 and therethrough to engage the prosthetic femoral head 1102, which may preferably and advantageously already be in place in the prosthetic acetabular cup 812. The diameter of the neck bore 1504 may preferably be approximately 10-12 mm, but it will be appreciated that the diameter could be somewhat smaller or larger. The angle of the neck bore may be around 130 degrees, or may be more or less depending upon patient anatomy and condition of the proximate bones and tissues.

The intramedullary rod also includes a fixation bore 1512 that runs longitudinally from the center of the proximal region 1506 through the longitudinal center of the intramedullary rod 1502 until it meets the neck bore 1504 approximately 4 cm from the proximal end. The fixation bore 1512 may preferably have a diameter of approximately 8 mm, but may be more or less. The fixation bore 1512 is preferably spiral threaded to receive locking or fixation screws as described herein.

The proximal end of the intramedullary rod 1502 includes a keyway providing for fixation of other structures relative to the intramedullary rod. FIG. 15C illustrates a representation of a fixation keyway 1514 formed in the proximal end of an intramedullary rod 1502 in accordance with an embodiment of the present invention, and FIG. 15D illustrates a representation of another fixation keyway 1516 formed in the proximal end of an intramedullary rod 1502 in accordance with another embodiment of the present invention.

In one embodiment, a preferred circular keyway 1514 comprises a key bore 1518 of approximately 12 mm in diameter and of about 2 mm depth centered on the longitudinal axis of the intramedullary rod and machined into the proximal end of the intramedullary rod 1502. The key bore 1518 defines a circular step within the proximal end of the intramedullary rod 1502. The keyway preferably further includes a notch 1520 in the rim of the proximal end of the intramedullary rod 1502 defined by the key bore 1518. The notch 1520 is preferably about 2 mm wide and 2 mm deep. The notch 1520 is aligned circumferentially about the longitudinal axis of the intramedullary rod to coincide with the center of the circular hole at the insertion side of the neck bore 1504. It will be appreciated that another structure having a recessed circular rim may engage the keyway, and that a 2 mm protrusion projecting outward from the recessed circular rim of the other structure may fit in the notch 1520 of the keyway to prevent the other structure from rotating with respect to the intramedullary rod 1502 along the longitudinal axis.

An alternative embodiment of a keyway 1516 (see FIG. 15D) includes four roughly rectangular recesses 1522 formed in the rim of the proximal end of the intramedullary rod 1502. The rectangular recesses may be approximately 2 mm deep and 2 mm wide. It will be appreciated that another structure having projections matched to the recesses 1522 may engage the keyway 1516 and may prevent the intramedullary rod 1502 from rotating about its longitudinal axis relative to the other structure.

It will be appreciated that any and all of the dimensions of the intramedullary rod 1502, including the lengths and diameters and tapers of the proximal region, the stem and the bores, may be smaller or larger as indicated by patient anatomy, condition of any of the bones and tissues or other circumstances.

Figures 16A, 16B:
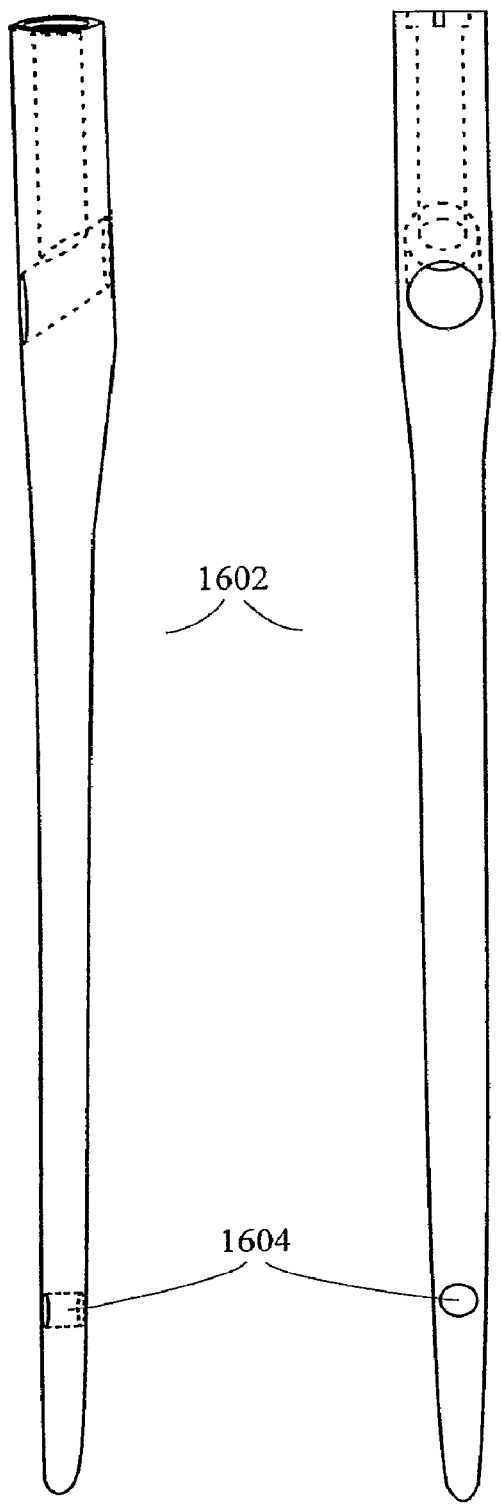
FIG. 16A illustrates a representation of a three-dimensional side view of an intramedullary rod with a femoral neck bore and a distal fixation bore in accordance with an embodiment of the present invention.
FIG. 16B illustrates a representation of a three-dimensional front view of an intramedullary rod with a femoral neck bore and a distal fixation bore in accordance with an embodiment of the present invention.

FIG. 16A illustrates a representation of a three-dimensional side view of an intramedullary rod 1602 with a distal fixation bore 1604 in accordance with an embodiment of the present invention, and FIG. 16B illustrates a representation of a three-dimensional front view of such an intramedullary rod 1602. It will be appreciated that a pin or screw may be inserted through a side of the distal femur to engage the distal fixation bore 1604. Accordingly, this intramedullary rod 1602 may be advantageous in providing additional fixation, particularly in an anti-rotational manner, in relation to the femur 104. Moreover, this intramedullary rod 1602 provides the additional advantage of readily treating peri-prosthetic fractures following a total hip procedure, wherein the intramedullary rod used in the initial procedure may be replaced by the intramedullary rod 1602 having a longer distal stem, which, in combination with a pin or screw in the fixation bore 1604 to secure the distal femur, provides adequate support structure to treat such fracture. This versatility in facilitating and simplifying treatment of peri-prosthetic fractures is another advantage of the present invention.

Turning to the insertion of the intramedullary rod 1502 in the femur 104, a driving tool may advantageously be securely attached to the keyway 1514 located at the proximal end of the intramedullary rod. FIG. 17A illustrates a representation of a side view of a driving tool 1702 engaging an intramedullary rod 1502 to be driven into a femoral canal in accordance with an embodiment of the present invention. FIG. 17B illustrates a representation of a rear side view of the driving tool 1702 in accordance with the embodiment, and FIG. 17C illustrates a representation of a top down view of the driving tool 1702.

A driving surface 1704 of the driving tool 1702 transfers force from light hammer blows along an elongated head shaft 1706 through the keyway 1514 to the intramedullary rod 1502 so that the rod is driven by the blows into the marrow canal. The driving tool 1702 may preferably made from stainless steel, or another material sufficiently hard and heavy that it withstands hammer blows and effectively transfers force, and may also be repeatedly sterilized. The driving tool 1702 may be held by a handle 1708 during insertion of the intramedullary rod 1502. Imaging may be used to facilitate and confirm proper orientation and location of the intramedullary rod 1502 within the marrow canal.

In one embodiment, a keyway formed in a rod-engaging end of the driving tool 1702 holds the driving tool 1702 securely in relation to the intramedullary rod 1502 while it is being driven into the femur 104.

FIG. 17D illustrates a representation of a keyway 1710 formed in an engaging end 1712 of the driving tool 1702 in accordance with an embodiment of the present invention. As shown, the circular keyway 1710 formed on the engaging end 1712 of the driving tool 1702 engages the circular keyway 1514 on the proximal end of the intramedullary rod 1502. The circular keyway 1710 permits the driving tool to rotate with respect to the longitudinal axis of the intramedullary rod 1502 while remaining laterally centered over the top of the intramedullary rod 1502 for effective driving of the intramedullary rod 1502. It will be appreciated that, in this embodiment, the circular keyway 1710 on the engaging end 1712 of the driving tool 1712 includes no protrusion along the circular rim and thus nothing engages the notch 1520 in the circular keyway on the proximal end of the intramedullary rod 1502.

FIG. 17E illustrates a representation of another embodiment of a keyway 1714 in an engaging end of the driving tool 1702 in accordance with an embodiment of the present invention. The keyway 1714 includes four protrusions 1716 extending circumferentially around the perimeter of the engaging end 1712 of the driving tool. As such, it will be appreciated that the protrusions 1716 may fit into and engage recessions around the perimeter of a receiving keyway 1516, as described above, to hold the driving tool 1702 steady in relation to the intramedullary rod 1502 while the driving tool 1702 is being used to drive the intramedullary rod 1502 into the femur 104.

In another embodiment, a support sleeve may be fixed within the proximal region of the femur to use the bone mass in that region to further support the intramedullary rod 1502. FIG. 18A illustrates a representation of a top down view of a support sleeve 1802 for an intramedullary rod 1502 in accordance with an embodiment of the present invention. FIG. 18B illustrates a representation of a rear view of the support sleeve 1802, and FIG. 18C illustrates a representation of a side view of the support sleeve 1802. FIG. 18D illustrates a representation of a perspective view of the support sleeve 1802.

The support sleeve 1802 may advantageously be generally shaped to fit within the proximal region of the femur. The support sleeve 1802 may be made from titanium in one embodiment with a grit-blasted roughened outer surface. It will be appreciated that the support sleeve 1802 may be made from other materials, such as cobalt chromium, ceramic, stainless steel or other materials of sufficient strength and acceptance qualities. It will also be appreciated that the bone engaging surfaces of the support sleeve 1802 may have one or more of a variety of textures as described above to facilitate gripping of and fixation within bone.

With reference to FIG. 18C, the support sleeve 1802 includes a narrow-angled conical portion 1804 with a central rod bore 1806 which, when the support sleeve 1802 is in place within the femur 104, is approximately aligned with the longitudinal center of the femur 104. The diameter of the conical portion 1804 may be around 2-3 cm at the distal end and around 2.5-4 cm at the proximal end, however the diameters may be somewhat larger or smaller depending on patient anatomy and/or tightness of fit desired. The central rod bore 1806 may have a diameter only very slightly larger than that of the proximal region of the intramedullary rod 1502. The central rod bore 1806 may also be slightly tapered—larger at the proximal end and smaller at the distal end—to ensure a tight fit around the proximal region of the intramedullary rod 1502.

The support sleeve 1802 also includes a roughly triangular shaped portion 1808 projecting from the conical portion 1806 starting approximately midway along the longitudinal length of the support sleeve 1802. When the support sleeve 1802 is in place in the femur 104, the triangular portion 1808 may extend outward laterally from the cylindrical portion in a direction toward the acetabulum and may rise over the lower trochanter to occupy the space within the proximal femur above the lower trochanter. When the support sleeve 1802 is fit into place, an upper and laterally extending flat surface 1810 of the support sleeve 1802 may extend from a point below the greater trochanter and in the direction of and a small distance past the lower trochanter. The flat surface 1810 may occupy a plane that is roughly perpendicular to the length of the femur 104 and situated around 1-1.5 cm above the lower trochanter. In one embodiment, the upper flat surface 1810 extends laterally approximately 3-5 millimeters beyond the lower trochanter toward the acetabulum.

Advantageously, with respect to FIG. 18D, the support sleeve 1802 includes a neck slot 1812 to accommodate a prosthetic femoral neck. The neck slot 1812 may be cut in a wall of the conical portion 1804 of the support sleeve 1802 that is opposite the triangular portion 1808 and may extend longitudinally from the proximal extent of the wall to a point approximately halfway toward the distal extent of the wall. The neck slot 1812 may be sufficiently wide to accommodate the diameter of the prosthetic femoral neck, allowing it to pass through the neck slot 1812. The neck slot 1812 may extend laterally from the wall into the support sleeve 1802 to a point above the lower trochanter. From a point at the distal extent of the neck slot 1812 along the wall, a floor 1814 of the neck slot 1812 may rise into the support sleeve 1802 toward the proximal end of the support sleeve 1802 at an angle of preferably 30-40 degrees, but the angle could be more or less. The neck slot 1812 may also divide the upper flat surface 1810 of the support sleeve 1802 from the end nearest the greater trochanter to a point approximately 1 or 2 mm from the end of the flat surface 1810 nearest the lower trochanter. The neck slot 1812 in the support sleeve 1802 advantageously permits the prosthetic femoral neck to occupy a substantially straight path through the support sleeve 1802 at an appropriate angle to engage the prosthetic femoral head.

Figure 19C:
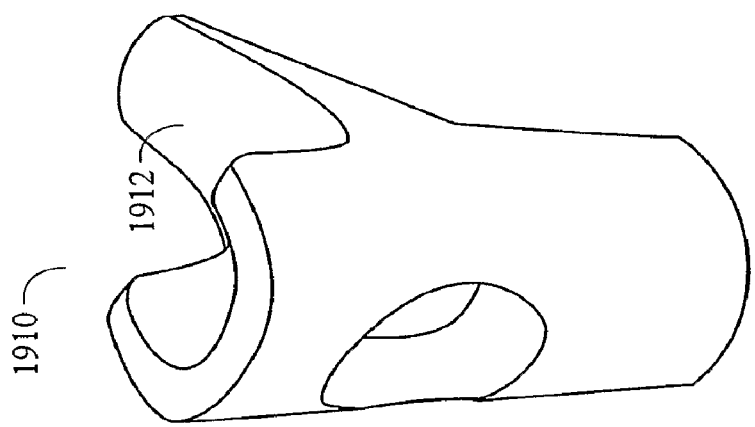
FIG. 19C illustrates a representation of a perspective view of a support sleeve for an intramedullary rod in accordance with yet another embodiment of the present invention.
Figure 19B:
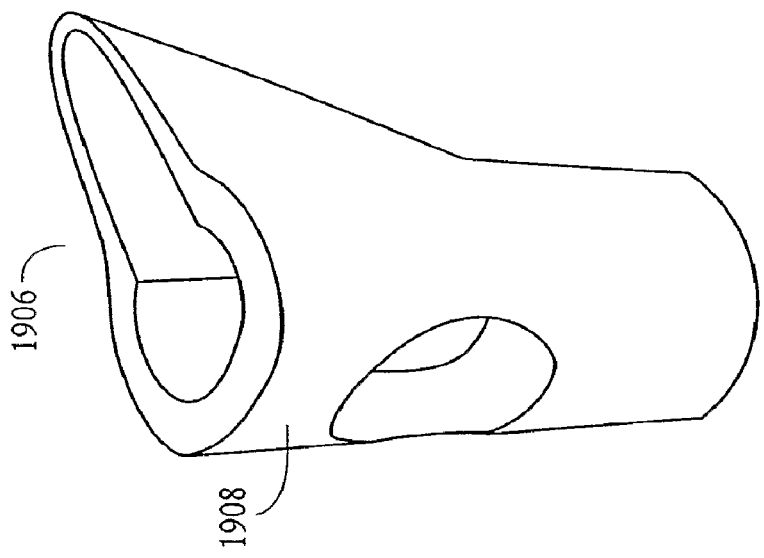
FIG. 19B illustrates a representation of a perspective view of a support sleeve for an intramedullary rod in accordance with still another embodiment of the present invention.
Figure 19A:
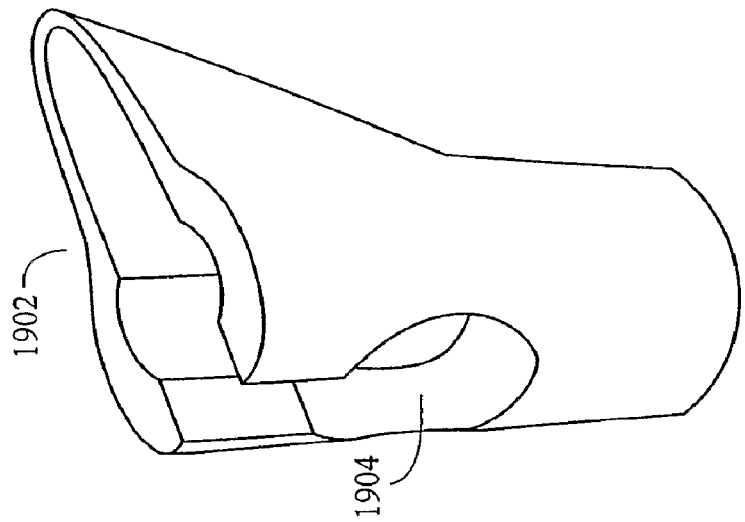
FIG. 19A illustrates a representation of a perspective view of a support sleeve for an intramedullary rod in accordance with another embodiment of the present invention.

Other embodiments of the support sleeve may also provide advantages. For example, it will be appreciated that embodiments of support sleeves with neck passages that differ from the neck slot 1812 may advantageously be used. FIG. 19A illustrates a representation of a perspective view of a support sleeve 1902 for an intramedullary rod 1502 in accordance with another embodiment of the present invention, wherein the support sleeve 1902 includes a widened area 1904 in the neck slot permitting greater lateral freedom of movement for a prosthetic femoral neck. FIG. 19B illustrates a representation of a perspective view of another embodiment of a support sleeve 1906 wherein the support sleeve 1906 includes a widened area as in the embodiment shown in FIG. 19A, but also a portion 1908 of the neck slot above the widened area is closed off. FIG. 19C illustrates a representation of a perspective view of another embodiment of a support sleeve 1910 wherein the support sleeve 1910 includes a widened area as in the embodiment shown in FIG. 19A, and includes the closed-off portion of the neck slot as in the embodiment shown in FIG. 19B, and also omits lateral walls of the neck slot in the triangular portion of the support sleeve while including a flat surface 1912 to support the prosthetic femoral neck.

Figure 20A:
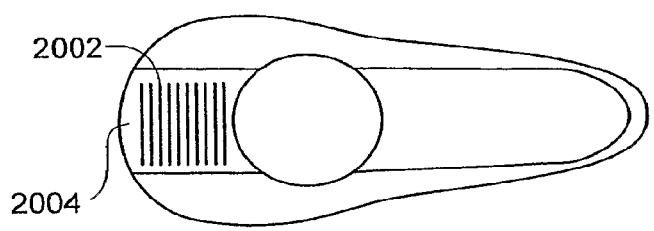
FIG. 20A illustrates a representation of a top down view of a support sleeve having ridges to engage a prosthetic femoral neck in accordance with an embodiment of the present invention.
Figure 20B:
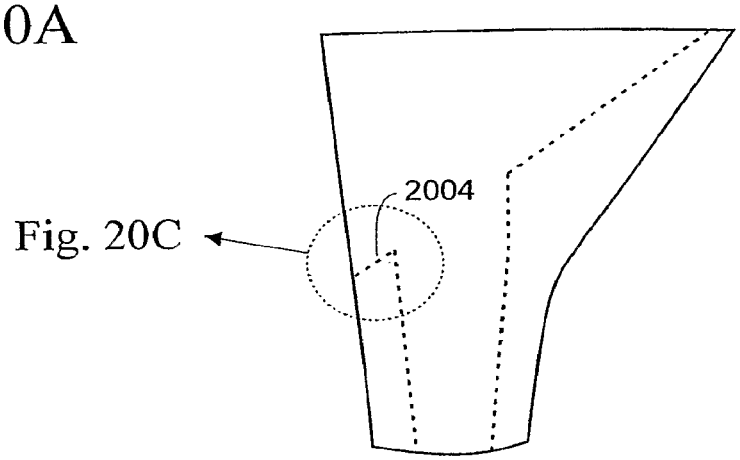
FIG. 20B illustrates a representation of a cutaway side view of a support sleeve having ridges to engage a prosthetic femoral neck in accordance with an embodiment of the present invention.
Figure 20C:
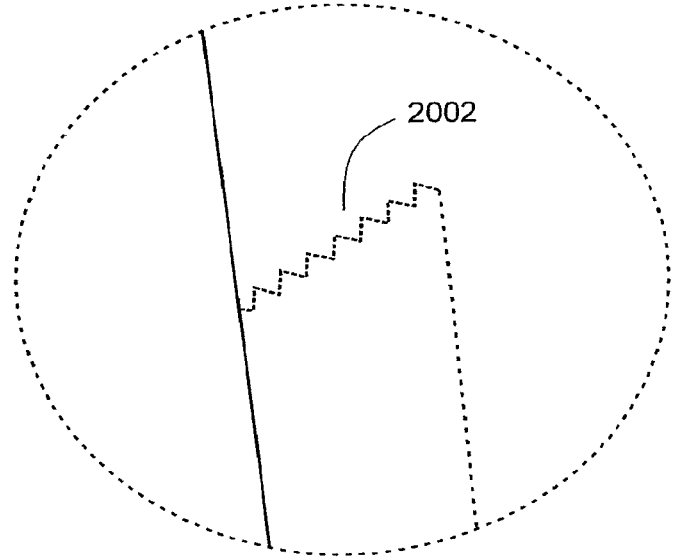
FIG. 20C illustrates a representation of a close-up view of the support sleeve having ridges to engage a prosthetic femoral neck in accordance with an embodiment of the present invention as illustrated in FIG. 20B.

Additional provisions may be made in the support sleeve to provide for fixation of a prosthetic femoral neck. FIG. 20A illustrates a representation of a top down view of a support sleeve having ridges to engage a prosthetic femoral neck in accordance with an embodiment of the present invention. FIG. 20B illustrates a representation of a cutaway side view of the support sleeve having engaging ridges, and FIG. 20C illustrates a representation of a close-up view of the engaging ridges provided in the cutaway side view of FIG. 20B. As shown in FIGS. 20A, 20B and 20C, gripping ridges 2002 may be formed along the surface of at least a portion of the slot floor 2004, preferably the portion of the slot floor 2004 extending from the wall of the sleeve opposite the triangular portion of the sleeve to the central bore. Each ridge may be perpendicular to the length of the floor of the slot and may be around 10-12 mm long and extend outward from the floor of the slot approximately 0.5 mm, and the ridges may be spaced approximately 0.5-1 mm apart. It will be appreciated that ridges of other dimensions, smaller or larger, may be formed. Advantageously, in one embodiment, the ridges grip opposing ridges that may be formed into the shaft of the prosthetic femoral neck to assist in preventing the prosthetic femoral neck from slipping or moving relative to the support sleeve.

Figure 21B:
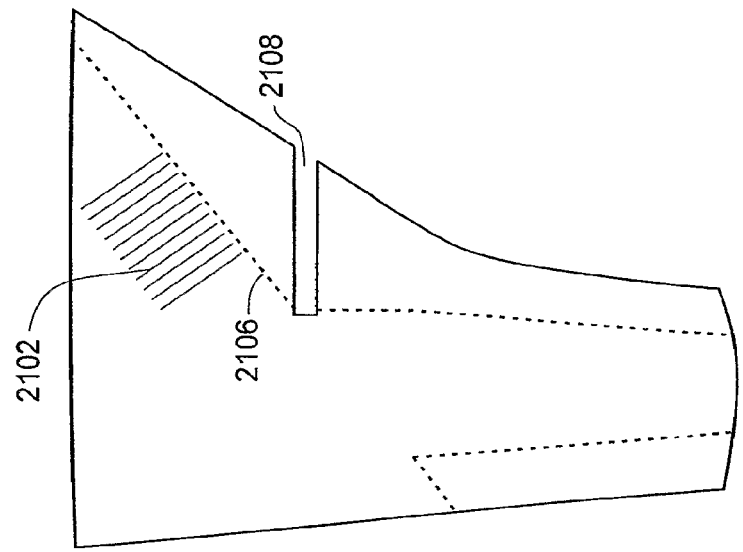
FIG. 21B illustrates a representation of a cutaway side view of a support sleeve having ridges to engage a prosthetic femoral neck in accordance with another embodiment of the present invention.
Figure 21A:
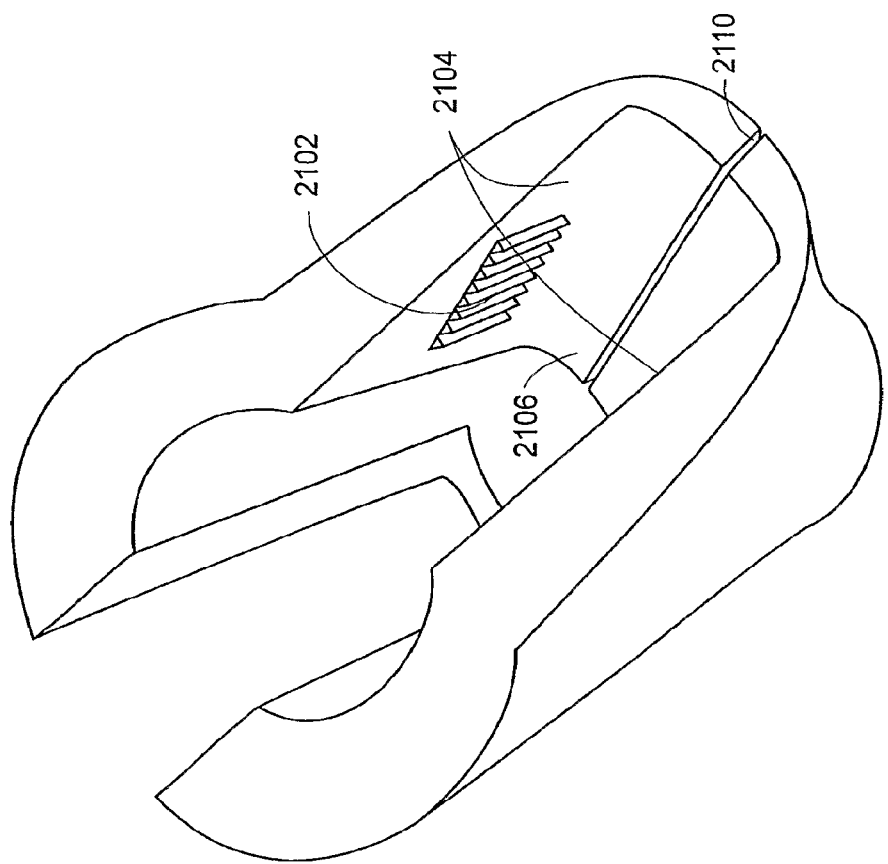
FIG. 21A illustrates a representation of a perspective view of a support sleeve having ridges to engage a prosthetic femoral neck in accordance with another embodiment of the present invention.

In another embodiment the gripping ridges may advantageously engage threads of a fixation screw fit between the shaft of the prosthetic femoral neck and the floor of the neck slot, in which position the fixation screw exerts a pressure force on both the prosthetic femoral neck and the floor of the support sleeve that may assist in preventing the prosthetic femoral neck from slipping or moving relative to the support sleeve. In another embodiment neck fixation ridges may be formed along opposing inner walls of the neck slot 1812. FIG. 21A illustrates a representation of a perspective view of a support sleeve having neck fixation ridges 2102 along the walls 2104 of a neck slot to engage a prosthetic femoral neck in accordance with another embodiment of the present invention. FIG. 21B illustrates a representation of a cutaway side view of the support sleeve having such ridges 2102 to engage a prosthetic femoral neck. The neck fixation ridges 2102 may be approximately perpendicular to the plane formed by the floor 2106 of the slot 1812, and each neck fixation ridge may be approximately 10-12 mm long and extend outward from the slot wall about 0.5 mm. The neck fixation ridges may be spaced about 0.5-1 mm apart and may be located along the surface of the inner walls 2104 of the neck slot 1812 between the central bore 1806 and the end of the slot approximately above the lower trochanter. Each neck fixation ridge may have angled flat surfaces that facilitate movement in one direction and restrict movement in the opposite direction. Accordingly, each ridge may include a restricting surface occupying a plane substantially perpendicular to a straight line running along the length of the slot floor 2004, and each ridge may also include a lower friction surface occupying a plane angled at approximately 30 degrees from the plane occupied by the inner wall of the slot, with the distance between the planes widening in the direction of the acetabulum. It will be appreciated that the neck fixation ridges 2102 may use such surfaces to permit a prosthetic femoral neck with similar, but opposing ridges formed along its shaft to travel through the neck slot 1812 in the direction of the acetabulum, and to restrict travel in the opposite direction.

In still another embodiment, one or more additional slots may be formed into the support sleeve to permit spreading of the walls 2104 of the neck slot 1812 while a ridged prosthetic femoral neck passes between them. Preferably, a first lateral slot 2108 in the support sleeve may be made from a point approximately lateral to the lower trochanter and extending laterally through the triangular portion of the neck sleeve to the central bore 1806. Also preferably, a second slot 2110 may be formed along a line bisecting the floor 2106 of the neck slot from the central rod bore outward and may extend distally through triangular portion of the neck sleeve until it meets the first lateral slot 2108. It will be appreciated that these two additional slots remove substantial matter from the support sleeve that acts to prevent the walls 2104 of the neck slot from moving relative to each other. It will also be appreciated that the force required to separate the walls 2104 of the neck slot away from each other may be regulated by their thickness, the hardness and rigidity of the material from which they are made and also by removal of matter that joins them, and that these factors may be adjusted in many ways to permit the walls 2104 of the neck slot to move an appropriate degree to allow a prosthetic femoral neck with fixation ridges to pass through the neck slot when the prosthetic femoral neck is urged with moderate force in a direction toward the acetabulum, and to substantially restrict movement of the prosthetic femoral neck in the direction away from the acetabulum.

Figure 22A:
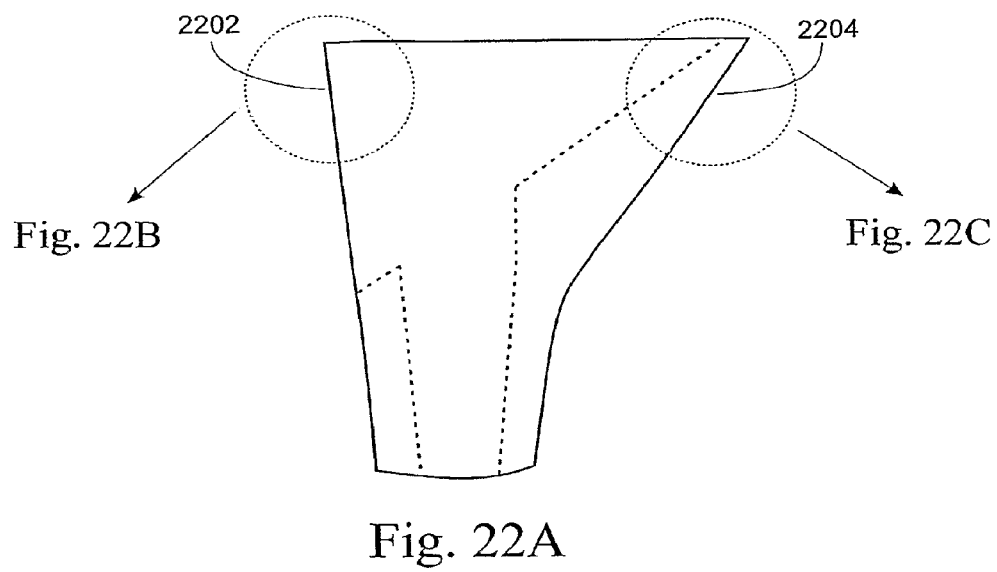
FIG. 22A illustrates a representation of a cutaway side view of a support sleeve having stepped bone-engaging outer surfaces in accordance with another embodiment of the present invention.
Figures 22B, 22C:
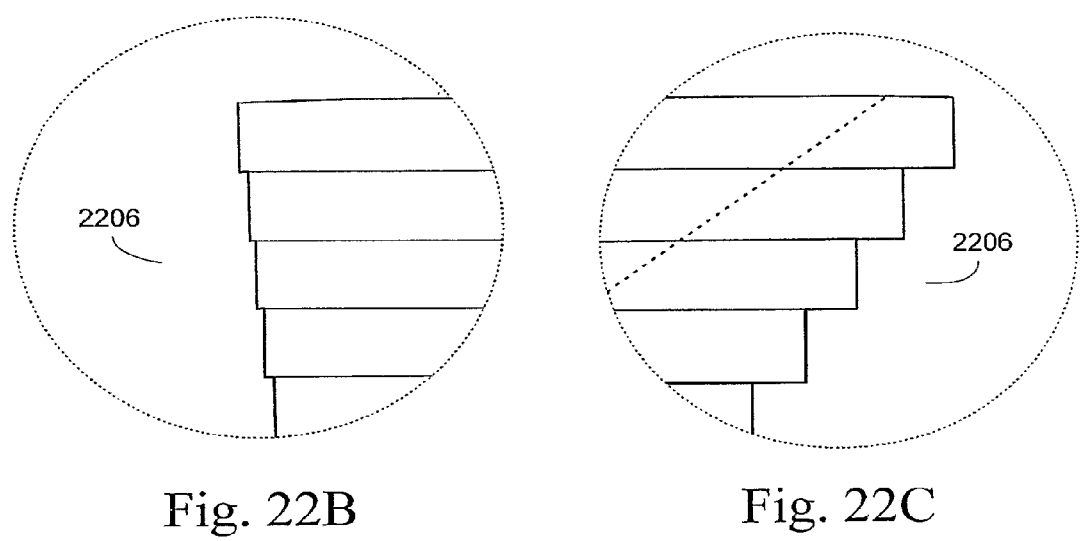
FIG. 22B illustrates a representation of a close-up view of a support sleeve having a stepped bone-engaging outer surface in accordance with an embodiment of the present invention as illustrated in FIG. 22A.
FIG. 22C illustrates a representation of a close-up view of a support sleeve having a stepped bone-engaging outer surface in accordance with an embodiment of the present invention as illustrated in FIG. 22A.

In one embodiment the surfaces of the support sleeve that rest upon the inner bone of the proximal region of the femur may be stepped. FIG. 22A illustrates a representation of a cutaway side view of a support sleeve having stepped, bone-engaging outer surfaces in accordance with another embodiment of the present invention. FIG. 22B illustrates a representation of a close-up view of a stepped, bone-engaging outer surface of a support sleeve shown in FIG. 22A, and FIG. 22C illustrates a representation of a close-up view of another stepped, bone-engaging outer surface of the support sleeve shown in FIG. 22A. As shown, the slope of the outer walls 2202, 2204 of the support sleeve, may be accommodated by a series of vertical and horizontal steps 2206, with each vertical (longitudinal) step extending approximately 2-4 mm, and each horizontal (lateral) step extending approximately 0.5-1 mm. These steps 2206 formed in the supporting surfaces may advantageously reduce shear force and convert it to downward and better-supporting compressive force. Grooved, pronged, porous and/or other surface treatments may be used independently of or to support stepped surfaces to reduce sliding and shear forces.

Figure 23A:
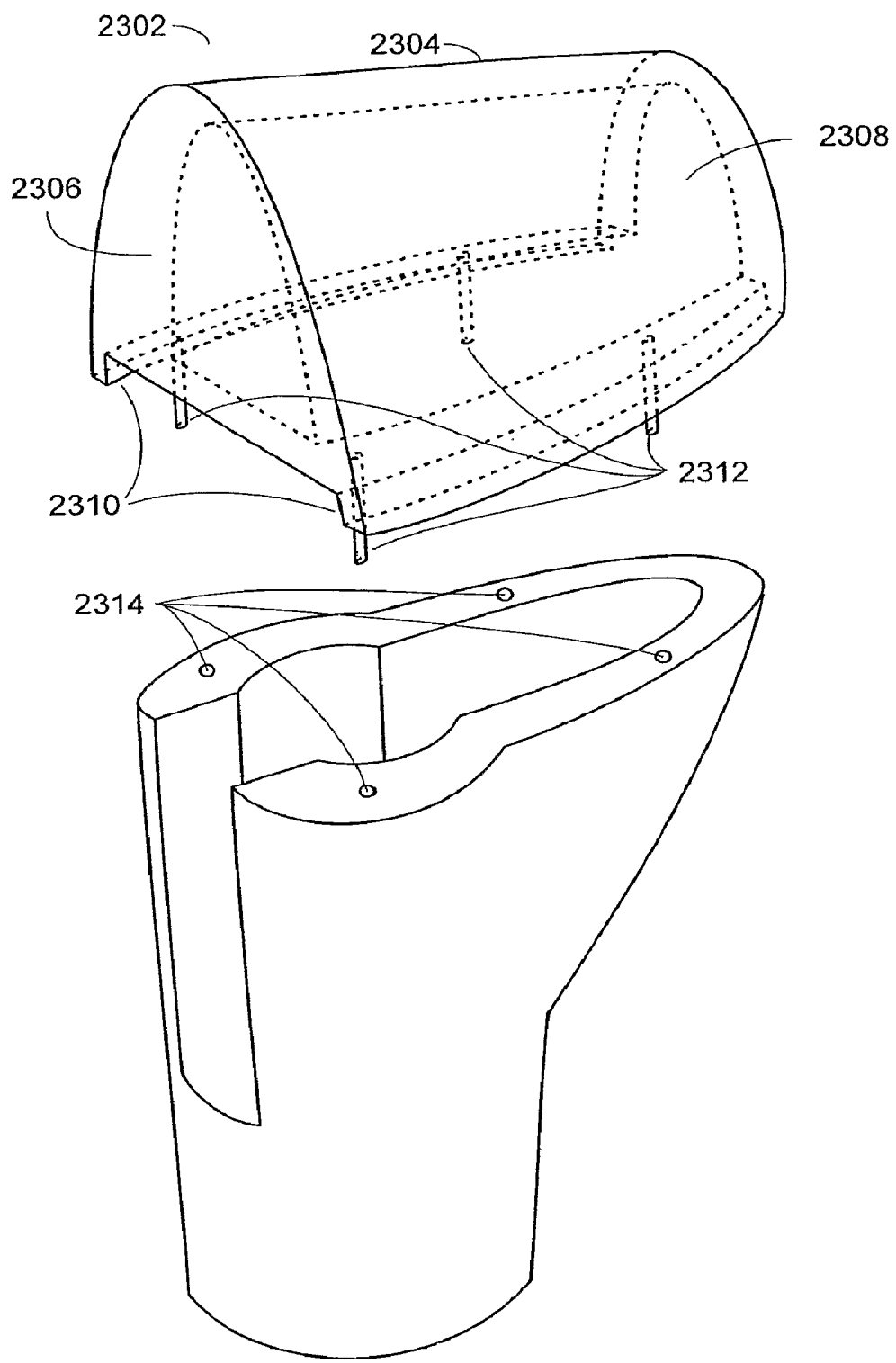
FIG. 23A illustrates a representation of a three-dimensional perspective view of a support sleeve and support sleeve cover configured to be removably joined in accordance with an embodiment of the present invention.
Figure 23B:
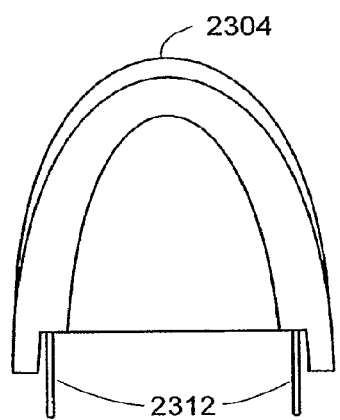
FIG. 23B illustrates a representation of a rear view of a support sleeve cover in accordance with an embodiment of the present invention.
Figure 23C:
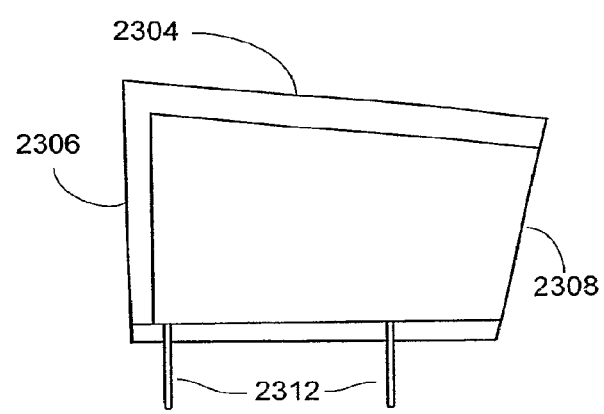
FIG. 23C illustrates a representation of a cutaway side view of a support sleeve cover in accordance with an embodiment of the present invention.
Figure 23D:
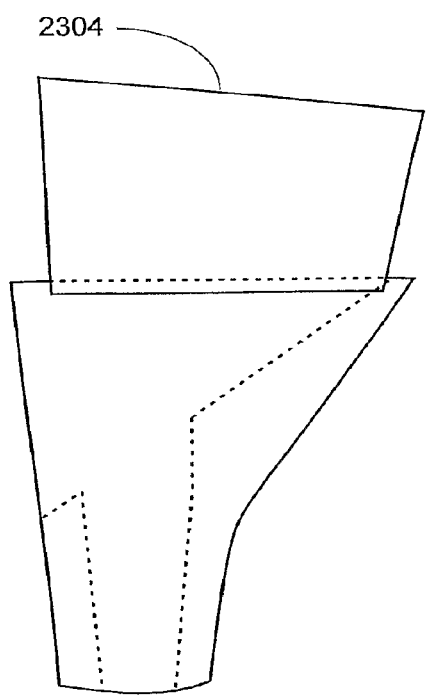
FIG. 23D illustrates a representation of a cutaway side view of a support sleeve cover removably attached to a support sleeve in accordance with an embodiment of the present invention.

In another embodiment, a support sleeve cover fits to the lateral flat surface at the proximal end of the support sleeve. FIG. 23A illustrates a representation of a perspective view of a support sleeve 1802 and support sleeve cover 2302 configured to be removably joined to the support sleeve 1802 in accordance with an embodiment of the present invention. FIG. 23B illustrates a representation of a rear view of the support sleeve cover 2302, FIG. 23C illustrates a representation of a cutaway side view of the support sleeve cover 2302, and FIG. 23D illustrates a representation of a cutaway side view of the support sleeve 2302 cover fitted to a support sleeve 1802.

The support sleeve cover 2302, when in place, advantageously supports the muscles and tissues at the proximal end of the femur, and holds them close to their original position despite removal of matter from the proximal femur. The support sleeve cover 2302, in one embodiment, includes a roughly parabolic hood 2304 which, when in place, extends laterally from the greater trochanter to the lesser trochanter. The support sleeve cover 2302 includes a wall 2306 at the end of the hood 2304 nearest the greater trochanter. At the opposite end of the hood over the lower trochanter, the support sleeve cover includes an opening 2308—in one embodiment an arched opening—which may be advantageously occupied by the prosthetic femoral neck when it is engaged with the prosthetic femoral head 1102. The support sleeve cover 2302 also includes a lip 2310 formed around its distal perimeter to engage and fit over the lateral flat surface of the support sleeve 1802. In one embodiment, cylindrical engagement pins 2312 extend distally from a flat surface inside the lip 2310. Each cylindrical engagement pin may be approximately 7-10 mm long. The cylindrical engagement pins 2312 may have a diameter of 0.5-2 mm that may be the same as the diameter of engagement bores 2314 formed into the lateral flat surface of the support sleeve. In one embodiment, four cylindrical engagement pins 2312 and four respective engagement bores 2314 are arranged in roughly a rectangular pattern about the central rod bore of the support sleeve. The engagement bores 2314 receive the cylindrical engagement pins 2312 to advantageously hold the support sleeve cover 2302 in place relative to the support sleeve 1802.

To prepare the femur 104 to receive a support sleeve 1802 in accordance with an embodiment of the present invention, the proximal end of the femur may be prepared with an osteotome, oscillating saw or other appropriate tool to remove roughly one quarter of the proximal tip of the femur. More specifically, in one embodiment, the portion to be removed is preferably that which extends laterally from the proximal tip of the greater trochanter toward the lesser trochanter and which extends distally from the tip of the greater trochanter to a point approximately 1-1.5 cm proximal to the lower trochanter. It will be appreciated that, in one embodiment, removal of this approximate quarter of the proximal tip of the femur may provide substantial access to the inner region of the proximal end of the femur, particularly to the triangular region above the lower trochanter. It will also be appreciated that differing portions of the proximal end of the femur may be removed to provide substantial access to its space without departing substantially from the methods and apparatus of the present invention.

Figure 24C:
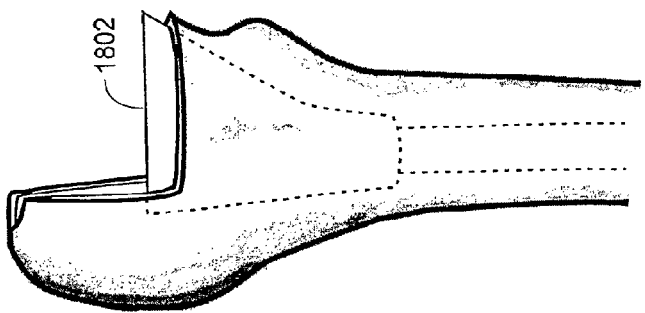
FIG. 24C illustrates a representation of a support sleeve positioned in a proximal portion of a femur in accordance with an embodiment of the present invention.
Figure 24B:
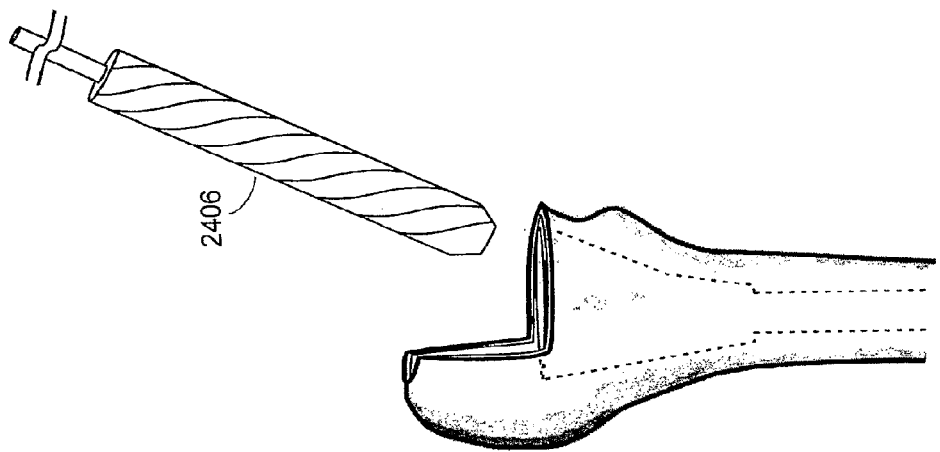
FIG. 24B illustrates a representation of a drill bit positioned above and at an angle to a proximal portion of a femur, the drill bit to remove material from the femur to facilitate positioning a support sleeve in the proximal portion of the femur in accordance with an embodiment of the present invention.
Figure 24A:
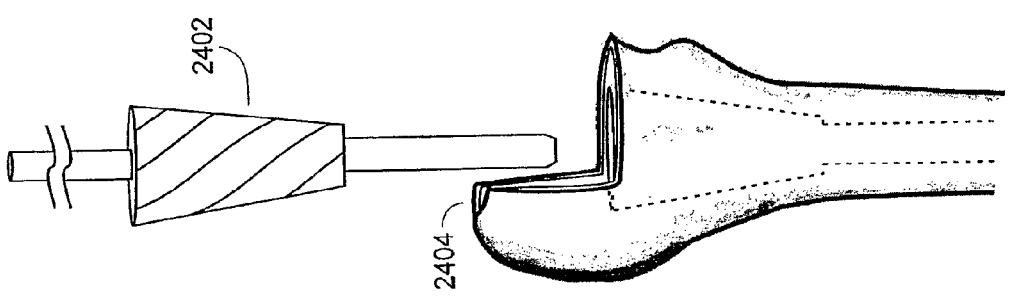
FIG. 24A illustrates a representation of a conical drill bit positioned above a proximal portion of a femur, the conical drill bit to remove material from the femur to facilitate positioning a support sleeve in the proximal portion of the femur in accordance with an embodiment of the present invention.

In one embodiment, the inner region of the proximal end of the femur may be reamed with a drilling bit having at least a distal diameter substantially the same as the diameter of the distal end of the conical portion of the support sleeve. FIG. 24A illustrates a representation of a conical drill bit 2402 positioned above a proximal portion of a femur 2404 to remove material from the femur to facilitate positioning a support sleeve in the proximal portion of the femur 2404 in accordance with an embodiment of the present invention.

The conical bit 2402 may be directed into the proximal end of the femur 2404 substantially aligned with the central canal of the femur. It will be appreciated that guiding and/or imaging tools may be used to control the angle and depth of the reaming to remove only as much material as needed to position the support sleeve.

Additional reaming may be performed with the bit directed from a point above the lower trochanter and angled approximately 30 degrees and into the center of the proximal end of the femur 2404 to remove material in roughly a triangular region to accommodate placement of the support sleeve. FIG. 24B illustrates a representation of a drill bit 2406 positioned above and at an angle to the proximal portion of the femur 2404 to optionally remove additional material from the femur to facilitate positioning the triangular portion of a support sleeve in the proximal portion of the femur 2404. In another embodiment, compaction broaching, as is known, may be used to place the support sleeve and may advantageously result in removal of less cancellous bone. FIG. 24C illustrates a representation of a support sleeve 1802 positioned in a proximal portion of a femur 2404 in accordance with an embodiment of the present invention.

It will be appreciated that, with marrow canal reaming performed such as, for example, in the manner described above in connection with FIG. 14, and with a support sleeve 1802 positioned in the proximal portion of the femur 2404, such as, for example, in the manner illustrated in FIG. 24C, that steps described above in connection with insertion of an intramedullary rod 1502 (see, for example, FIG. 17) may be performed to insert the intramedullary rod 1502 through the central rod bore 1806 of the support sleeve 1802 and into the marrow canal.

Figure 25B:
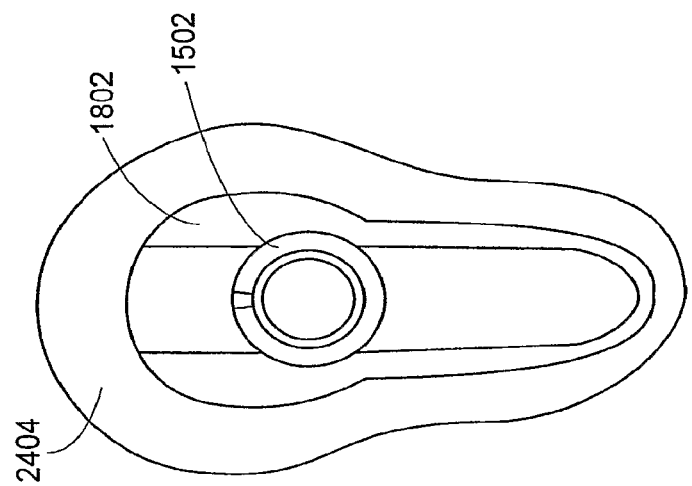
FIG. 25B illustrates a representation of a top down view of a proximal portion of a femur with a support sleeve and intramedullary rod positioned in accordance with an embodiment of the present invention.
Figure 25A:
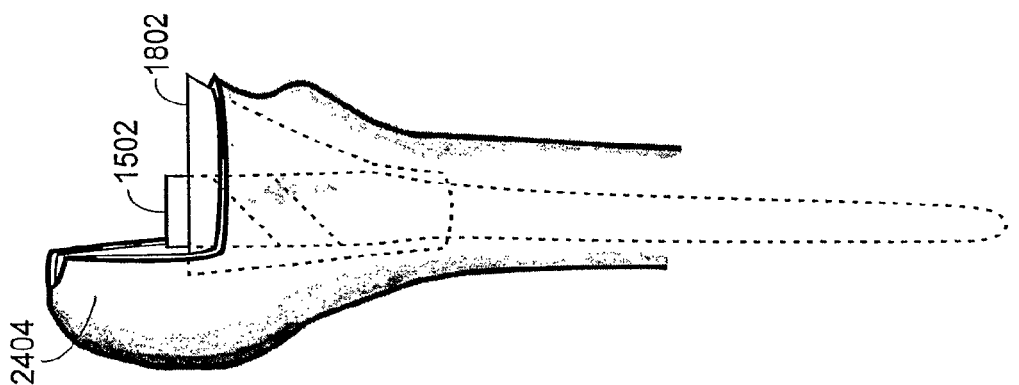
FIG. 25A illustrates a representation of a proximal portion of a femur with cutaway side view illustrating positioning of a support sleeve and intramedullary rod in accordance with an embodiment of the present invention.

FIG. 25A illustrates a representation of a proximal portion of a femur 2404 with a cutaway side view illustrating positioning of a support sleeve 1802 and an intramedullary rod 1502 inserted therethrough in accordance with an embodiment of the present invention. FIG. 25D illustrates a representation of a top down view of the proximal portion of the femur 2404 with the support sleeve 1802 in place and the intramedullary rod 1502 positioned therethrough.

Figures 26A, 26B, 26C, 26D:
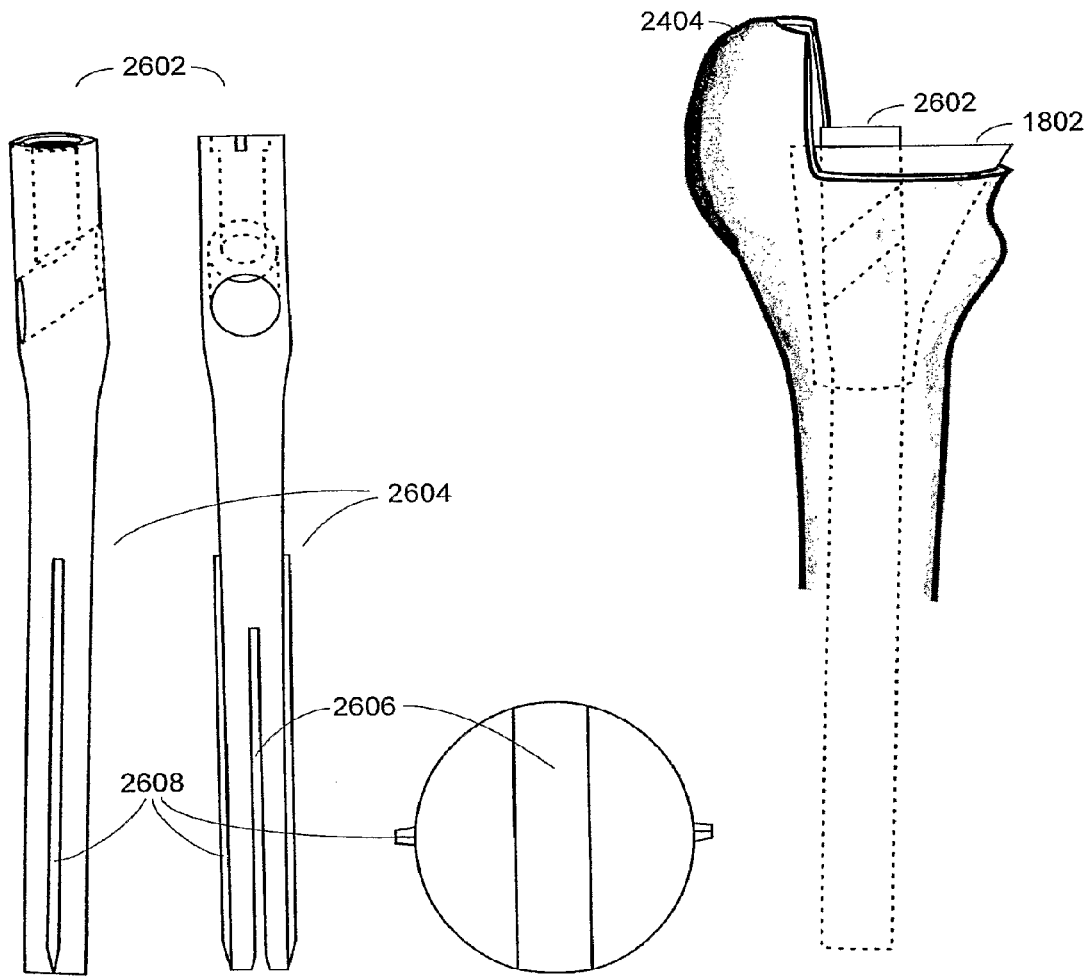
FIG. 26A illustrates a representation of a side view of an intramedullary rod having a split and fluted distal end in accordance with an embodiment of the present invention.
FIG. 26B illustrates a representation of a front view of an intramedullary rod having a split and fluted distal end in accordance with an embodiment of the present invention.
FIG. 26C illustrates a representation of a bottom up view of a split and fluted distal end of an intramedullary rod in accordance with an embodiment of the present invention.
FIG. 26D illustrates a representation of a proximal portion of a femur with cutaway side view illustrating positioning of a support sleeve and intramedullary rod having a split and fluted distal end in accordance with an embodiment of the present invention.

The present invention contemplates additional embodiments of an intramedullary rod consistent with supporting a prosthetic femoral neck introduced through the side of the femur opposite the hip joint. For example, FIG. 26 illustrates a representation of a side view of an intramedullary rod 2602 having a split and fluted distal end 2604 in accordance with an embodiment of the present invention. FIG. 26B illustrates a representation of a front view of the intramedullary rod 2602 having a split and fluted distal end 2604, and FIG. 26C illustrates a representation of a bottom up view of the split and fluted distal end 2604. In such embodiment, at least one slot 2606 is formed in the distal end 2604 of the intramedullary rod 2602, and extends from the tip of the distal end 2604 longitudinally along the shaft of the intramedullary rod 2602 for approximately 15% to 75% of the length of the intramedullary rod 2602. The slot 2606 may be approximately 2-10 mm wide, but could be wider or narrower. It will be appreciated that a slotted distal end forms one or more prongs, depending on the number of slots, such as, for example, four prongs created by two intersecting slots, or three prongs created by two parallel slots.

The distal end 2604 of the intramedullary rod 2602 may also include one or more flutes 2608 formed along the outside of the shaft of the distal end 2604. The flute 2608 extends approximately 1-3 mm from the surface of the shaft in the direction perpendicular to the length of the shaft. The flute 2608 may be approximately 1-5 mm wide, but could be wider or narrower. Lengthwise, the flute 2608 may extend approximately the length of the slot 2606, but may be shorter or longer. In one embodiment, the flute may be a projection (as shown in FIGS. 26A-C) extending away from the center of the shaft, and in another embodiment, the flute may be a recess or groove formed into the shaft toward the center of the shaft. FIG. 26D illustrates a representation of a proximal portion of a femur 2404 with cutaway side view illustrating positioning of a support sleeve 1802 and intramedullary rod 2602 having a split and fluted distal end 2604 inserted therethrough.

In one such embodiment, the intramedullary rod 2602 may have a stem portion with a larger diameter, preferably in the range of 10-13 mm, and may be cylindrical in shape with little or no narrowing distally. The slot 2606 may bisect the stem from its distal end 2604 and may preferably extend proximally approximately 6-10 cm. The slot may also preferably be approximately 1-5 mm wide. The slotted stem may advantageously reduce stress along the length of the femur 104 and also provide superior fill within the femoral canal. The one or more flutes may also advantageously cut into the interior bony walls of the femoral canal to provide additional fill and also to provide rotational resistance between the intramedullary rod 2602 and the femur 104. It will be appreciated that these variations in the stem of the intramedullary rod may be used with either a longer or shorter proximal region.

It will be understood that the use of the support sleeve in combination with an intramedullary rod achieves high levels of fit and fill within the femur 104 both proximally and distally. It is further contemplated that a total hip replacement kit in accordance with the present invention may include a number of support sleeves of gradually increasing dimensions and may also include a number of intramedullary rods of gradually increasing dimensions. The dimensions of the central bore of each of the support sleeves may, however, remain fixed to firmly engage the proximal region of any of the intramedullary rods, the diameter and shape of which may also remain constant among all of the intramedullary rods. As contemplated, the variety of combinations of support sleeve and intramedullary rod provided by the kit further advantageously permits even greater, patient-specific fit and fill of the prosthetics to the femur both proximally and distally.

In another embodiment, an intramedullary rod includes a proximal region having dimensions substantially similar to those described above in connection with various support sleeves. This embodiment may also include a stem in any of the variations described above. FIG. 27A illustrates a representation of a side view of an intramedullary rod 2702 with proximal femoral support structure in accordance with an embodiment of the present invention, and FIG. 27B illustrates a representation of a front view of the intramedullary rod 2702. FIG. 27C illustrates a representation of a top down view of the intramedullary rod 2702 with proximal femoral support structure, and FIG. 27D illustrates a representation of a bottom up view of a split and fluted distal end of an intramedullary rod 2702 with proximal femoral support structure. In accordance with this embodiment, the proximal region of the intramedullary rod 2702 includes a neck bore 2704 and a fixation bore 2706, and also includes a circular keyway 2708, which may be formed as described above in connection with FIG. 15C. As will be readily appreciated, the femur preparation and reaming steps described above in connection with intramedullary rod and support sleeve may be used to prepare the femur 104 to receive such embodiment of the intramedullary rod 2702. This embodiment provides advantages of the support sleeves and intramedullary rods described above without using a separate sleeve. In addition, the neck bore 2704 may advantageously be formed to be wider at the insertion 2710 and exit 2712 points of the neck bore 2704, permitting adjustment of the angle of the prosthetic femoral neck in relation to the intramedullary rod 2702.

A prosthetic femoral neck in accordance with the present invention may be essentially a straight shaft, which may be slightly tapered on one end to fixedly join a prosthetic femoral head by insertion into a neck bore (see FIG. 11 and related description). In one embodiment, a prosthetic femoral neck may have a circular cross section. It will be appreciated that the cross-sectional shape may differ, and other embodiments are specifically contemplated such as, for example, oval, square, rectangular, triangular, irregular or other cross-sectional shapes may be used, where the shape of the neck bore in the intramedullary rod is configured to correspondingly receive a prosthetic femoral neck having such cross-sectional shape. While a circular cross-section of a head-engaging end of a prosthetic femoral neck may be used with the remainder of the prosthetic femoral neck having a different cross-sectional shape, in another embodiment the neck-receiving bore in the prosthetic femoral head may be configured to receive a head-engaging end of a prosthetic femoral neck having a cross-sectional shape other than circular. In addition, a prosthetic femoral neck may include fixation ridges formed therein to fix its position relative to an intramedullary rod. In one embodiment, the fixation ridges may be formed roughly perpendicular to the lengthwise direction of the shaft of the prosthetic femoral neck to engage the fixation ridges described above in connection with FIGS. 20A, B, C and 21A, B. In another embodiment, a prosthetic femoral neck may be curved and/or may include fixation grooves. FIG. 27E illustrates a representation of a side view of a curved prosthetic femoral neck 2720 having preconfigured fixation grooves 2722 to fix the position of the prosthetic femoral neck 2720 relative to an intramedullary rod in accordance with an embodiment of the present invention. FIG. 27F illustrates a representation of a top down view of a curved prosthetic femoral neck 2720 having preconfigured fixation grooves 2722, and FIG. 27G illustrates a representation of a bottom up view of a curved prosthetic femoral neck 2720 having preconfigured fixation grooves 2722. It will be appreciated that the prosthetic femoral neck 2720 may be used to facilitate advantageous angling of the femoral head in relation to the intramedullary rod and also may be used for right or left hip joint repair simply by flipping it upside down.

FIG. 27H illustrates a representation of an upper portion of an example of an intramedullary rod 2724 having a neck bore 2726 with at least one groove-engaging ridge 2728 configured to be used with a prosthetic femoral neck, such as prosthetic femoral neck 2720, having fixation grooves 2722. FIG. 27I illustrates a representation of a top down view of the intramedullary rod 2724 having a neck bore and a prosthetic femoral neck 2720 having fixation grooves 2722 inserted through the neck bore. It will be readily appreciated that a fixation bolt threaded into the fixation bore 1512 may provide force that causes the fixation grooves 2722 to engage the ridges 2728 to fix the position of the prosthetic femoral neck relative to the intramedullary rod 2724.

Figures 28A, 28B, 28C, 28D, 28E:
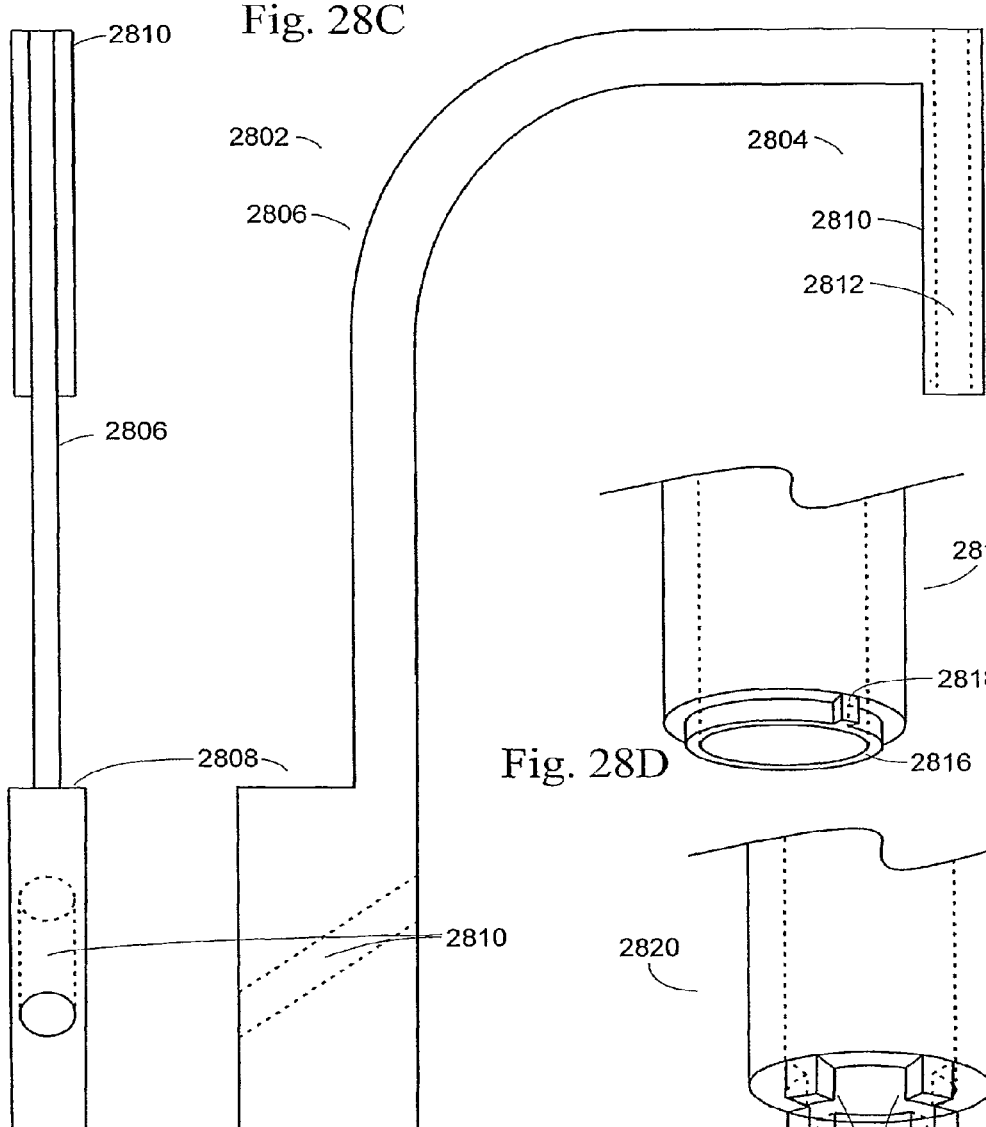
FIG. 28A illustrates a representation of a side cutaway view of a neck bore guide tool in accordance with an embodiment of the present invention.
FIG. 28B illustrates a representation of a rear cutaway view of a neck bore guide tool in accordance with an embodiment of the present invention.
FIG. 28C illustrates a representation of a top down view of a neck bore guide tool in accordance with an embodiment of the present invention.
FIG. 28D illustrates a representation of a perspective cutaway view of a fixation keyway of a neck bore guide tool for engaging a proximal end of an intramedullary rod in accordance with an embodiment of the present invention.
FIG. 28E illustrates a representation of a perspective cutaway view of a fixation keyway of a neck bore guide tool for engaging a proximal end of an intramedullary rod in accordance with another embodiment of the present invention.

With the intramedullary rod in place, and with support sleeve if one is used, attention is then turned to insertion of the prosthetic femoral neck. An alignment tool may advantageously be fixed to the intramedullary rod to provide an accurate guide for drilling a straight bore to meet the path defined by the neck bore in the intramedullary rod, thereby facilitating straightforward insertion of the prosthetic femoral neck. FIG. 28A illustrates a representation of a side cutaway view of a neck bore alignment tool 2802 in accordance with an embodiment of the present invention. FIG. 28B illustrates a representation of a rear view of the neck bore alignment tool 2802, and FIG. 28C illustrates a representation of a top down view of the neck bore alignment tool 2802. FIG. 28D illustrates a representation of a perspective cutaway view of a keyway of the neck bore alignment tool 2802 for engaging a proximal end of an intramedullary rod 1502. FIG. 28E illustrates a representation of a perspective cutaway view of an alternative keyway 2820 for engaging a proximal end of an intramedullary rod 1502.

The alignment tool 2802 has a rod-engaging end 2804, a curving handle section 2806, and a guide block 2808 that includes a guide bore 2810. The rod-engaging end 2804 comprises a cylindrical shaft 2812 approximately 4-8 cm in length and approximately 1.5 to 2 cm in diameter. The cylindrical shaft 2812 includes a fixation bore 2814 extending the full length of the shaft, and the fixation bore 2814 may have a diameter of approximately 8 mm, but that diameter could be more or less.

The rod-engaging end 2804 of the alignment tool 2802 includes a keyway 2814 located at its end. The keyway 2814 includes a recessed circular rim 2816 and a protrusion 2818 projecting outward from the rim 2816. The circular rim 2816 is recessed about 2 mm inward from the outer surface of the cylindrical shaft 2810. The protrusion 2818 is approximately 2 mm wide and projects approximately 2 mm outward from the rim 2816. It will be appreciated that the approximately 2 mm protrusion along the circular rim 2816 of the keyway 2814 may advantageously engage the 2 mm notch in the circular keyway 1514 at the proximal end of the intramedullary rod 1502 to prevent rotation of the alignment tool 2802 with respect to the intramedullary rod 1502.

As illustrated in FIG. 28E, an alternative keyway 2820 includes four protrusions extending from the end of the cylindrical shaft 2812. The four protrusions may be approximately 2 mm long and 2 mm wide. It will be appreciated that the keyway 2820 may advantageously engage the intramedullary rod keyway 1516 (see FIG. 15D) to prevent the alignment tool 2802 and intramedullary rod 1502 from rotating relative to each other about an axis running through the longitudinal center of their respective fixation bores 2812, 1512. It will be appreciated that other, differentially structured keyways could be used to prevent such rotation.

Figure 29A:
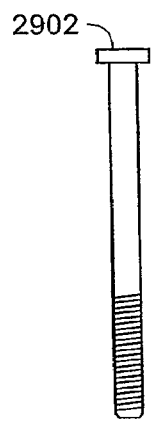
FIG. 29A illustrates a representation of a fixation bolt for joining an end of a neck bore guide tool to an end of an intramedullary rod in accordance with an embodiment of the present invention.
Figure 29B:
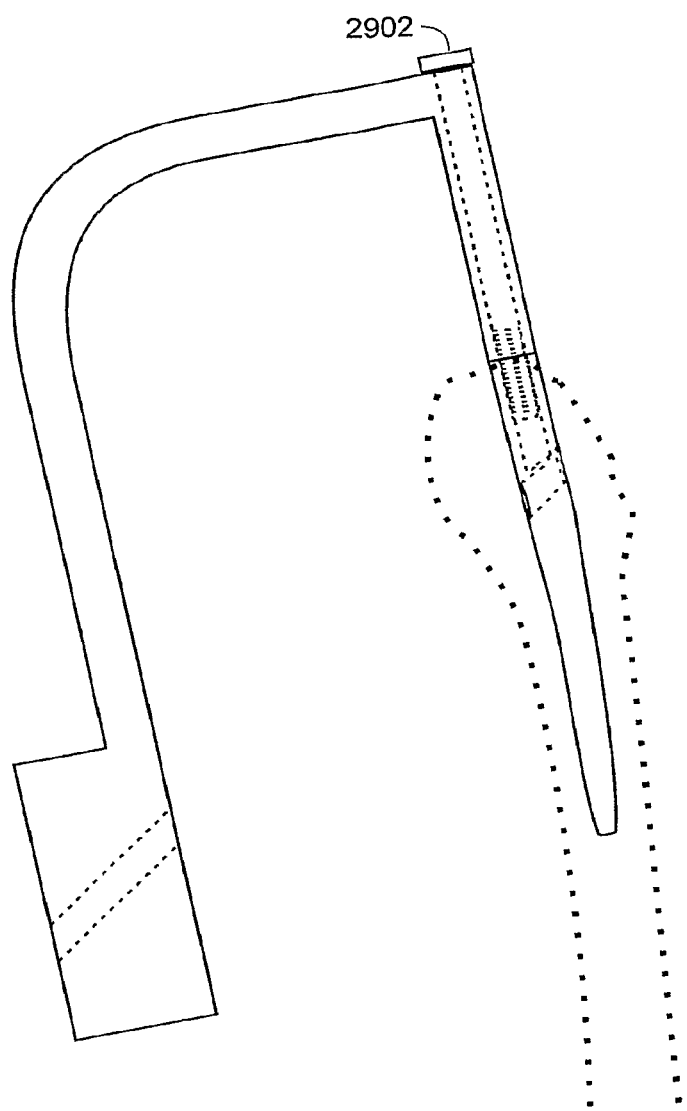
FIG. 29B illustrates a representation of a cutaway side view of a neck bore guide tool removably joined with a fixation bolt and interlocking keyway to a proximal end of an intramedullary rod in accordance with an embodiment of the present invention.

When the circular keyway of the alignment tool is properly engaged with the circular keyway of the intramedullary rod, a fixation bore of the alignment tool is aligned to the fixation bore of the intramedullary rod, and a fixation screw may be introduced through the alignment bore of the alignment tool and rotationally threaded into the fixation bore of the intramedullary rod. FIG. 29A illustrates a representation of a fixation screw 2902 for joining the rod-engaging end 2804 of the alignment tool 2802 to an end of an intramedullary rod 1502 that has been inserted into a femur 104 in accordance with an embodiment of the present invention. FIG. 29B illustrates a representation of a cutaway side view of the alignment tool 2802 removably joined with the fixation bolt 2902 and interlocking keyways (e.g., 2814, 1514) to a proximal end of the intramedullary rod 1502. As will be readily appreciated, the head of the fixation screw 2902 may be machined to be engaged by a straight edge, Phillips-type, hexagonal or other shaped rotational driver. Using an appropriate rotational driver, the fixation screw 2902 may be tightened to securely fix the position of the alignment tool 2802 with respect to the intramedullary rod 1502.

When the alignment tool 2802 is properly fixed relative to the intramedullary rod 1502, a guide bore 2810 of the alignment tool 2802 provides a path such that a straight shaft inserted through the guide bore 2810 and toward the patient's leg will pass through the neck bore 1504 in the proximal end of the intramedullary rod 1502 that has been positioned within the femur. The guide bore 2810 advantageously facilitates introduction of a straight guide wire from a point on the side of the patient's leg below the proximal femur through skin and subcutaneous tissue, into the femur, through the neck bore 1504 of the intramedullary rod 1502, out of the femur and toward the neck-engaging bore 1114 of the prosthetic femoral head 1102. It will be appreciated that imaging may be used to confirm proper location of the guide wire.

Figure 30:
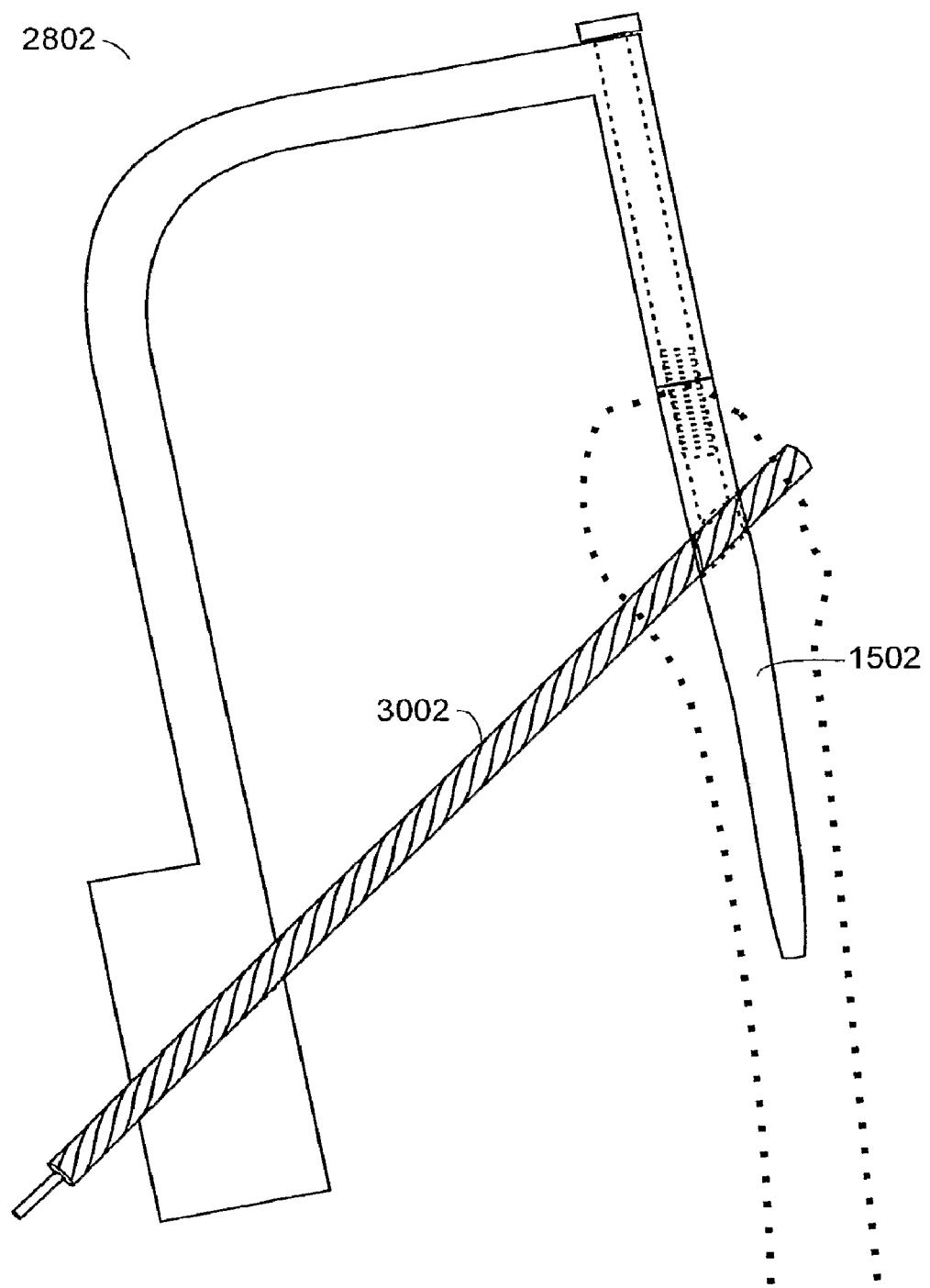
FIG. 30 illustrates a representation of a cutaway side view of a neck bore guide tool removably joined with a fixation bolt and interlocking keyway to a proximal end of an intramedullary rod and with a neck bore drill bit guided through the neck bore guide tool and through the proximal femur and through the neck bore of the intramedullary rod in accordance with an embodiment of the present invention.

After any adjustment or alignment suggested by the guide wire, a drill bit having a diameter sufficient to accommodate the largest diameter of the prosthetic femoral neck may be introduced into the guide bore of the alignment tool. In one embodiment, the guide bore has a diameter approximately the same as the neck bore in the intramedullary rod. Alternatively, a series of drill bits stepped in size may be used to gradually increase the diameter of the bore to a size sufficient for the prosthetic femoral neck. FIG. 30 illustrates a representation of a cutaway side view of the alignment tool 2802 removably joined with the fixation screw 2902 and interlocking keyway (e.g., 2814, 1514) to the proximal end of the intramedullary rod 1502 and with a neck bore drill bit 3002 guided through the guide bore 2810 of the alignment tool 2802 and through the proximal femur and through the neck bore 1504 of the intramedullary rod 1502 in accordance with an embodiment of the present invention. It will be understood that a drill motor may rotate the neck bore drill bit 3002 as it is introduced into the guide bore 2810 to create a neck insertion bore. In creating the neck insertion bore, the rotating neck bore drill bit 3002 is introduced through the guide bore 2810, into the leg of the patient, into the femur, through the neck bore 1504 of the intramedullary rod 1502 and through the other side of the femur. Accordingly, the neck-insertion bore creates a path through the femur, through which the prosthetic femoral neck may be advantageously introduced from one side of the femur and through the neck bore 1504 in the intramedullary rod 1502 such that the head-engaging end of the prosthetic femoral neck may engage the prosthetic femoral head 1102 on the opposite side of the femur. With the neck-insertion bore created, the alignment tool 2802 may be detached by loosening the fixation screw 2902 and removing the alignment tool 2802.

In one embodiment, a neck-sizing shaft may advantageously be introduced through the neck insertion bore to determine the optimal length of the prosthetic femoral neck. The neck-sizing shaft may be of similar diameter to the prosthetic femoral neck. However, a head-engaging end of the neck-sizing shaft may be of slightly smaller diameter than that of the actual prosthetic femoral neck to avoid fixedly engaging the prosthetic femoral head 1102 and to thereby facilitate removal of the neck-sizing shaft after trial fitting. The neck-sizing shaft may be introduced through the neck insertion bore such that the head-engaging end of the neck-sizing shaft enters the neck bore 1114 of the prosthetic femoral head 1102 and thereby engages the prosthetic femoral head 1102. Holding the femur steady and with moderate force applied to the neck-sizing shaft in the direction of the hip joint, a fixation screw 2902 may be threaded into the fixation bore 1512 of the intramedullary rod 1502 and tightened to fix the neck-sizing shaft relative to the intramedullary rod 1502. The fit and positioning of the prosthetic femoral neck and femur relative to the hip may then be tested, and by loosening the fixation screw 2902 and adjusting the neck-sizing shaft and retightening the fixation screw 2902, additional fit testing may determine an optimal length of the prosthetic femoral neck. When fit is deemed optimal, predetermined length markings along the neck-sizing shaft may be consulted to determine the proper length for the prosthetic femoral neck. The proper length of the prosthetic femoral neck preferably provides proper distance and angle between the femur 104 and acetabulum and provides a length of approximately 1-2 mm of the prosthetic femoral neck protruding outside the femur on the side of the femur away from the patient's hip.

Figure 31:
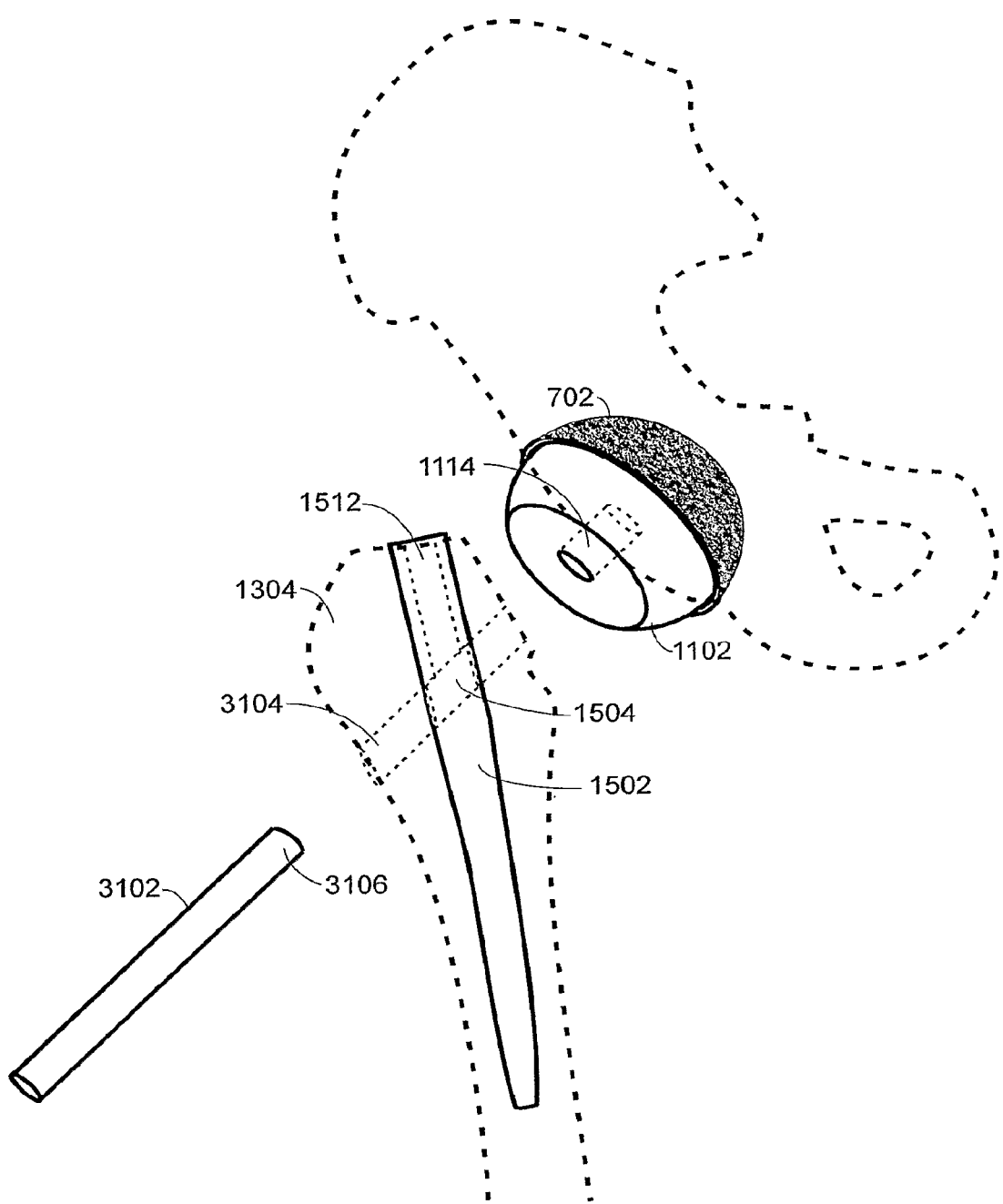
FIG. 31 illustrates a representation of a prosthetic acetabular cup, a prosthetic femoral head, an intramedullary rod positioned in a femur, and also illustrates a prosthetic femoral neck positioned for insertion within the neck bore of the intramedullary rod in accordance with an embodiment of the present invention.

The neck-sizing shaft may then be removed and a prosthetic femoral neck of proper length may be selected. FIG. 31 illustrates a representation of a prosthetic acetabular cup 812, a prosthetic femoral head 1102, an intramedullary rod 1502 positioned in a femur, and also illustrates a prosthetic femoral neck 3102 positioned for insertion within a neck insertion bore 3104 that includes the neck bore 1504 of the intramedullary rod 1502 in accordance with an embodiment of the present invention. The slightly tapered head-engaging end 3106 of the selected prosthetic femoral neck 3102 is then inserted into the neck-insertion bore 3104 and positioned through the femur 3104 and the neck bore 1504 of the intramedullary rod 1502 such that the head-engaging end 3106 of the prosthetic femoral neck 3102 engages the neck bore 1114 in the prosthetic femoral head 1102. The prosthetic femoral neck 3102 may be impacted into position in the neck bore 1114 of the prosthetic femoral head 1102 by one or more sharp taps delivered using an appropriate driving tool to the non-engaging end of the prosthetic femoral neck 3102. The prosthetic femoral neck 3102 may then be securely fixed relative to the intramedullary rod 1502 by tightening a fixation screw 2902 through the fixation bore 1512 of the intramedullary rod 1502 to firmly hold the shaft of the prosthetic femoral neck 3102 in place within the neck bore 1504 of the intramedullary rod 1502.

Figure 32A:
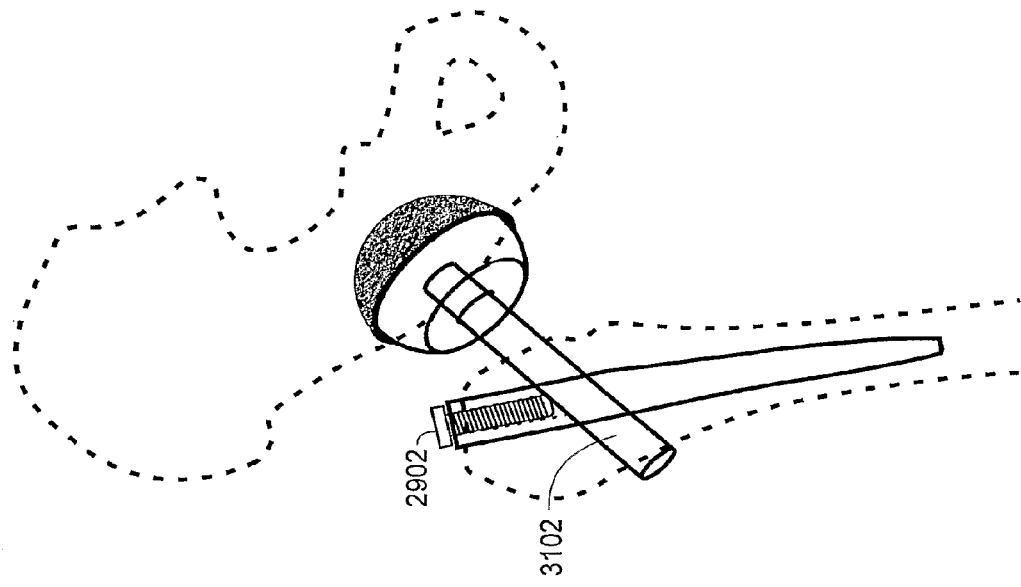
FIG. 32A illustrates a representation of a prosthetic acetabular cup, a prosthetic femoral head and neck, and an intramedullary rod installed in a femur, and also illustrates a representation of a fixation screw to fix the position of the prosthetic femoral neck within the neck bore of the intramedullary rod in accordance with an embodiment of the present invention.
Figure 32B:
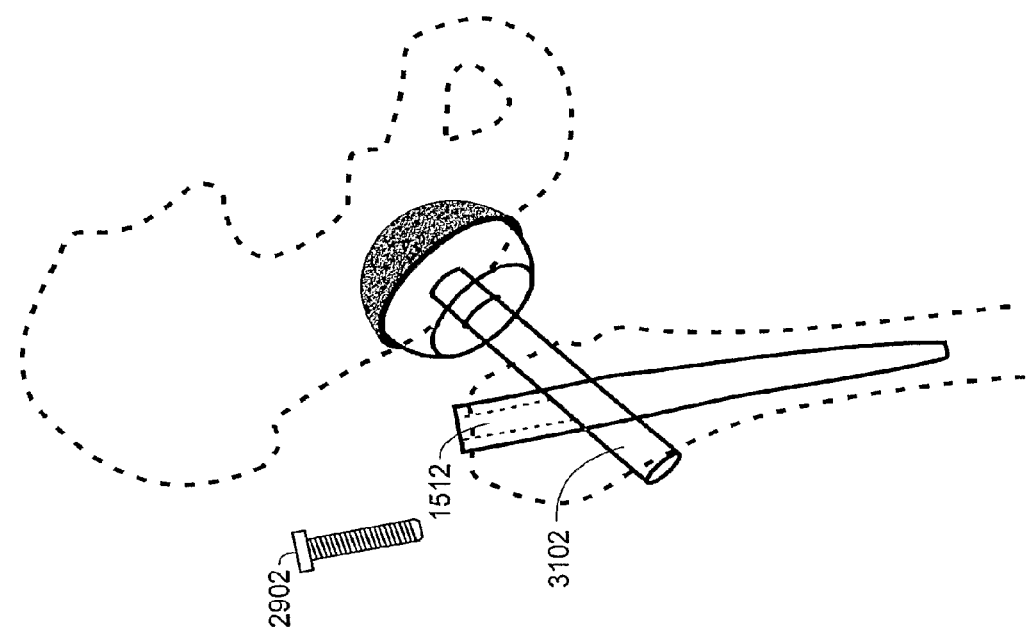
FIG. 32B illustrates a representation of a prosthetic acetabular cup, a prosthetic femoral head and neck, and an intramedullary rod installed in a femur, and also illustrates a representation of a fixation screw fixing the position of the prosthetic femoral neck within the neck bore of the intramedullary rod in accordance with an embodiment of the present invention.

FIG. 32A illustrates a representation of a prosthetic acetabular cup, a prosthetic femoral head and neck, and an intramedullary rod installed in a femur, and also illustrates a representation of a fixation screw 2902 to fix the position of the prosthetic femoral neck 3102 within the neck bore of the intramedullary rod in accordance with an embodiment of the present invention. FIG. 32B illustrates a representation of a fixation screw fixing 2902 the position of the prosthetic femoral neck 3102 within the neck bore of the intramedullary rod.

It will also be appreciated, as exemplified by embodiments described above, that ridges or grooves may be formed into the shaft of the prosthetic femoral neck 3102 to engage opposing ridges or grooves formed in the neck bore 1504 of the intramedullary rod 1502 and/or ridges or grooves formed in a support sleeve 1802 (see, e.g., FIGS. 20A,B,C and 21A,B and 27E,F,G,H,I), and it will be appreciated that engaging force may provided by the fixation screw 2902 forcing the ridges or grooves in the prosthetic femoral neck 3102 against the opposing ridges or grooves.

With the prosthetic femoral neck 3102 advantageously fixed in position, the surgical access incisions may then be closed in accordance with known technique.

Figure 33:
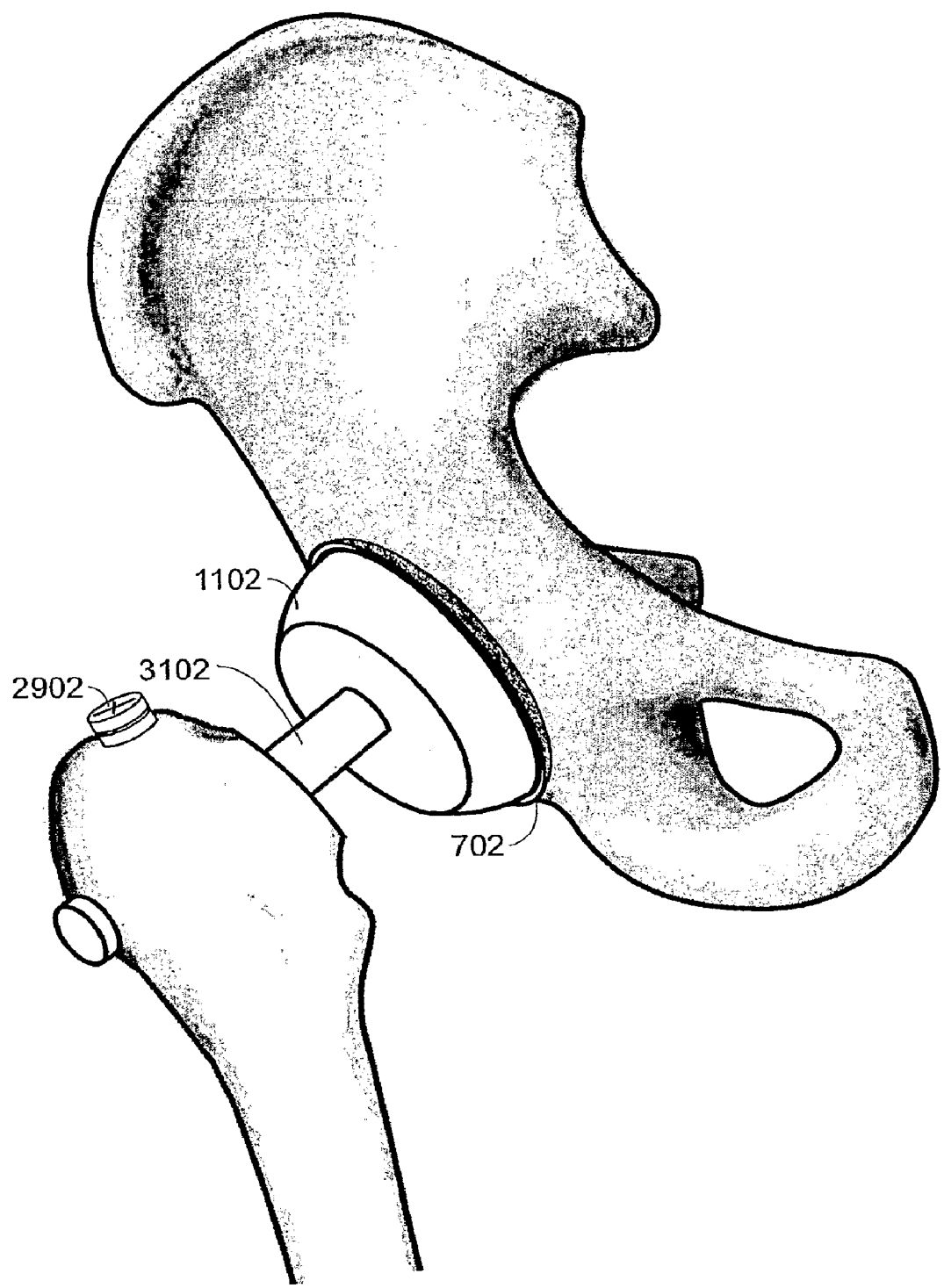
FIG. 33 illustrates a representation of a three-dimensional view of a prosthetic acetabular cup, a prosthetic femoral head and neck, and an intramedullary rod installed in a femur with a fixation screw fixing the position of the prosthetic femoral neck in accordance with an embodiment of the present invention.

FIG. 33 illustrates a representation of a three-dimensional view of a prosthetic acetabular cup 812, a prosthetic femoral head 1102 and neck 3102, and an intramedullary rod installed in a femur with a fixation screw 2902 fixing the position of the prosthetic femoral neck 3102 in accordance with an embodiment of the present invention. With the prosthetic femoral neck 3102 fixedly joined to the prosthetic femoral head 1102, and with the prosthetic femoral neck 3102 fixed with respect to the intramedullary rod, the femur is advantageously positioned in approximately normal rotational capacity with respect to the acetabulum. It will be appreciated that normal rotational capacity, i.e., the degree of comfortable rotational movement under various day-to-day stress loads that was available to a patient prior to injury or deterioration of the hip joint, differs from patient to patient, based, for example, on age, anatomy and lifestyle, and it will also be appreciated that a rotational capacity facilitated by the various embodiments of the present invention may usefully approximate a normal rotational capacity even though a resulting degree of movement may be different than normal rotational capacity.

Figure 34:
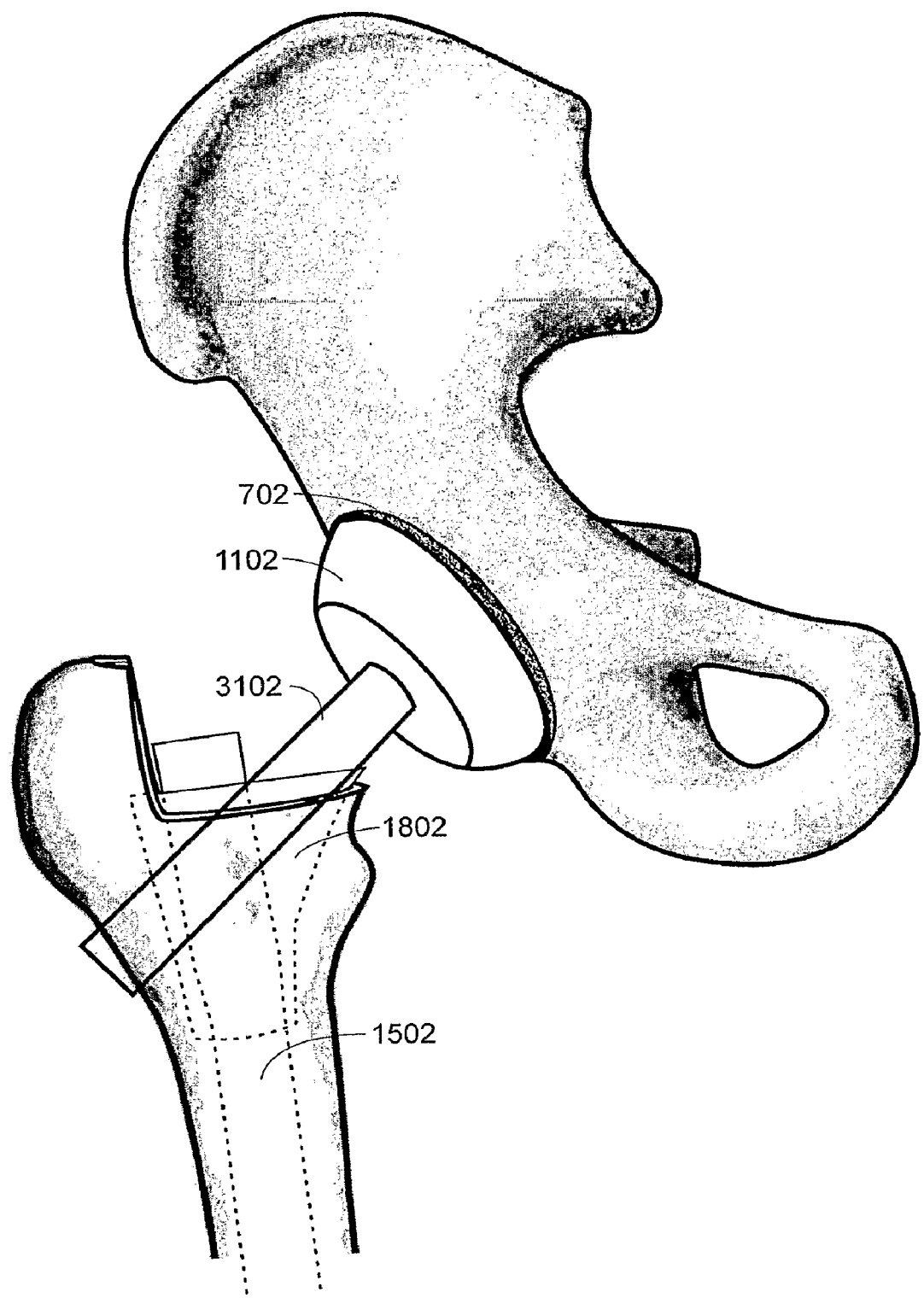
FIG. 34 illustrates a representation of a prosthetic acetabular cup, a prosthetic femoral head and neck, and an intramedullary rod installed in a support sleeve in the proximal femur in accordance with an embodiment of the present invention.
Figure 35A:
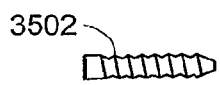
FIG. 35A illustrates a representation of a fixation screw for fixing the prosthetic femoral neck in relation to the support sleeve and intramedullary rod in accordance with an embodiment of the present invention.
Figure 35B:
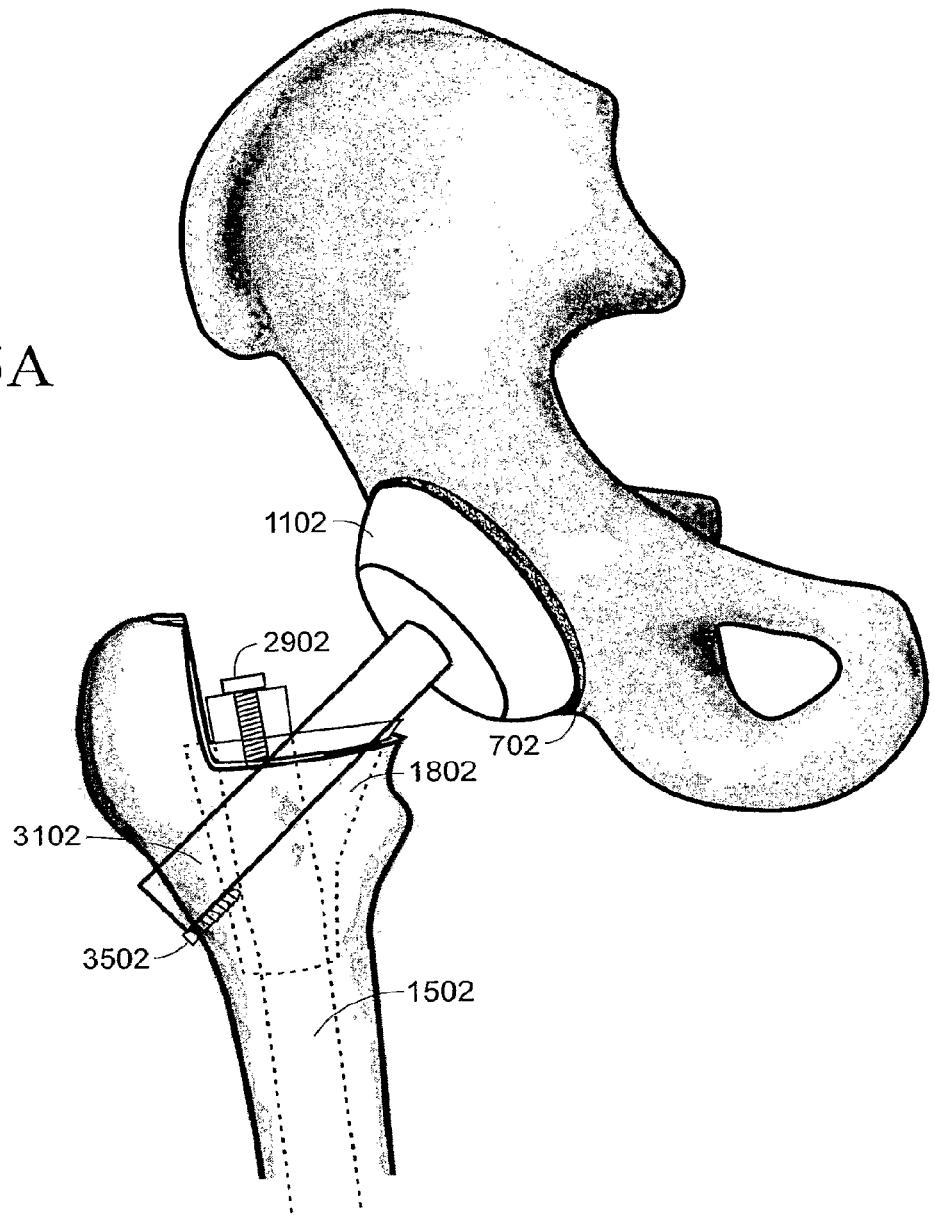
FIG. 35B illustrates a representation of a prosthetic acetabular cup, a prosthetic femoral head and neck, and an intramedullary rod installed in a support sleeve in the proximal femur and fixation screws to fix the prosthetic femoral neck in relation to the support sleeve and intramedullary rod in accordance with an embodiment of the present invention.

As described above, the present invention contemplates various embodiments of intramedullary rods, and also the optional use of a support sleeve (e.g., 1802). FIG. 34 illustrates a representation of a prosthetic acetabular cup 812, a prosthetic femoral head 1102 and neck 3102, and an intramedullary rod 1502 positioned in a support sleeve 1802 in the proximal femur in accordance with an embodiment of the present invention. It will be appreciated that the prosthetic femoral neck may receive additional fixation force relative to the intramedullary rod with the addition of a second fixation screw. FIG. 35A illustrates a representation of a prosthetic femoral neck fixation screw 3502, and FIG. 35B illustrates a representation of a prosthetic acetabular cup 812, a prosthetic femoral head 1102 and neck 3102, and an intramedullary rod 1502 positioned in a support sleeve 1802 in the proximal femur, and fixation screws 2902, 3502 to fix the prosthetic femoral neck 3102 relative to the intramedullary rod 1502 in accordance with an embodiment of the present invention. In one embodiment, a prosthetic femoral neck fixation screw 3502 may be inserted between the prosthetic femoral neck 3102 and the femur and threaded inward to wedge into a space between the prosthetic femoral neck 3102 and floor 1814 of the neck slot 1812. It will be appreciated that the wedging force created by such threading of the prosthetic femoral neck fixation screw 3502 advantageously fixes the prosthetic femoral neck 3102 in relation to the intramedullary rod 1502.

Figure 36:
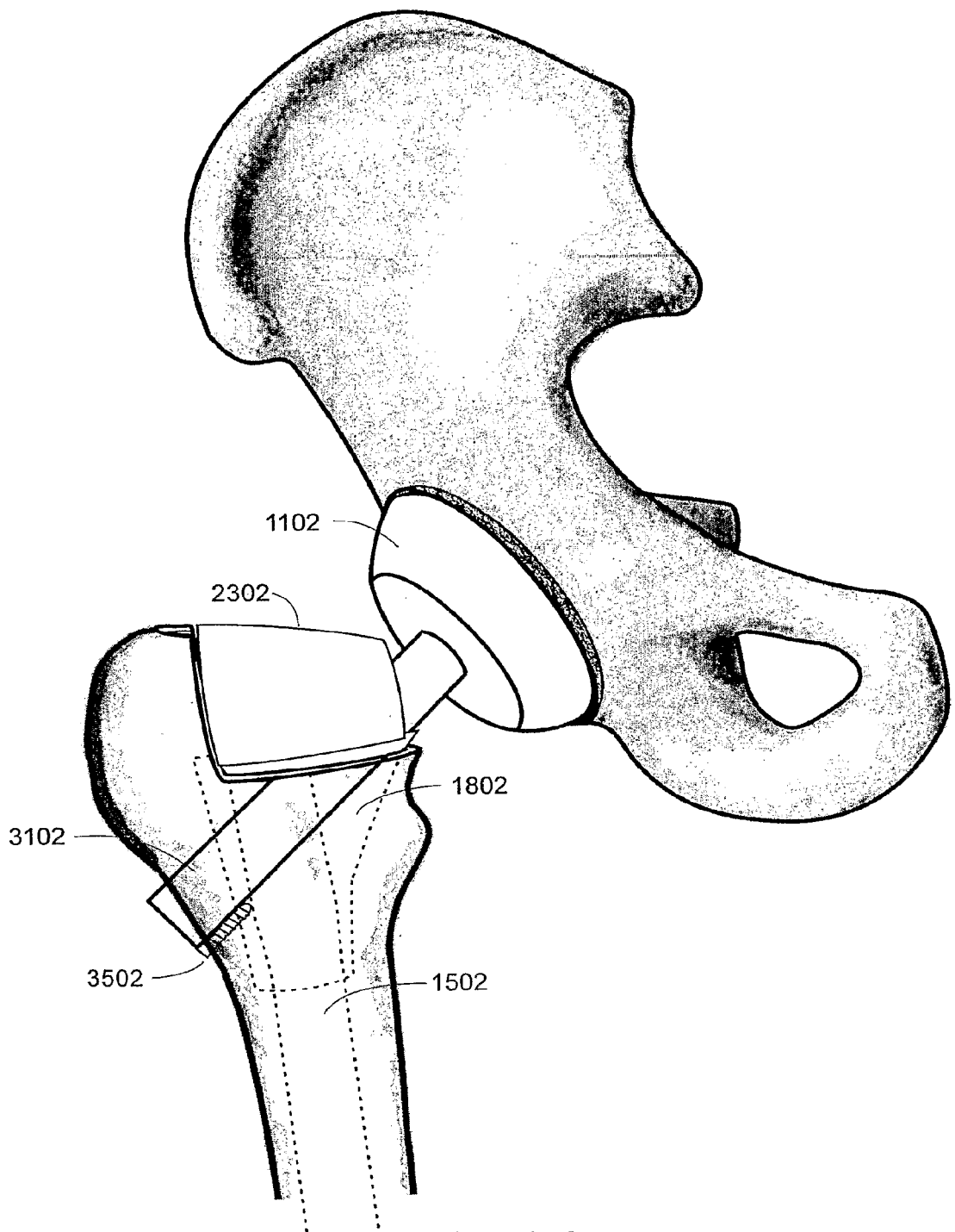
FIG. 36 illustrates a representation of a prosthetic acetabular cup, a prosthetic femoral head and neck, and an intramedullary rod installed in a support sleeve in the proximal femur with prosthetic femoral neck fixation screws and a cover in accordance with an embodiment of the present invention.

The present invention further contemplates that a portion of the prosthetic femoral neck may optionally be covered using a support sleeve cover that may advantageously provide support for the tissues about the hip joint. FIG. 36 illustrates a representation of a prosthetic acetabular cup, a prosthetic femoral head 1102 and neck 3102, and an intramedullary rod 1502 positioned in a support sleeve 1802 in the proximal femur with prosthetic femoral neck fixation screws and a support sleeve cover 2302 in accordance with an embodiment of the present invention.

The present invention further contemplates variations in the order that surgical steps are carried out. For example, in one such embodiment of the present invention, the proximal femur is prepared for insertion of an intramedullary rod prior to resection of the femoral neck and head. In this embodiment (and in other embodiments), an anterior or posterior incision may be used for surgical access the proximal femur. It will be appreciated, for example, that the posterior incision described in U.S. Pat. No. 6,991,656 may be used. With access to the proximal femur gained through appropriate incision, the proximal femur may be prepared as described above, e.g., in FIG. 14 and the associated text. Among other options, one of the support sleeves described above may be used, and if so, then the steps to prepare the proximal femur for a support sleeve may be performed as described above, including as in FIGS. 23A and 23B and associated text. If a support sleeve is to be used, it may then be positioned, and an intramedullary rod may then be inserted. If no support sleeve will be used, then the intramedullary rod may be inserted into the femur, e.g. as described in connection with FIG. 17A and the associated text. At this point, the alignment tool, e.g. as described in connection with FIG. 29B, may be joined via fixation bolt to the intramedullary rod, and a bore for a prosthetic femoral neck may then be created by introducing a neck bore drill bit through a guide block of the alignment tool. It will be appreciated that, in this embodiment, with the femoral neck and femoral head still in place, imaging may be used to advantageously confirm optimum path for the bore, which may be advanced into the femoral neck and head. Once the bore for the prosthetic femoral neck is created, attention is then turned to resection of the femoral neck and head, which may be performed in accordance with the steps described above, e.g., in connection with FIGS. 3A, 3B and 3C. Next, the acetabulum is prepared to receive the prosthetic acetabular cup. Advantageously, reaming of the acetabulum may be performed by fitting a reamer head into position through the surgical access to the proximal femur, and a reamer shaft may be advanced either through the created bore for the prosthetic femoral neck or through a stab incision lateral to a midportion of Smith-Peterson approach. It will be readily appreciated that a tissue-protecting guide sheath may be used to protect tissues from injury that may be caused by the rotating reamer shaft. It will be appreciated that the reamer shaft, once advanced to meet the reamer head, may be affixed to the reamer head and reaming may be performed with minimal insult to the soft tissue envelope about the hip joint. Once reaming of the acetabulum is complete, substantially as described above, e.g. in connection with FIG. 4B, the reamer head is detached from the reamer shaft and the reamer head and shaft are removed from the surgical space. A prosthetic acetabular cup is then positioned for impacting within the prepared acetabulum. Impacting may likewise be performed by advancing an impactor tool either through the bore created for the prosthetic femoral neck or through a stab incision. Again, a tissue-protecting guide sheath may be used. If desired, a conical sleeve with rounded end (e.g., FIG. 9A, item 912) may be positioned through the surgical access to the proximal femur whereupon the engaging threaded end of the impactor tool may be advanced through the conical sleeve. The impactor may then be threaded into the impaction bore of the prosthetic acetabular cup, and impacting may be performed as described above, e.g. in accordance with FIGS. 9A and 9B and the associated text. With the prosthetic acetabular cup impacted into place, one or more fixation screws may optionally be used to further secure the prosthetic acetabular cup to the acetabulum (e.g. FIGS. 8A, 8B, 8C and 8D and associated text). Attention may then be turned to positioning the prosthetic femoral head within the prosthetic acetabular cup, which may be carried out as described above in connection with FIGS. 11 and 12 and the associated text. As also described above (see FIG. 31 and associated text), the prosthetic femoral neck may then be advanced through the bore created for same and impacted to engage the prosthetic femoral head. Fixation screws may then be positioned and tightened to fix the location of the prosthetic femoral neck relative to the intramedullary rod (see, e.g., FIGS. 32A, 32B, 35A and 35B and associated text). If a support sleeve is used, then a support sleeve cover optionally may also be used. This is merely one of many alternative variations in the order of steps that may be performed in accordance with the method of the present invention.

Numerous variations and modifications of the invention will become readily apparent to those skilled in the art. Accordingly, the invention may be embodied in other specific forms without departing from its spirit or essential characteristics. The exemplary embodiments presented herein are to be considered in all respects only as illustrative and not restrictive and the scope of the invention is, therefore, indicated by the appended claims rather than by the foregoing descriptions. All changes which come within the meaning and range of equivalency of the claims are to be embraced within their scope.

What is claimed is:

1. A method of performing a total hip arthroplasty, comprising:
   surgically accessing an acetabulum;
   preparing the acetabulum to receive a prosthetic acetabular cup;
   seating the prosthetic acetabular cup in the prepared acetabulum;
   fitting a prosthetic femoral head within the prosthetic acetabular cup, the prosthetic femoral head rotatable with respect to the prosthetic acetabular cup;
   surgically accessing a femur;
   preparing the femur to receive an intramedullary rod, the intramedullary rod having a neck bore;
   inserting into the femur at least a portion of the intramedullary rod including the neck bore;
   creating a femoral bore into the femur, the femoral bore defining a passage through the femur from a side of the femur opposite the acetabulum and through the neck bore in the inserted intramedullary rod;
   inserting a head-engaging end of a prosthetic femoral neck into the femoral bore, through the neck bore in the inserted intramedullary rod to engage the prosthetic femoral head; and
   joining the head-engaging end of the prosthetic femoral neck to the prosthetic femoral head.

2. The method of claim 1, further comprising:
   fixing the prosthetic femoral neck with respect to the inserted intramedullary rod.

3. The method of claim 2, wherein the fixed prosthetic femoral neck extends from a first point external to the femur and through the femur to a second point where it joins the prosthetic femoral head.

4. The method of claim 1, wherein the femoral bore is created before a natural femoral head is removed.

5. The method of claim 1, wherein at least one anterior incision provides surgical access to the acetabulum and to the femur.

6. The method of claim 1, wherein a posterior incision provides surgical access to the femur.

7. The method of claim 1, wherein the creation of the femoral bore comprises:
   removably fixing an alignment tool to the intramedullary rod, the alignment tool having a guide bore which, when the alignment tool is removably fixed to the intramedullary rod, is in alignment with the neck bore of the intramedullary rod; and
   advancing a drilling bit through the guide bore, through the side of the femur opposite the acetabulum, through the neck bore in the intramedullary rod in a direction toward the acetabulum.

8. The method of claim 7, wherein the alignment tool further comprises a first fixation keyway and the intramedullary rod further comprises a second fixation keyway which removably interlocks with the first fixation keyway to facilitate removable fixation of the alignment tool to the intramedullary rod.

9. The method of claim 1, wherein the diameters of the prosthetic acetabular cup and the prosthetic femoral head both exceed 50 millimeters.

10. The method of claim 1, wherein the prosthetic acetabular cup includes at least one fixation bore and wherein seating the acetabular cup includes rotationally driving a fixation screw through the fixation bore to fix the prosthetic acetabular cup in a seated position within the prepared acetabulum.

11. The method of claim 10, wherein a hollow channel in the fixation screw is positioned to direct bodily fluid into a space between the prosthetic femoral head and the prosthetic acetabular cup.

12. The method of claim 1, wherein at least part of the prosthetic acetabular cup is cobalt chromium.

13. The method of claim 1, wherein the inner surface of the acetabular cup and the outer surface of the acetabular cup are made from different materials.

14. The method of claim 1, wherein the insertion of at least a portion of the intramedullary rod comprises inserting a guide wire into the intramedullary canal of the femur.

15. The method of claim 1, wherein a reamer is used in preparation of the acetabulum, the reamer having a reaming head and reaming shaft, the reaming head removable from the reaming shaft, the reaming head without the reaming shaft positioned at the acetabulum through the acetabular surgical access, the reaming shaft positioned through a second surgical access to engage the positioned reaming head.

16. The method of claim 1, wherein the reaming shaft is positioned through the femoral bore to engage the positioned reaming head.

17. The method of claim 1, wherein an impactor is used in seating prosthetic acetabular cup in the acetabulum, the impactor having an impactor head and an impactor shaft, the impactor head removable from the impactor shaft, the impactor head without the impactor shaft positioned through the acetabular surgical access to engage the prosthetic acetabular cup, the impactor shaft positioned through a second surgical access to engage the positioned impactor head.

18. The method of claim 1, wherein the impactor shaft is positioned through the femoral bore to engage the positioned impactor head.

19. A method of performing a total hip arthroplasty, comprising:
   surgically accessing an acetabulum and preparing it to receive a prosthetic acetabular cup and prosthetic femoral head;
   seating the prosthetic acetabular cup and prosthetic femoral head, the prosthetic femoral head rotatable within the prosthetic acetabular cup;
   surgically accessing a femur and preparing it to receive a support sleeve, the support sleeve comprising a rod bore and a neck passage;
   seating the support sleeve into a trochanteric region of the femur;
   inserting an intramedullary rod into the femur and through the rod bore of the support sleeve, the diameter of the rod bore configured to receive and hold a proximal region of the intramedullary rod while a distal stem of the intramedullary rod extends deeper into the femoral canal, the intramedullary rod comprising a neck bore aligned with the neck slot of the support sleeve;

inserting a prosthetic femoral neck from a position along a side of a patient's body, through a first side of the femur, through the neck passage and the neck bore to fixedly engage the prosthetic femoral head; and fixing the prosthetic femoral neck with respect to the intramedullary rod to thereby position the femur to usefully approximate normal rotational capacity with respect to the acetabulum.

20. The method of claim 19, wherein the prosthetic femoral head is rotatably fixed within the prosthetic acetabular cup prior to surgically accessing the acetabulum.

21. The method of claim 19, wherein bone-engaging walls of the support sleeve comprise a plurality of planar surfaces substantially perpendicular to the femoral canal.

22. The method of claim 19, wherein the diameters of the prosthetic acetabular cup and the prosthetic femoral head both exceed 50 millimeters.

23. The method of claim 19, wherein the outer surface of the prosthetic acetabular cup includes irregularities penetrable by new acetabular bone growth.

24. The method of claim 19, wherein the outer surface of the prosthetic acetabular cup includes protrusions facilitating seating within the prepared acetabulum.

25. The method of claim 19, wherein fixing the prosthetic femoral neck with respect to the intramedullary rod comprises rotationally driving a threaded fixation bolt into a threaded fixation bore in the intramedullary rod to exert a fixation force upon the prosthetic femoral neck, the threaded fixation bore perpendicular to and connecting with the neck bore.

26. The method of claim 25, wherein the fixation force upon the prosthetic femoral neck forces one or more ridges in the neck bore to engage one or more grooves formed in the prosthetic femoral neck.

* * * * *